US007935345B2

(12) United States Patent
Reason et al.

(10) Patent No.: US 7,935,345 B2
(45) Date of Patent: May 3, 2011

(54) **MONOCLONAL ANTIBODIES THAT SPECIFICALLY BIND TO AND NEUTRALIZE *BACILLUS ANTHRACIS* TOXIN, COMPOSITIONS, AND METHODS OF USE**

(75) Inventors: Donald Reason, Oakland, CA (US); Jianhui Zhou, Oakland, CA (US)

(73) Assignee: Children's Hospital & Research Center at Oakland, Oakland, CA (US)

( * ) Notice: Subject to any disclaimer, the term of this patent is extended or adjusted under 35 U.S.C. 154(b) by 409 days.

(21) Appl. No.: 12/123,339

(22) Filed: May 19, 2008

(65) Prior Publication Data

US 2009/0022736 A1    Jan. 22, 2009

Related U.S. Application Data

(60) Provisional application No. 60/931,279, filed on May 21, 2007.

(51) Int. Cl.
*A61K 39/40* (2006.01)
*C07K 16/00* (2006.01)
(52) U.S. Cl. ............... 424/164.1; 530/387.1; 530/388.1
(58) Field of Classification Search ........................ None
See application file for complete search history.

(56) References Cited

U.S. PATENT DOCUMENTS

| | | | |
|---|---|---|---|
| 5,591,631 | A | 1/1997 | Leppla et al. |
| 5,677,274 | A | 10/1997 | Leppla et al. |
| 6,828,110 | B2 | 12/2004 | Lee |
| 6,916,474 | B2 | 7/2005 | Harvey |
| 2002/0082386 | A1 | 6/2002 | Mangold |
| 2004/0018193 | A1 | 1/2004 | Alibek |
| 2004/0076638 | A1 | 4/2004 | Shiloach |
| 2004/0166120 | A1 | 8/2004 | Thomas |
| 2004/0171121 | A1 | 9/2004 | Leppla |
| 2004/0235075 | A1 | 11/2004 | Cullum |
| 2005/0031625 | A1 | 2/2005 | Mohamed |
| 2005/0123476 | A1 | 6/2005 | Bugge |
| 2005/0267294 | A1 | 12/2005 | Harvey |
| 2005/0287149 | A1 | 12/2005 | Keler |
| 2006/0083746 | A1 | 4/2006 | Young |
| 2006/0121045 | A1 | 6/2006 | Iverson |
| 2006/0140931 | A1 | 6/2006 | Mohamed |
| 2006/0153839 | A1 | 7/2006 | Mohamed |

OTHER PUBLICATIONS

Little, Passive protection by polyclonal antibodies against *Bacillus anthracis* infection in guinea pigs. Infect Immum. Dec. 1997; 65 (12):5171-5.
Welkos, The role of antibodies to Bacillus anthracis and anthrax toxin components in inhibiting the early stages of infection by anthrax spores, Microbiology. Jun. 2001; 147 (Pt 6): 1677-85.
Welkos, In-vitro characterisation of the phagocytosis and fate of anthrax spores in macrophages and the effects of anti-PA antibody, J. Med Microbiol. Oct. 2002; 51 (10):821-31.
Sastry, Generation and characterization of monoclonal antibodies to protective antigen of Bacillus anthracis, Indian J Exp Biol. Feb. 2003; 41 (2):123-8.
Zhao, Neutralizing monoclonal antibody against anthrax lethal factor inhibits intoxication in a mouse model, Hum Antibodies, 2003; 12(4):129-35.
Wild, Human antibodies from immunized donors are protective against anthrax toxin in vivo, Nat Biotechnol. Nov. 2003; 21 (11):1305-6. Epub Oct. 12, 2003.
Karginov, Treatment of anthrax infection with combination of ciprofloxacin and antibodies to protective antigen of *Bacillus anthracis*, FEMS Immunol Med Microbiol. Jan. 15, 2004;40 (1):71-4.
Wu, Vaccines and immunotherapies for the prevention of infectious diseases having cutaneous manifestations, J Am Acad Dermatol. Apr. 2004;50 (4):495-528; quiz 529-32.
Sawada-Hirai R, Human anti-anthrax protective antigen neutralizing monoclonal antibodies derived from donors vaccinated with anthrax vaccine adsorbed, J Immune Based Ther Vaccines. May 12, 2004;2(1):5.
Mohamed, Enhancement of anthrax lethal toxin cytotoxicity: a subset of monoclonal antibodies against protective antigen increases lethal toxin-mediated killing of murine macrophages, Infect Immun. Jun. 2004;72(6):3276-83.
Zhou, Somatic Hypermutation and diverse immunoglobulin gene usage in the human antibody response to the capsular polysaccharide of streptococcus pneumoniae type 6b, Infect Immun. Jun. 2004:72(6):3505-3514.
Brossier, Functional analysis of Bacillus anthracis protective antigen by using neutralizing monoclonal antibodies, Infect Immun. Nov. 2004;72(11):6313-7.
Huber, Generation of mouse polyclonal and human monoclonal antibodies against *Bacillus anthracis* toxin, Drugs Exp Clin Res. 2005;31(2):35-43.
Cui, Late treatment with a protective antigen-directed monoclonal antibody improves hemodynamic function and survival in a lethal toxin-infused rat model of anthrax sepsis, J Infect Dis. Feb. 1, 2005;191(3):422-34. Epub Dec. 22, 2004.
Mohamed, A high-affinity monoclonal antibody to anthrax protective antigen passively protects rabbits before and after aerosolized *Bacillus anthracis* spore challenge, Infect Immun. Feb. 2005;73(2):795-802.
Kasuya, Passive immunotherapy for anthrax toxin mediated by an adenovirus expressing an anti-protective antigen single-chain antibody, Mol Ther. Feb. 2005;11(2):237-44.
Cote, The Detection of Protection Antigen (PA) Associated with spores of *Bacillus anthracis* and the effects of anti-PA antibodies on spore germination and macrophage interactions, Microb Pathog. May-Jun. 2005;38(5-6):209-25. Epub Apr. 22, 2005.

(Continued)

Primary Examiner — Gary B. Nickol
Assistant Examiner — Khatol Shahnan-Shah
(74) Attorney, Agent, or Firm — Shweta Chandra; Carol L. Francis; Bozicevic, Field & Francis LLP

(57) ABSTRACT

The invention features compositions relating to antibodies that specifically bind to the protective antigen of *Bacillus anthracis*, fragments thereof, and nucleic acids encoding same. The invention further features methods of using such compositions.

24 Claims, 23 Drawing Sheets

OTHER PUBLICATIONS

Xu, Toxin-neutralizing monoclonal antibodies to the different domains of anthrax protective antigen, WEI SHENG WU XUE BAO. Dec. 2005;45(6):947-51.

Peterson, Human monoclonal anti-protective antigen antibody completely protects rabbits and is synergistic with ciprofloxacin in protecting mice and guinea pigs against inhalation anthrax, Infect Immun. Feb. 2006;74(2):1016-24.

Chen, Efficient neutralization of anthrax toxin by chimpanzee monoclonal antibodies against protective antigen, J Infect Dis. Mar. 1, 2006;193(5):625-33. Epub Feb. 2, 2006.

Rivera, A monoclonal antibody to *Bacillus anthracis* protective antigen defines a neutralizing epitope in domain 1, Infect Immun. Jul. 2006;74(7):4149-56.

Vitale, Prophylaxis and therapy of inhalational anthrax by a novel monoclonal antibody to protective antigen that mimics vaccine-induced immunity, Infect Immun. Oct. 2006;74(10):5840-7.

Lininger, The impact of incomplete vaccination schedules on the magnitude and duration of protective antigen-specific IgG responses in recipients of the US licensed anthrax vaccine, Vaccine. Nov. 13, 2006.

Duc, Immunization against anthrax using *Bacillus subtilis* spores expressing the anthrax protective antigen, Vaccine. Jan. 4, 2007;25(2):346-55. Epub Aug. 4, 2006.

Sun, Insertion of anthrax protective antigen into liposomal membranes:Effects of a receptor, JBC Papers in Press, Pub. Nov. 14, 2006, The American Society for Biochem and Molecular Bio, Printed Jan. 7, 2007.

Masri, Cloning and expression in *E coli* of a functional Fab fragment obtained from single human lymphocyte against anthrax toxin, Mol Immunol. Mar. 2007;44(8):2111-6. Epub Oct. 12, 2006.

Clone 1A5 heavy chain nucleic acid sequence

```
GAGTTAATTAATCTGCAGGAGTCGGGCCCAGGACTGGTGAAGCCCTCGGAGACCCTGTCCCTCACCTGCACTGTCTCTGGT
GGCGCCATGAACAGTCACTTCTGGAGTTGGATCCGGCAGTCCCCAGGGAAGGACTGGAGTGGATTGGGTATATCTATTCC
GGTGGGACTACCAACTACGACCCCTCCCTCAAGAGTCGAGTCGCCATTTCAATAGACACGTCCAAGAAGCAGTTCTCCCTG
AAATTGAGGTCTGTAGGCCAGGACACGGCCCTGTATTATTGTGCGAGAGGAGACATGGTGACTGGTCTTCCCCGGCCTCC
TACTGGGGCCAGGGCACCCTGGTCACCGTCTCCTCAGCCTCCACCAAGGGCCCATCGGTCTTCCCCCTGGCACCCTCCTCC
AAGAGCACCTCTGGGGGCACAGCGGCCCTGGGCTGCCTGGTCAAGGACTACTTCCCCGAACCGGTGACGGTGTCGTGGAAC
TCAGGCGCCCTGACCAGCGGCGTGCACACCTTCCCGGCTGTCCTACAGTCCTCAGGACTCTACTCCCTCAGCAGCGGTGTG
ACCGTGCCCTCCAGCAGCTTGGGCACCCAGACCTACATCTGCAACGTGAATCACAAGCCCAGCAACACCAAGGTGGACAAG
ACAGTTGAGCGCAAATGTTGTGTCAAAACTCACACATGCCCACCGTGCCCAGCACCTGAACTCCTGGGGGGACCGTCAGTCTTC
CTCTTCCCCCCAAAAACCCAAGGACACCCTCATGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCATAATGCCAAGACAAAGCCGCGGGAGGAGCAG
TACAACAGCACGTACCGTGTGGTCAGCGTCCTCACCGTCCTGCACCAGGACTGGCTGAATGGCAAGGAGTACAAGTGCAAG
GTCTCCAACAAAGCCCTCCCAGCCCCCATCGAGAAAACCATCTCCAAAGCCAAAGGGCAGCCCCGAGAACCACAGGTGTAC
ACCCTGCCCCCATCCCGGGATGAGCTGACCAAGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGACCACGCCTCCCGTGCTGGACTCCGACGGCTCC
TTCTTCCTCTACAGCAAGCTCACCGTGGACAAGAGCAGGTGGCAGCAGGGGAACGTCTTCTCATGCTCCGTGATGCATGAG
GCTCTGCACAACCACTACACGCAGAAGAGCCTCTCCCTGTCCCCGGGTAAATGA
```

Clone 1A5 heavy chain amino acid sequence

ELINLQESGPGLVKPSETLSLTCTVSGGAMNSHFWSWIRQSPGKGLEWIGYIYSGGTTNYDPSLKSRVAISIDTSKKQFSL
<u>                                CDR1                               CDR2</u>
KLRSVTAADTAVYYCARGDMVTGDPGDYWGQGTLVTVSSASTKGPSVFPLAPSSKSTSGGTAALGCLVKDYFPEPVTVSWN
<u>            CDR3</u>
SGALTSGVHTFPAVLQSSGLYSLSSVVTVPSSSLGTQTYICNVNHKPSNTKVDKTVERKCWARHTCPPCPAPELLGGPSVF
LFPPKPKDTLMISRTPEVTCVVVDVSHEDPEVKFNWYVDGVEVHNAKTKPREEQYNSTYRVVSVLTVLHQDWLNGKEYKCK
VSNKALPAPIEKTISKAKGQPREPQVYTLPPSRDELTKNQVSLTCLVKGFYPSDIAVEWESNGQPENNYKTTPPVLDSDGS
FFLYSKLTVDKSRWQQGNVFSCSVMHEALHNHYTQKSLSLSPGK*

VH germline gene: VH4-59; H isotype: IgG1

FIG. 1

Clone 1A5 light chain nucleic acid sequence
GAGGCCGGCCAGGTGATGACTCAGACTCCACTCTCCCTGCCCGTCACCCTTGGACAGTCGGCCTCCATCTCCTGCAGGTCT
AGTCAAAGCCTCGTATCCAGTGATGGAAAGACCTACTTGAATTGGTTTCACCAGAGGCCAGGCCAATCTCCAAGGCGCCTA
ATTTATAAGGTTTCTAAGCGGGACTCTGGGGTCCCCGACAGATTCAGCGGCAGTGGGTCAGGCACTGATTTCACACTGAAA
ATCAGCAGGGTGGAGGCTGAGGATGTTGGGGTTTATTTCTGCATGCAAGCTACACACTGGCTTTGGACGTTCGGCCAAGGG
ACCAAGGTGGAAATCAAACGAACTGTAGCTGCACCATCTGTCTTCATCTTCCCGCCATCAGTGAGCAGTTGAAATCTGGA
ACTGCCTCTGTTGTGTGCCTGCTGAATAACTTCTATCCCAGAGAGGCCAAAGTACAGTGGAAGGTGGATAACGCCCTCCAA
TCGGGTAACTCCCAGGAGAGTGTCACAGAGCAGGACAGCAAGGACAGCACCTACAGCCTCAGCAGCACCCTGACGCTGAGC
AAAGCAGACTACGAGAAACACAAAGTCTACGCCTGCGAAGTCACCCATCAGGGCCTGAGCTCGCCCGTCACAAAGAGCTTC
AACAGGGAGAGTGTGCGGCCGCATGA Clone 1A5 light chain amino acid sequence
EAGQVMTQTPLSLPVTLGQSASISCRSSQSLVSSDGKTYLNWFHQRPGQSPRRLIYKVSKRDSGVPDRFSGSGSGTDFTLK
                    CDR1                                   CDR2
ISRVEAEDVGVYFCMQATHWLWTFGQGTKVEIKRTVAAPSVFIFPPSDEQLKSGTASVVCLLNNFYPREAKVQWKVDNALQ
            CDR3
SGNSQESVTEQDSKDSTYSLSSTLTLSKADYEKHKVYACEVTHQGLSSPVTKSFNRGECAAA*

VL germline gene: A17; L isotype: kappa

FIG. 2

Clone 4A12 heavy chain nucleic acid sequence

GAGTTAATTAATCTGGTGCAGTCTGGCCATGAGGTGAAGCAGCCTGGGGCCTCAGTGAAGCTTTCCTGCAAGGCATCTGGA
TACTCCTTCAGCAGTTACTTTGTCCACTGGGTGCGCCAGGCCCCTGGACAAGGGCTTGAGTGGATGGGAATGATCAACCCT
CGTGGTGGTAGCACAAACTACGCACAGAAGTTCCAGGGCAGAGTCACCATGACCAGGGAGACGTCCACGAGTACAGTCTAC
ATGGAGCTGAGCGGCCTGAGAAGTGATGACACGGCCGTTTATTACTGTGCCAGAGTCAATTGGGCTGTCTTCCCCGTGGAC
TTTGACTACTGGGGCCAGGGAACCCTGGTCACCGTCTCCTCGGCGTCCTCGGGCACCACCAAGGGCTACTTCCCCCTGGCCCC
TGCTCCAGGAGCCACCTCTGGGGGCACAGCGGCCCTGGGCTGCCTGGTCAAGGACTACTTCCCTGAACCGGTGACGGTGTCG
TGGAACTCAGGCGCCCTGACCAGCGGCGTGCACACCTTCCCGGCTGTCCTACACAGTCTGAATCACCAGCGTGCCCCCTCAGCAGC
GTGGTGACCGTGCCCTCCAGCAGCTTGGGCACCCAGACCTACACCTGCAACGTGGATCACAAGCCCAGCAACACCAAGGTG
GACAAGAGAGTTGAGCGCAAATGTTGGGCGCCACACCTGTCTCCGAGACATCTGAGTCTCACATGCCAAGACAACCCGGGAG
GTCTTCCTCTTCCCCCCAAAACCCAAGGACACCCTCATGATCTCCCGGACCCCTGAGGTCACATGCGTGGTGGTGGACGTG
AGCCACGAAGACCCTGAGGTCAAGTTCAACTGGTACGTGGACGGCGTGGAGGTGCATAATGCCAAGACAAAGCCGCGGGAG
GAGCAGTACAACAGCACGTACCGTGTGGTCAGCGTCCTCACCGTCCTGCACCAGGACTGGCTGAATGGCAAGGAGTACAAG
TGCAAGGTCTCCAACAAAGCCCTCCCAGCCCCCATCGAGAAAACCATCTCCAAAGCCAAAGGGCAGCCCCGAGAACCACAG
GTGTACACCCTGCCCCCATCCCGGGATGAGCTGACCAAGAACCAGGTCAGCCTGACCTGCCTGGTCAAAGGCTTCTATCCC
AGCGACATCGCCGTGGAGTGGGAGAGCAATGGGCAGCCGGAGAACAACTACAAGACCACGCCTCCCGTGCTGGACTCCGAC
GGCTCCTTCTTCCTCTACAGCAAGCTCACCGTGGACAAGAGCAGGTGGCAGCAGGGGAACGTCTTCTCATGCTCCGTGATG
CATGAGGCTCTGCACAACCACTACACGCAGAAGAGCCTCTCCCTGTCTCCGGGTAAATGA

Clone 4A12 heavy chain amino acid sequence

ELINLVQSGHEVKQPGASVKLSCKASGYSFSSYFVHWVRQAPGQGFEWMGMINPRGGSTNYAQKFQGRVTMTRETSTTTVY
                          CDR1                           CDR2
MELSGLRSDDSAVYYCARVNWAYGDYDFDYWGQGTLVTVSSASTKGPSVFPLAPCSRSTSGGTAALGCLVKDYFPEPVTVS
                   CDR3
WNSGALTSGVHTFPAVLQSSGLYSLSSVVTVPSSSLGTQTYTCNVNHKPSNTKVDKTVERKCWARHTCPPCPAPELLGGPS
VFLFPPKPKDTLMISRTPEVTCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK*

VH germline gene: VH1-46; H isotype: IgG3

FIG. 3

Clone 4A12 light chain nucleic acid sequence

GAGGCCGGCCAGCAGATGACCCAGTCTCCATCCTCCCTGTCTGCATCTGTAGGAGACAGAGTCACCATCACTTGCCGGCA
AGTCAGAGCATTGCCAGGTATTTAAATTGGTATCAGCAGGAAAGCCCCGAAGGTCCTGATCTATGATGCATCC
AGTCTACATACTGGGGTCCCATCACAAGGTTCAGTGGCAGTGGATCTGGGACAGATTTCACTCTCACCATCAGCAGTCTGCGC
CCTGAAGATTTTGCAACTTACTACTGTCAACAGACTTACTCCCCTCACTTTCGGCGGAGGGACCAAGGTGGAGATC
AAACGAACTGTGGCTGCACCATCTGTCTTCATCTTCCCGCCATCTGATGAGCAGTTGAAATCTGGAACTGCCTCTGTTGTG
TGCCTGCTGAATAACTTCTATCCCAGAGAGGCCAAAGTACAGTGGAAGGTGGATAACGCCCTCCAATCGGGTAACTCCCAG
GAGAGTGTCACAGAGCAGGACAGCAAGGACAGCACCTACAGCCTCAGCAGCACCCTGAGCTCGAAAGCAGACTACGAG
AAACACAAAGTCTACGCCTGCGAAGTCACCCATCAGGGCCTGAGCTCGCCCGTCACAAAGAGCTTCAACAGGGGAGAGTGT
GCGGCCGCATGA

Clone 4A12 light chain amino acid sequence

EAGQQ<u>MTQSPSSLSASVGDRVTITCRASQSIARYLNW</u>YQQRPGKAPKVLIY<u>DASSLHT</u>GVPSRFSGSGSGTDFTLTISSLR
                 CDR1                                CDR2
PEDFATYYC<u>QQTYSTPLT</u>FGGGTKVEIKRTVAAPSVFIFPPSDEQLKSGTASVVCLLNNFYPREAKVQWKVDNALQSGNSQ
         CDR3
ESVTEQDSKDSTYSLSSTLTLSKADYEKHKVYACEVTHQGLSSPVTKSFNRGECAAA*

VL germline gene: O2; L isotype: kappa

FIG. 4

Clone 24B1 heavy chain nucleic acid sequence
GAGTTAATTAATCTGGTGGAGTCTGGGGGAGGCTTGGTACAGCCTGGCAGGTCCCTGAGACTCTCCTGTGCAGCCTCTGGA
TTCACCTTTGATGATTATGCCATGCACTGGGTCCGCCAAGTTGCAGGGAAGGGCCTGGAGTGGGTCTCAGGTATTAATTGG
AATAGTGCTAACATCGCCTATGCGGACTCTGTGAAGGGCCGATTCACCATCTCCAGAGACAACGCCAAGAAATTAGTCTAT
CTACAGATGCACAGTGCACACCGGCTGAGAGCTGAGGATACTGCCGTGTATTACTGTGCCAAAGATATGTATGGCGGGTACTTC
TTTGCCAAGTGGGGCCAGGGGCACCCTCGTGGGGACCGTCTCGGCTCCTCAGCTCCCAAGGACTACTTCCCCGAACCGGTGTCG
TCCTCCAAGAGCACCTCTGGGGGCACAGCGGCGGTGCACACCTTCCCGGCTGTCCTACAGTCCTCAAGGACTCTACTCCCTCAGCAGC
TGGAACTCAGGCGCCGTGCCTGCCTCCAGCAGTTGGGCACCCAGACCTACATCTGCAACGTGAATCACAAGCCCAGCAACACCAAGGTG
GTGGTGACCGTGCCCCCTCCAGCCAATGTTGGGCCGCCCAAAAACCCTGAGCGCACACCCTCATGATCTCCCGGACCCCTGAGGTCACATG
GACAAGACAGTTGAGCGCAAATGTTGGGCCGCCCAAAAACCCCTGAGCTCATCGGAGTCACATGCGTGGTGGTGGACGTG
AGCCACGAAGACCCTGAGGTCAAGTTCAACTGGTACGTGGACGGCGTGGAGGTGCATAATGCCAAGACAAAGCCGCGGGAG
GAGCAGTACAACAGCACGTACCGTGTGGTCAGCGTCCTCACCGTCCTGCACCAGGACTGGCTGAATGGCAAGGAGTACAAG
TGCAAGGTCTCCAACAAAGCCCTCCCAGCCCCCATCGAGAAAACCATCTCCAAAGCCAAAGGGCAGCCCCGAGAACCACAG
GTGTACACCCTGCCCCCATCCCGGGATGAGCTGACCAAGAACCAGGTCAGCCTGACCTGCCTGGTCAAAGGCTTCTATCCC
AGCGACATCGCCGTGGAGTGGGAGAGCAATGGGCAGCCGGAGAACAACTACAAGACCACGCCTCCCGTGCTGGACTCCGAC
GGCTCCTTCTTCCTCTACAGCAAGCTCACCGTGGACAAGAGCAGGTGGCAGCAGGGGAACGTCTTCTCATGCTCCGTGATG
CATGAGGCTCTGCACAACCACTACACGCAGAAGAGCCTCTCCCTGTCTCCGGGTAAATGA Clone 24B1 heavy chain amino acid sequence
ELINLVESGGGLVQPGRSLRLSCAASGFTFDDYAMHWVRQVAGKGLEWVSGINWNSANIAYADSVKGRFTISRDNAKKLVY
              CDR1                              CDR2
LQMHSLRAEDTAVYYCAKDMYGGGYFFAKWGQGSLVTVSSASTKGPSVFPLAPSSKSTSGGTAALGCLVKDYFPEPVTVS
                  CDR3
WNSGALTSGVHTFPAVLQSSGLYSLSSVVTVPSSSLGTQTYICNVNHKPSNTKVDKTVERKCWARHTCPPCPAPELLGGPS
VFLFPPKPKDTLMISRTPEVTCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK*

VH germline gene: VH3-9; H isotype: IgG1

FIG. 5

Clone 24B1 light chain nucleic acid sequence

GAGGCCGGCCAGCCAGTTGACCCAGTCTCCATCCTCCCTGTCTGCATCTGAAGGAGACAGAGTCACCATCACTTGCCGGGCC
AGTCAGAGTATTAGTAATTGGTTGGCCTGGTATCAGCAGAAACCAGGAAAGCCCCTAAACTCCTGATCTATAAGGCATCT
AGTTTAGAAAGTGGGGTCCCATCCAGGTTCAGCGGCAGTGGATCTGGGACAGAATTCACTCTCACCATCAGCAGCCTGCAG
CCTGATGATTTCGCAACTTATTATTGCCAACAGTATAGTGGTTCTGCCAAGGACCAAGGTGGAGATCAAA
CGAACTGTGGCTGCACCATCTGTCTTCATCTTCCCGCCATCTGATGAGCAGTTGAAATCTGGAACTGCCTCTGTTGTGTGC
CTGCTGAATAACTTCTATCCCAGAGAGGCCAAAGTACAGTGGAAGGTGGATAACGCCCTCCAATCGGGTAACTCCCAGGAG
AGTGTCACAGAGCAGGACAGCAAGGACAGCACCTACAGCCTCAGCAGCACCCTGACGCTGAGCAAAGCAGACTACGAGAAA
CACAAACTCTACGCCTGCGAAGTCACCCATCAGGGCCTGAGCTCGCCCGTCACAAAGAGCTTCAACAGGGGAGAGTGTGCG
GCCGCATGA

Clone 24B1 light chain amino acid sequence

EAGQQLTQSPSSLSASEGDRVTITCRAS<u>QSISNWLAWYQQKPGKAPKLLIY</u><u>KASSLESGVPSRFSGSGSGTEFTLTISSLQ</u>
            CDR1            CDR2
PDDFATYYC<u>QQYSGSATF</u>GQGTKVEIKRTVAAPSVFIFPPSDEQLKSGTASVVCLLNNFYPREAKVQWKVDNALQSGNSQE
    CDR3
SVTEQDSKDSTYSLSSTLTLSKADYEKHKLYACEVTHQGLSSPVTKSFNRGECAAA*

VL germline gene: L12; L isotype: kappa

FIG. 6

Clone 24G4 heavy chain nucleic acid sequence
GAGTTAATTAATCTGGTGGAGTCTGGGGGAGGCTTGATCAACCTGGGGGGGTCCCTGAGACTCTCCTGTACAGCCTCTGGG
TTCACGGTCAATAGCATGTACATGAACTGGTTCCGCCAGGCTCCAGGGAAGGGGCTGGAGTGGGTCTCAATTATTATAGC
GATGGTAGCACATTCTACGCAGACTCCGTGAAGGGCCGATTCACCATCTCCAGAGACAATTCCAAGAACACCCTGTATCTT
CAACTGAGCAGCCTGAGAGCCGAGGACACGGCCGTATATTACTGTGCCCGTCACCGTTCCCAAGGCCCATCGGTCTTCCCC
CTTTACGGGATGACTGGCTCAGGAGCCACCTGCAGGACACCTCCCTGGCTGTCCCGGCTGTGCACACCTTCCCGGCTGTCCTA
CGGGTGTCGTGGACATGGCACCCTGACCAGCGGCGTGCACACCTTCCCGGCTGTCCTACAGTCCTCAGGACTCTACTCC
CTCAGCAGCGTGGTGACCGTGCCCTCCAGCAACTTCGGCACCCAGACCTACACCTGCAACGTAGATCACAAGCCCAGCAAC
ACCAAGGTGGACAAGACAGTTGAGCGCAAATGTTGGCGCCACACCTGCCCCAGCACCTGCCCAGCACCTGAACTCCTGGG
GGACCGTCAGTCTTCCTCTTCCCCCCAAAACCCAAGGACACCCTCATGATCTCCCGGACCCCTGAGGTCACATGCGTGGTG
GTGGACGTGAGCCACGAAGACCCCGAGGTCCAAGTTCAACTGGTACGTGGACGGCGTGGAGGTGCATAATGCCAAGACAAAG
CCGCGGGAGGAGCAGTTCAACAGCACGTACCGTGTGGTCAGCGTCCTCACCGTCCTGCACCAGGACTGGCTGAATGGCAAG
GAGTACAAGTGCAAGGTCTCCAACAAAGCCCTCCCAGCCCCCATCGAGAAAACCATCTCCAAAGCCAAAGGGCAGCCCCGA
GAACCACAGGTGTACACCCTGCCCCCATCCCGGGATGAGCTGACCAAGAACCAGGTCAGCCTGACCTGCCTGGTCAAAGGC
TTCTATCCCAGCGACATCGCCGTGGAGTGGGAGAGCAATGGGCAGCCGGAGAACAACTACAAGACCACGCCTCCCGTGCTG
GACTCCGACGGCTCCTTCTTCCTCTACAGCAAGCTCACCGTGGACAAGAGCAGGTGGCAGCAGGGGAACGTCTTCTCATGC
TCCGTGATGCATGAGGCTCTGCACAACCACTACACGCAGAAGAGCCTCTCCCTGTCTCCGGGTAAATGA Clone 24G4 heavy chain amino acid sequence
ELINLVESGGGLIQPGGSLRLSCTASGFTVNSMYMNWFRQAPGKGLEWVSIIYSDGSTFYADSVKGRFTISRDNSKNTLYL
             CDR1                CDR2
QLSSLRAEDTAVYYCARAPQYDLWTGPLYGMDVWGQGTTVTVSSASTKGPSVFPLAPCSRSTSESTAALGCLVKDYFPEPV
      CDR3
TVSWNSGALTSGVHTFPAVLQSSGLYSLSSVVTVTSSNFGTQTYTCNVDHKPSNTKVDKTVERKCWARHTCPPCPAPELLG
GPSVFLFPPKPKDTLMISRTPEVTCVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGK*

VH germline gene: VH3-53; H isotype: IgG2

FIG. 7

Clone 24G4 light chain nucleic acid sequence
GAGGCCGGCCAGTCAGTTGACCCAGTCTCCATCCTCCCTGTCTGCATCTGTAGGAGACAGAGTCACCATCACTTGCCGGCC
AGTCAGGGCATTAGTCGTTATTTAGCCTGGTATCAGCAAAAACCAGGGAAAGCCCCTAAGCTCCTGATCTATGCTGCATCC
ACTTTGCAAAGTGGGGTCCCATCAAGGTTCAGCGGCAGTGGATCTGGGACAGATTTCACTCTCACCATCAGCAGCCTGCAG
CCTGAAGATTTTGCAACTTATTACTGTCAACAGCTTAATAGTTACCCACTCACTTTCGGCGGAGGGACCAAGGTGGAGGTC
AAACGAACTGTGGCTGCACCATCTGTCTTCATCTTCCCGCCATCTGATGAGCAGTTGAAATCTGGAACTGCCTCTGTTGCG
TGCCTGCTGAATAACTTCTATCCCAGAGAGGCCAAAGTACAGTGGAAGGTGGATAACGCCCTCCAATCGGGTAACTCCCAG
GAGAGTGTCACAGAGCAGGACAGCAAGGACAGCACCTACAGCCTCAGCAGCACCCTGACGCTGAGCAAAGCAGACTACGAG
AAACACAAAGTCTACGCCTGCGAAGTCACCCATCAGGGCCTGAGCTCGCCCGTCACAAAGAGCTTCAACAGGGGAGAGTGT
GCGGCCGCATGA Clone 24G4 light chain amino acid sequence
EAGQQLTQSPSSLSASVGDRVTITCRASQGISRYLAWYQQKPGKAPKLLIYAASTLQSGVPSRFSGSGSGTDFTLTISSLQ
                                      CDR1                                     CDR2
PEDFATYYCQQLNSYPLTFGGGTRVEVKRTVAAPSVFIFPPSDEQLKSGTASVACLLNNFYPREAKVQWKVDNALQSGNSQ
        CDR3
ESVTEQDSKDSTYSLSSTLTLSKADYEKHKVYACEVTHQGLSSPVTKSFNRGECAAA*

VL germline gene: L8; L isotype: kappa

FIG. 8

Clone 32E12 heavy chain nucleic acid sequence

CTGCAGGAGTCGGGCCCAGGACTGGTGAAGCCTTCGAAGACCCTGTCCCTCACCTGCACTGTCTCTGGTGGCTCCATCAGT
GGAAATTACTGGAGCTGGATCCGCCAGCCCGCCGGGAAGGGACTGGAGTGGATTGGGCGTATCTATATTAGTGGAGCCACC
ACTTATAAGCCCTCCCTCAAGAGTCGAGTCACCATGTCAGTAGACACGTCCAAAAACCAGTTCTCCCTGAAGCTGACGTCT
GTGACCGCCGCGGACACGGCCGTGTATTACTGCGCGAGACAAAGATTACTTTATTCGGGAAGTTATTATAATTGGTTC
GACCCCTGGGGCCAGGGAACCCTGGTCACCGTCTCCTCAGCATCGGCCTCCACCAAGGGCCCATCGGTCTTCCCCCTGGCACCCTCC
TCCAAGAGCACCTCTGGGGGCACAGCGGCCCTGGGCTGCCTGGTCAAGGACTACTTCCCCGAACCGGTGACGGTGTCGTGG
AACTCAGGCGCCCTGACCAGCGGCGTGCACACCTTCCCGGCTGTCCTACAGTCCTCAGGACTCTACTCCCTCAGCAGCGTG
GTGACCGTGCCCTCCAGCAGCTTGGGCACCCAGACCTACATCTGCAACGTGAATCACAAGCCCAGCAACACCAAGGTGGAC
AAGACAGTTGAGCGCAAATGTTGTGACAAAACTCACACATGCCCACCGTGCCCAGCACCTGAACTCCTGGGGGGACCGTCAGTC
TTCCTCTTCCCCCCAAAACCCAAGGACACCCTCATGATCTCCCGGACCCCTGAGGTCACATGCGTGGTGGTGGACGTGAGC
CACGAAGACCCTGAGGTCAAGTTCAACTGGTACGTGGACGGCGTGGAGGTGCATAATGCCAAGACAAAGCCGCGGGAGGAG
CAGTACAACAGCACGTACCGTGTGGTCAGCGTCCTCACCGTCCTGCACCAGGACTGGCTGAATGGCAAGGAGTACAAGTGC
AAGGTCTCCAACAAAGCCCTCCCAGCCCCCATCGAGAAAACCATCTCCAAAGCCAAAGGGCAGCCCCGAGAACCACAGGTG
TACACCCTGCCCCCATCCCGGGATGAGCTGACCAAGAACCAGGTCAGCCTGACCTGCCTGGTCAAAGGCTTCTATCCCAGC
GACATCGCCGTGGAGTGGGAGAGCAATGGGCAGCCGGAGAACAACTACAAGACCACGCCTCCCGTGCTGGACTCCGACGGC
TCCTTCTTCCTCTACAGCAAGCTCACCGTGGACAAGAGCAGGTGGCAGCAGGGGAACGTCTTCTCATGCTCCGTGATGCAT
GAGGCTCTGCACAACCACTACACGCAGAAGAGCCTCTCCCTGTCTCCGGGTAAATGA

Clone 32E12 heavy chain amino acid sequence

LQESGPGLVKPSETLSLTCTVSGGSISGNYWSWIRQPAGKGLEWIGRIYISGSTTYKPSLKSRVTMSVDTSKNQFSLKLTS
                            CDR1                                        CDR2

VTAADTAVYYCARDKDYFISGSYYNWFDPWGQGTLVTVSS ASTKGPSVFPLAPSSKSTSGGTAALGCLVKDYFPEPVTVSW
            CDR3

NSGALTSGVHTFPAVLQSSGLYSLSSVVTVPSSSLGTQTYICNVNHKPSNTKVDKTVERKCWARHTCPPCPAPELLGGPSV
FLFPPKPKDTLMISRTPEVTCVVVDVSHEDPEVKFNWYVDGVEVHNAKTKPREEQYNSTYRVVSVLTVLHQDWLNGKEYKC
KVSNKALPAPIEKTISKAKGQPREPQVYTLPPSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK*

VH germline gene: VH4-4; H isotype: IgG1

FIG. 9

Clone 32E12 light chain nucleic acid sequence

GAGGCCGGCCAGGTGTTGACGCAGTCTCCAGCCACCCTGTCTGTGTCTCCAGGGGAAAGAGCCACCCTCTCCTGCAGGGCC
AGTCAGAGTGTTGGCAGCAACTTAGCCTGGTACCAGCAGAAACCTGGCCAGGCTCCCAGGCTCCTCATCTATGGTGCATCC
ACCAGGGCCACTGGTATCCCAGCCAGGTTCAGTGGCAGTGGGTCTGGGACAGAGTTCACTCTCACCATCAGCAGCCTGCAG
TCTGAAGATTTTGCAGTTTATTACTGTCAGCAGGGTTGGACGTTCGGCCAAGGGACCAAGGTGGAAATCAAACGAACTGTG
GCTGCACCATCTGTCTTCATCTTCCCGCCATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCAATCGGGTAACTCCCAGGAGAGTGTCACA
GAGCAGGACAGCAAGGACAGCACCTACAGCCTCAGCAGCACCCTGACGCTGAGCAAAGCAGACTACGAGAAACACAAACTC
TACGCCTGCGAAGTCACCCATCAGGGCCTGAGCTCGCCCGTCACAAAGAGCTTCAACAGGGGAGAGTGTGCGGCCGCATGA

Clone 32E12 light chain amino acid sequence

EAG<u>QVLTQSPATLSVSPGERATLSC</u><u>RASQSVGSNLA</u><u>WYQQKPGQAPRLLIY</u><u>GAS</u><u>TRATGIPARFSGSGSGTEFTLTISSLQ</u>
                                                    CDR1                                                     CDR2
SEDFAVYYC<u>QQGWTF</u>GQGTKVEIKRTVAAPSVFIFPPSDEQLKSGTASVVCLLNNFYPREAKVQWKVDNALQSGNSQESVT
         CDR3

EQDSKDSTYSLSSTLTLSKADYEKHKLYACEVTHQGLSSPVTKSFNRGECAAA*

VL germline gene:L2; L isotype: kappa

FIG. 10

Clone 33F4 heavy chain nucleic acid sequence
GAGTTAATTAATCTGGTGGAGTCTGGGGGAGGCGTGGTCCGGCCTGGGAGGTCCCTGAGACTCTCCTGTGCAGCCTCTGGA
ATCATCTTCAGTAGCTATACTATGCACTGGGTCCGCCAGGCTCCAGGCAAGGGGCTGGAGTGGGTGGCACTTATCTCATAT
GATGGAACCAATAAAAACTACGGAGACTCCGTGAAGGGCCGATTCACCATCTCCAGAGACAATTCCAAGAATACGCTGTAT
CTGCAAATGAACAGCCTGAGAGCCGAGGACACGGCTGTGTATTACTGTGCGAGGGCCCGTGTATCAGCCTCCATATGGCAGC
AACTACAACCAGTACGGTATGGACGTCTGGGGCCAAGGGACCACGGTCACCGTCTCCTCAGCCTCCACCAAGGGCCCATCG
GTCTTCCCCCTGGCACCCTCCTCCAAGAGCACCTCTGGGGGCACAGCGGCCCTGGGCTGCCTGGTCAAGGACTACTTCCCC
GAACCGGTGACGGTGTCGTGGAACTCAGGCGCCCTGACCAGCGGCGTGCACACCTTCCCGGCTGTCCTACAGTCCTCAGGA
CTCTACTCCCTCAGCAGCGTGGTGACCGTGCCCTCCAGCAGCTTGGGCACCCAGACCTACATCTGCAACGTGAATCACAAG
CCCAGCAACACCAAGGTGGACAAGACAGTTGAGCGCAAATGTTGGGATGCGCAGACACCCCTGATCTCCCCGACCCTGAGG
CCCTGGGGGCGTGGTGGATGAGCTGAGCAGGAGGACCCTGAGGTCAAGTTCAACTGGTACGTGGACGGCGTGGAGGTGCATAATGCC
AAGACAAAGCCGCGGGAGGAGCAGTACAACAGCACGTACCGTGTGGTCAGCGTCCTCACCGTCCTGCACCAGGACTGGCTG
AATGGCAAGGAGTACAAGTGCAAGGTCTCCAACAAAGCCCTCCCAGCCCCCATCGAGAAAACCATCTCCAAAGCCAAAGGG
CAGCCCCGAGAACCACAGGTGTACACCCTGCCCCCATCCCGGGATGAGCTGACCAAGAACCAGGTCAGCCTGACCTGCCTG
GTCAAAGGCTTCTATCCCAGCGACATCGCCGTGGAGTGGGAGAGCAATGGGCAGCCGGAGAACAACTACAAGACCACGCCT
CCCGTGCTGGACTCCGACGGCTCCTTCTTCCTCTACAGCAAGCTCACCGTGGACAAGAGCAGGTGGCAGCAGGGGAACGTC
TTCTCATGCTCCGTGATGCATGAGGCTCTGCACAACCACTACACGCAGAAGAGCCTCTCCCTGTCTCCGGGTAAATGA Clone 33F4 heavy chain amino acid sequence
ELINLVESGGGVVRPGRSLRLSCAASGIIFSSYTMHWVRQAPGKGLEWVALISYDGTNKNYGDSVTGRFTISRDNSKNTLY
                        CDR1                   CDR2
LQMNSLRPEDTAVYYCARARVIVPAGSNYNQYGMDVWGQGTTVTVSSASTKGPSVFPLAPSSKSTSGGTAALGCLVKDYFP
                  CDR3
EPVTVSWNSGALTNGVHTFPAVLQSSGLYSLSSVVTVPSSSLGTQTYICNVNHKPSNTKVDKTVERKCWARHTCPPCPAPE
LLGGPSVFLFPPKDTLMISRTPEVTCVVVDVSHEDPEVKFNWYVDGVEVHNAKTKPREEQYNSTYRVVSVLTVLHQDWL
NGKEYKCKVSNKALPAPIEKTISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPGK*

VH germline gene: VH3-30; H isotype: IgG1

FIG. 11

Clone 33F4 light chain nucleic acid sequence
GAGGCCGGCCAGTCTGTGCTGACTCAGCCACCCTCAGTGTCCGTGTCCCCAGGACAGACAGCCAGCATCACCTGCTCTGGA
AATAAGTTGGGCAATAAATATGCTTGCTGGTATCAGCAGAAGCCAGGCCAGTCCCCTATACTGATCATCTATCAAGATAAG
AAGCGGCCCTCAGGGATCCCTGAGCGTTTCTCTGGCTCCAACTCTGGGAACACAGCCACTCTGACCATCAGCGGGACCCAG
GCTATGGATGAGGCTGACTATTATTGTCAGGCGTGGGACAGCGACACTGTGGTTTTCGGCGGAGGGACCAAGCTGACCGTC
CTAGGTCAGCCCAAGGCTGCCCCCTCGGTCACTCTGTTCCCGCCCTCCTCTGAGGAGCTTCAAGCCAACAAGGCCACACTG
GTGTGTCTCATAAGTGACTTCTACCCGGGAGCCGTGACAGTGGCCTGGAAGGCAGACAGCAGCCCCGTCAAGGCGGGAGTG
GAGACCACCACACCCTCCAAACAAAGCAACAACAAGTACGCGGCCAAGAGTTATCTGAGCCTGACGCCTGAGCAGTGGAAG
TCCCACAGAAGCTACAGCTGCCAGGTCACGCATGAAGGGAGCACCGTGGAGAAGACAGTGGCCCCTACAGAATGTTCATAG Clone 33F4 light chain amino acid sequence
EAGQSVLTQPPSVSVSPGQTASITCSGNKLGNKYACWYQQKPGQSPILIIYQDKKRPSGIPERFSGSNSGNTATLTISGTQ
                        CDR1                     CDR2
AMDEADYYCQAWDSDTVVFGGGTKLTVLGQPKAAPSVTLFPPSSEELQANKATLVCLISDFYPGAVTVAWKADSSPVKAGV
          CDR3
ETTTPSKQSNNKYAASSYLSLTPEQWKSHRSYSCQVTHEGSTVEKTVAPTECS*

VL germline gene: L2; L isotype: lambda

```
Afl III
TCA CAT GTT CTT TCC TGC GTT ATC CCC TGA TTC TGT TTC TAC CGC CTT TGA GTG AGC TGA TAC
CGC TCG CCG CAG CCC CGC AAC GAC TTG GCC CGA TTA ATG CAG GTC AGT GAG CTG AGA GCG CCC AAT ACG CAA
ACC GCC TCT CCC CGC GCG GCG GAT TCA ATG CAC CGA TTA CAG CGA GCA CGA GTT TCC CGA GAA AGC GGG
CAG TGA GCG CAA CGC AAT TAA TGT GAG TTA GCT CAC TCA TTA GGC ACC CCA GGC TTT ACA

RBS     EcoR I
CTT TAT GCT TCC GGC TCG TAT GTT GTG TGG AAT TGT GAG CGG ATA ACA ATT TCA CAC AGG AGG AAT TCT

Fse I
OmpA leader
ATG AAA AAG ACA GCT ATC GCG ATT GCA GTG GCA CTG GCT GGT TTC GCT ACC GTA GCG CAG GCC GGC C-
Met Lys Lys Thr Ala Ile Ala Ile Ala Val Ala Leu Ala Gly Phe Ala Thr Val Ala Not I              Linker
TAT GCG GCC GCA GGT GGC GGT GGC TCG GGC GGT GGT GGG TCG GGA GGC GGT GGG
                Gly Gly Gly Gly Ser Gly Gly Gly Gly Ser Gly Gly Gly Gly Pac I
TCC TTA ATT AA- TCT AGA GGC GGT TCT ATG AGC GAG GTG ACC GGG GTG
Ser GTG CCC ATC CTG GTC GAG GTA AAC GGC CAC AAG TTC AGC GTG TCC GGC GAG GGC GAG GGC
GAT GCC ACC TAC AAG CTG ACC CTG AAG TTC ATC TGC ACC ACC GGC AAG CTG CCC GTG CCC TGG CCC ACC
CTC GTG ACC ACC CTG ACC TAC GGC GTG CAG TGC TTC AGC CGC TAC CCC GAC CAC ATG AAG CAG CAC GAC TTC
TTC AAG TCC GCC ATG CCC GAA GGC TAC GTC CAG GAG CGC ACC ATC TTC TTC AAG GAC GAC GGC AAC TAC AAG
ACC CGC GCC GAG GTG AAG TTC GAG GGC GAC ACC CTG GTG AAC CGC ATC GAG CTG AAG GGC ATC GAC TTC AAG
GAG GAC GGC AAC ATC CTG GGG CAC AAG CTG GAG TAC AAC TAC AAC AGC CAC AAC GTC TAT ATC ATG GCC GAC
AAG CAG AAG AAC GGC ATC AAA GTG AAC TTC AAG ATC CGC CAC AAC ATC GAG GAC GGC AGC GTG CAG CTC GCC
GAC CAC TAC CAG CAG AAC ACC CCC ATC GGC GAC GGC CCC GTG CTG CTG CCC GAC AAC CAC TAC CTG AGC ACC
CAG TCC GCC CTG AGC AAA GAC CCC AAC GAG AAG CGC GAT CAC ATG GTC CTG CTG GAG TTC GTG ACC GCC GCC
GGG ATC ACT CTC GGC ATG GAC GAG CTG TAC AAG TAA GCT AGA Asc I     poly His                                                      Hind III
TTG GCG CGC CAT CAC CAT CAC CAT CAC TAA GCA TGC AAG CTT
        His His His His His His ***
```

FIG. 15

```
          Human kappa light chain V region primers
VKIa/Fse    TATAGTGGCCGGCCAGCAGTTGACCCAGTCTCCATCCTCCCTGTCTGCATC              51mer  (SEQ ID NO: 79)
VKIb/Fse    ATAGTGGCCGGCCAGCAGATGACCCAGTCTCCATC                             35mer  (SEQ ID NO: 80)
VKII/Fse    TATAGTGGCCGGCCAGGTGATGACTCAGACTCCACTCTC                         39mer  (SEQ ID NO: 81)
VKIII/Fse   TATAGTGGCCGGCCAGTTGACGCAGTCTCCAGCCACCCTGTC                      42mer  (SEQ ID NO: 82)
VKIIIb/Fse  TATAGTGGCCGGCCAGTGTTGACGCAGTCTCCAGCCACCCTGTC                    45mer  (SEQ ID NO: 83)
VKIV/Fse    ATAGTGGCCGGCCAGTGATGATGACCCAGTCTCCAGA                           35mer  (SEQ ID NO: 84)
VKV/Fse     ATAGTGGCCGGCCAGACACTCACGCAGTCTCCAGC                             35mer  (SEQ ID NO: 85)
VKVI/Fse    TATAGTGGCCGGCCAGGTGCTGACACAGTCTCCAGACTTTCAGTCTGTGACTCC          54mer  (SEQ ID NO: 86)

Human kappa light chain constant region primer
kapcon/Not  AGTCATGCGGCCGCACACTCTCCCCTGTTGAAGCTCTTTGTGACG                   45mer  (SEQ ID NO: 87)

Human heavy chain V region primers
VH1/Pac     ATAGTGTTAATTAACCTGGTGCAGTCTGGGGCTGAGGTGAAG                      42mer  (SEQ ID NO: 88)
VH2/Pac     ATAGTGTTAATTAACTTGAGGGAGTCTGGTCCTGCGCTGGTGAAACC                 47mer  (SEQ ID NO: 89)
VH3a/Pac    GTACGTGTTAATTAACCTGGTGGAGTCTGGGGGAGGC                           36mer  (SEQ ID NO: 90)
VH3c/Pac    GTAGTGTTAATTAACCTGGTGGAGTCTGGGGGAG                              34mer  (SEQ ID NO: 91)
VH3b/Pac    ATAGTGTTAATTAACCTGGTGGGGTCTGGGGGAGGCTTGGTCCAGCCTGGGGGGTCCCTG    60mer  (SEQ ID NO: 92)
VH4/Pac     ATAGTGTTAATTAACCTGCAGGAGTCGGGCCCAGGACTGGTGAAGCC                 47mer  (SEQ ID NO: 93)
VH5/Pac     TAGTGTTAATTAACCTGTGAAGTCTGGAGCAGAG                              35mer  (SEQ ID NO: 94)
VH6/Pac     ATAGTGTTAATTAACCTGCAGCAGTCCAGGACTG                              39mer  (SEQ ID NO: 95)
VH7/Pac     ATAGTGTTAATTAACCTGGTGCAGTCTGGCCATGAGGTGAAGCAGCCTGGGGCCTCAGTG    60mer  (SEQ ID NO: 96)

Human heavy chain constant region primers
G1hinge/Asc  GCATGTTCGGCGCGCCTCACAAGATTTGGGCTCTCTGCTTTC                     40mer  (SEQ ID NO: 97)
G2hinge/Asc  GTAGCAGGCGCGCCCAACATTTGCGCTCAACTGTCTTGTCCACC                   44mer  (SEQ ID NO: 98)
G3hinge/Asc  GGCTCTGGGCGCGCCGGGCATGTGAGTTGTGTCACC                           38mer  (SEQ ID NO: 99)
G4hinge/Asc  GTGCTGGGCGCGCCGGGCATGGGGGACCATATTGGAC                          38mer  (SEQ ID NO: 100)
ALPHA/Asc    GGAGGTGGGCGCGCCGGGCAGGGCACAGTCACATCCTG                         38mer  (SEQ ID NO: 101)
MU/ASC       AAGACGGCGGCGCGCCGGCAGCTCAGCAATCACTGG                           35mer  (SEQ ID NO: 102)
```

FIG. 16

Human lambda light chain V region primers

| | | | |
|---|---|---|---|
| VLAM1a | TATAGTGGCCGGCCAGTCTGCCCTGACTCAGCC | 33mer | (SEQ ID NO: 103) |
| VLAM1b | TATAGTGGCCGGCCAGTCTGTGCTGACTCAGCC | 33mer | (SEQ ID NO: 104) |
| VLAM2a | TATAGTGGCCGGCCAGTCTGTGCTGACTCAGCCACCCCTCAGTGTC | 45mer | (SEQ ID NO: 105) |
| VLAM2b | TATAGTGGCCGGCCAGTCTGAGCTGACTCAGCCACCCTCAGTGTC | 45mer | (SEQ ID NO: 106) |
| VLAM2c | TATAGTGGCCGGCCAGTCTGTGTGCTGACTCAGCCACCCCTCAGTGTC | 45mer | (SEQ ID NO: 107) |
| VLAM2d | ATAGTGGCCGGCCAGTCTGTGTGCTGACTCAGCCACCCTCGGTGTC | 35mer | (SEQ ID NO: 108) |
| VLAM3 | TATAGTGGCCGGCCAGACTGTGGTGACTCAGGAGC | 35mer | (SEQ ID NO: 109) |
| VLAM4 | TATAGTGGCCGGCCAGCCTGTGCTGACTCAGCC | 33mer | (SEQ ID NO: 110) |
| VLAM5 | TATAGTGGCCGGCCAGCCTGTGCTGACTCAATC | 33mer | (SEQ ID NO: 111) |

Human lambda light chain constant region primer

| | | | |
|---|---|---|---|
| LamCon8a | AGTCATGCGGCCGCTGAACATTCTGTAGGGGCCACTGTCTTCTCC | 45mer | (SEQ ID NO: 112) |
| LamCon8b | AGTCATGCGGCCGCCTATGAACATTCTGTAGGGGCCACTGTCTTCTCC | 48mer | (SEQ ID NO: 113) |

```
                                    Nhe I                    Human kappa light chain leader
GTA CTT AAT ACG ACT CAC TAT AGG CTA GCC ACC ATG GAA GCC CCA GCT CAG CTT CTC TTC CTC CTG CTA
                                              Met Glu Ala Pro Ala Gln Leu Leu Phe Leu Leu Leu Fse I                  Not I
CTC TGG CTC CCA GAT ACC ACC GGA GAG GCC GGC CTA A-- GCG GCC GCA TGA CCG CCC CTC TCC CTC CCC
Leu Trp Leu Pro Asp Thr Thr Gly                                 ***

CCC CCC TAA CGT TAC TGG CCG AAG CTT GAA TAA GGC CGG TGT GCG TTT GTC TAT ATG TTA TTT TCC
ACC ATA TTG CCG TCC CTC TTT GGC AAT CGG AGG GCC CAA GGT CTG TTC ACG AGC ATT CCT
AGG GGT CTT TGA GCC ACA ACG ATG GTA GGA TCT CTG TGC AAG AAC CCA CCT GTT GAA CCC CAG GTT CCT CTG
GAA GCT TCT TGA AGA CAA CCA CGT GTA TAA GAT ACA CCT GCA AAG GCG AAC CCA CAG TGC GAC
AGG TGC CTC TGC TGG GCC TAA GTT GTG GAA ATA GTT GCG GTA TTC AAC AAG GGG CTG AAG
GTT GTG AGT TGG GTG CAG CCC CAT GTG TCT TGT ATG GGA CCT CGG TGC TTT ACA TGT GTT
GAT GCC CAG AAG GTA CCC AAA CGT GGA TCT CCG GAC CAC GTT CTT TGA AAA ACA CGA
TAG TCG AGG TTA AAA CGT CTA

Pac I       Nco I      human heavy chain leader
TGA TAA TAT GGC CGC CA- -CC ATG GAG TTT GGG CTG AGC TGG CTT TTT GTG GCT ATT TTA AAA GGT
                            Met Glu Phe Gly Leu Ser Trp Leu Phe Val Ala Ile Leu Lys Gly Asc I                 human heavy CH2/CH3 constant domains
GTC CAG TGT GAG TTA ATT AAT GAG GCG CGC CAC ACA TGC CCA CCG TGC CCA GCA CCT GAA CTC CTG GGG
Val Gln Cys                    Ala Arg His Thr Cys Pro Pro Cys Pro Ala Pro Glu Leu Leu Gly GGA CCG TCA GTC TTC CTC TTC CCC CCA AAA CCC AAG GAC ACC CTC ATG ATC TCC CGG ACC CCT GAG GTC
Gly Pro Ser Val Phe Leu Phe Pro Pro Lys Pro Lys Asp Thr Leu Met Ile Ser Arg Thr Pro Glu Val
```

```
ACA TGC GTG GTG GAC GTG AGC CAC GAA GAC CCT GAG AAG TTC AAC TGG TAC GTG GAC GGC GTG
Thr Cys Val Val Asp Val Ser His Glu Asp Pro Glu Lys Phe Asn Trp Tyr Val Asp Gly Val

GAG GTG CAT AAT GCC AAG ACA AAG CCG CGG GAG GAG CAG TAC AAC AGC ACG TAC CGT GTG GTC
Glu Val His Asn Ala Lys Thr Lys Pro Arg Glu Glu Gln Tyr Asn Ser Thr Tyr Arg Val Val

AGC GTC CTG ACC GTC CTG CAC CAG GAC TGG CTG AAT GGC AAG GAG TAC AAG TGC AAG GTC TCC
Ser Val Leu Thr Val Leu His Gln Asp Trp Leu Asn Gly Lys Glu Tyr Lys Cys Lys Val Ser

AAC AAA GCC CTC
Asn Lys Ala Leu

CCA GCC CCC ATC GAG AAA ACC ATC TCC AAA GCC AAA GGG CAG CCC CGA GAA CCA CAG GTG TAC
Pro Ala Pro Ile Glu Lys Thr Ile Ser Lys Ala Lys Gly Gln Pro Arg Glu Pro Gln Val Tyr

ACC CTG
Thr Leu

CCC CCA TCC CGG GAT GAG CTG ACC AAG AAC CAG GTC AGC CTG ACC TGC CTG GTC AAA GGC TTC TAT CCC
Pro Pro Ser Arg Asp Glu Leu Thr Lys Asn Gln Val Ser Leu Thr Cys Leu Val Lys Gly Phe Tyr Pro

AGC GAC ATC GCC GTG GAG TGG GAG AGC AAT GGG CAG CCG GAG AAC AAC TAC AAG ACC ACG CCT CCC GTG
Ser Asp Ile Ala Val Glu Trp Glu Ser Asn Gly Gln Pro Glu Asn Asn Tyr Lys Thr Thr Pro Pro Val

CTG GAC TCC GAC GGC TCC TTC TTC CTC TAC AGC AAG CTC ACC GTG GAC AAG AGC AGG TGG CAG CAG GGG
Leu Asp Ser Asp Gly Ser Phe Phe Leu Tyr Ser Lys Leu Thr Val Asp Lys Ser Arg Trp Gln Gln Gly

AAC GTC TTC TCA TGC TCC GTG ATG CAT GAG GCT CTG CAC AAC CAC TAC ACG CAG AAG AGC CTC TCC CTG
Asn Val Phe Ser Cys Ser Val Met His Glu Ala Leu His Asn His Tyr Thr Gln Lys Ser Leu Ser Leu

Eag I
TCT CCG GGT AAA TGA CGG CCG CTT CCC TTT AGT GAG GGG TTA ATG CTT
Ser Pro Gly Lys ***  Arg Pro Leu Pro Phe Ser Glu Gly Leu Met Leu
```

FIG. 18 (Cont.)

Heavy Chain CDRs

```
                             CDR1                                              CDR2
24B1    ELINLVESGGGLVQPGRSLRLSCAASGFTFDDYAMHWVRQVAGKGLEWVSGINWNSANIA          60
33F4    ELINLVESGGGVVRPGRSLRLSCAASGIIFSSYTMHWVRQAPGKGLEWVALISYDGTNKN          60
24G4    ELINLVESGGGLIQPGGSLRLSCTASGFTVNSMYMNWFRQAPGKGLEWVSIIYSDGS-TF          59
4A12    ELINLVQSGHEVKQPGASVKLSCKASGYSFSSYFVHWVRQAPGQGFEWMGMINPRGGSTN          60
1A5     ELINLQESGPGLVKPSETLSLTCTVSGGAMNSHFWSWIRQSPGKGLEWIGYIYSGGT-TN          59
32E12   ----LQESGPGLVKPSETLSLTCTVSGGSISGNYWSWIRQPAGKGLEWIGRIYISGS-TT          55
         :  * :*:                 .:         . *  *.*:*:**:            .

CDR2 (con'd)                                      CDR3
24B1    YADSVKGRFTISRDNAKKLVYLQMHSLRAEDTAVYYCAKD--MYGGGG----YFFFAKWGQ         114    (SEQ ID NO: 29)
33F4    YGDSVTGRFTISRDNSKNTLYLQMNSLRPEDTAVYYCARARVIVPAGSNYNQYGMDVWGQ         120    (SEQ ID NO: 53)
24G4    YADSVKGRFTISRDNSKNTLYLQLSSLRAEDTAVYYCARAPQYDLWTG--PLYGMDVWGQ         117    (SEQ ID NO: 37)
4A12    YAQKFQGRVTMTRETSTTTVYMELSGLRSDDSAVYYCARVN--WAYGD----YDFDYWGQ         114    (SEQ ID NO: 21)
1A5     YDPSLKSRVAISIDTSKKQFSLKLRSVTAADTAVYYCARGD--MVTGDPG----DYWGQ         112    (SEQ ID NO: 13)
32E12   YKPSLKSRVTMSVDTSKNQFSLKLTSVTAADTAVYYCARDKDYFISGSYYN--WFDPWGQ         113    (SEQ ID NO: 45)
         *  .: :::..   :     ::: .::::*:****        .           ***

24B1    GSLVTVSS    122
33F4    GTTVTVSS    128
24G4    GTTVTVSS    125
4A12    GTLVTVSS    122
1A5     GTLVTVSS    120
32E12   GTLVTVSS    121
        *:  *****
```

FIG. 19A

Light Chain CDRs

```
                              CDR1                                      CDR2
4A12   EAGQQMTQSPSSLSASVGDRVTITCRASQSIAR----YLNWYQQRPGKAPKVLIYDASS  55
24G4   EAGQQLTQSPSSLSASVGDRVTITCRASQGISR----YLAWYQQKPGKAPKLLIYAAST  55
24B1   EAGQQLTQSPSSLSASEGDRVTITCRASQSISN----WLAWYQQKPGKAPKLLIYKASS  55
32E12  EAGQVLTQSPATLSVSPGERATLSCRASQSVGS----NLAWYQQKPGQAPRLLIYGAST  55
1A5    EAGQVMTQTPLSLPVTLGQSASISCRSSQSLVSSDGKTYLNWFHQRPGQSPRRLIYKVSK  60
33F4   EAGQSVLTQPPSVSVSPGQTASITCSGNK-LGN----KYACWYQQKPGQSPILIIYQDKK  55
       ****  :*   :    ::      *:          :  *:**:** :*  ***  .

CDR2 (con'd)                                       CDR3
4A12   LHTGVPSRFSGSGSGTDFTLTISSLRPEDFATYYCQQTYSTPLTFGGGTKVEIK----  109
24G4   LQSGVPSRFSGSGSGTDFTLTISSLQPEDFATYYCQQLNSYPLTFGGGTKVEVK----  109
24B1   LESGVPSRFSGSGSGTEFTLTISSLQPDDFATYYCQQ-YSGSATFGQGTKVEIK----  108
32E12  RATGIPARFSGSGSGTEFTLTISSLQSEDFAVYYCQQ----GWTFGQGTKVEIK----  105
1A5    RDSGVPDRFSGSGSGTDFTLKISRVEAEDVGVYFCMQATHWLWTFGQGTKVEIK----  114
33F4   RPSGIPERFSGSNSGNTATLTISGTQAMDEADYYCQAWDSDTVVFGGGTKLTVLGQPK  113
        .: :*.**** :** . * ** .   * *    *    . * * **   :

FIG. 19B
```

(SEQ ID NO: 25)
(SEQ ID NO: 41)
(SEQ ID NO: 33)
(SEQ ID NO: 49)
(SEQ ID NO: 17)
(SEQ ID NO: 57)

MONOCLONAL ANTIBODIES THAT SPECIFICALLY BIND TO AND NEUTRALIZE *BACILLUS ANTHRACIS* TOXIN, COMPOSITIONS, AND METHODS OF USE

CROSS-REFERENCED TO RELATED APPLICATIONS

This application claims the priority benefit of U.S. provisional application Ser. No. 60/931,279, filed May 21, 2007, which application is incorporated herein by reference in its entirety.

GOVERNMENT RIGHTS

This invention was made with government support under federal grant nos. AI57932 and AI066508 awarded by the National Institutes of Health. The United States Government has certain rights in this invention.

BACKGROUND

*Bacillus anthracis* is classified as one of seven Centers for Disease Control and Prevention category A agents that are considered major threats as bioweapons. *B. anthracis* is a rod-shaped Gram-positive spore-forming bacterium, which in nature is sometimes found in ruminants. Although natural anthrax infection in humans is rare (risk of infection through contact with diseased animals is about 1/100,000), it poses a very real threat from bioterrorism. The bacteria form hardy spores, which in nature are usually found in the soil. The spores are relatively heat resistant and can survive for decades under suitable conditions.

*B. anthracis* secretes a toxin (anthrax toxin) which contributes to bacterial virulence and causes many of the disease symptoms. Anthrax toxin is an AB-type toxin composed of a receptor-binding B-moiety and two catalytic A-moieties. The receptor-binding B-moiety is referred to as the protective antigen (PA). The two catalytic A-moieties are lethal factor (LF) and edema factor (EF). LF and PA combine to form lethal toxin, and EF and PA combine to form edema toxin. The receptor-binding PA component of the toxin facilities delivery of EF and LF into the cell by binding to cell surface receptors (called anthrax toxin receptors, ATR or ANTXR). Following entry into the cell in an endosome, heptaermized PA inserts into the endosomal membrane at acidic pH, forming a pore that mediates translocation of the enzymic components of the toxin from the endosomal compartment and into the cytosol. Entry of EF and LF into the cell cytoplasm then leads to cell death.

Anthrax has three primary modes of entering the human body: through the intestines (ingestion), lungs (inhalation), or skin (cutaneous). Although cutaneous anthrax is more readily treatable, inhaled anthrax typically results in an abrupt catastrophic illness having a mortality rate of greater than 80% in 2-4 days. If anthrax spores were spread through an act of terrorism, the event would likely be undiscoverable until large numbers of people sought treatment or died.

SUMMARY

The invention features compositions relating to antibodies that specifically bind to and neutralize the protective antigen (PA) of *Bacillus anthracis*, fragments thereof, and nucleic acids encoding same. The invention further features methods of using such compositions. The invention further features methods generating such compositions.

Accordingly, the present disclosure provides isolated polypeptides comprising: a heavy chain complementarity determining region (CDR) comprising contiguous amino acid sequences of a CDRH1, a CDRH2, and a CDRH3 of a heavy chain polypeptide of an antibody chosen from 1A5, 4A12, 24B1, 24G4, 32E12, or 33F4; or a light chain CDR comprising contiguous amino acid sequences of a CDRL1, a CDRL2, and a CDRL3 of a light chain polypeptide of an antibody chosen from 1A5, 4A12, 24B1, 24G4, 32E12, or 33F4.

In related embodiments, the polypeptide comprises a continuous amino acid sequence of the CDR of a $V_H$ region of an antibody chosen from 1A5, 4A12, 24B1, 24G4, 32E12, or 33F4. In other related embodiments, the polypeptide comprises a continugous amino acid sequence of CDRs of a $V_L$ region of an antibody chosen from 1A5, 4A12, 24B1, 24G4, 32E12, or 33F4.

In further related embodiments, the present disclosure also provides isolated nucleic acids comprising a nucleotide sequence encoding the polypeptides disclosed herein, which may be operably linked to a promoter. The present disclosure also provides vectors and host cells comprising such nucleic acids and vectors. In further related embodiments, the disclosure provides methods of producing a polypeptide comprising culturing such host cells under conditions to provide for polypeptide expression.

The present disclosure also provides expression vectors comprising a polynucleotide sequence encoding operably linked components, from 5' to 3': a promoter; a first signal sequence; a first polypeptide comprising at least a variable region of a light chain polypeptide of an antibody chosen from 1A5, 4A12, 24B1, 24G4, 32E12, or 33F4; a second leader sequence; a second polypeptide comprising at least a variable region of a heavy chain polypeptide of an antibody chosen from 1A5, 4A12, 24B1, 24G4, 32E12, or 33F4; and optionally, a detectable label.

In related embodiments the expression vectors include a polynucleotide sequence encoding a linker in lieu of the second leader sequence, wherein the linker is positioned such that expression from the promoter results in production of a single polypeptide comprising the first polypeptide, the linker, and the second polypeptide. In further related embodiments, the expression vectors include a polynucleotide sequence encoding an internal ribosome entry site (IRES) operably positioned 5' of the polynucleotide sequence encoding the second leader sequence.

The present disclosure also provides isolated antibodies comprising a heavy chain complementarity determining region (CDR) comprising contiguous amino acid sequences of a CDRH1, a CDRH2, and a CDRH3 of a heavy chain polypeptide of an antibody chosen from 1A5, 4A12, 24B1, 24G4, 32E12, or 33F4; and a light chain CDR comprising contiguous amino acid sequences of a CDRL1, a CDRL2, and a CDRL3 of a light chain polypeptide of an antibody chosen from 1A5, 4A12, 24B1, 24G4, 32E12, or 33F4; wherein the heavy chain CDR and light chain CDR are selected from the same antibody.

In related embodiments, the antibody comprises a heavy chain and a light chain complementary determining region (CDR) of an antibody chosen from 1A5, 4A12, 24B1, 24G4, 32E12, or 33F4. In further related embodiments, the isolated antibodies is 1A5, 4A12, 24B1, 24G4, 32E12, or 33F4, or an antigen-binding fragment thereof.

In related embodiments, the disclosure provides pharmaceutical compositions comprising a pharmaceutically acceptable carrier and an isolated antibody of the present disclosure. In further related embodiments, the disclosure provides methods of reducing toxicity of anthrax toxin in a subject, comprising administering to the subject such a pharmaceutical composition in an amount effective to reduce toxicity of anthrax toxin. In further related embodiments, the disclosure provides libraries of antibodies comprising at least one antibody or antigen-binding fragment of the antibodies of the present disclosure In further related embodiments, the disclosure provides methods of neutralizing a *B. anthracis* toxin, comprising contacting a *B. anthracis* toxin with an effective amount of an antibody of the present disclosure, wherein said contacting is effective to neutralize the toxin.

In related embodiments, the disclosure provides methods for detecting the presence of *B. anthracis* toxin in a sample comprising contacting a sample suspected of containing *B. anthracis* toxin with an antibody of the present disclosure, said contacting being under conditions to allow for formation of an specific antibody-antigen complex; and detecting the presence or absence of an antibody-antigen antibody complex; wherein the presence of the antibody-antigen complex indicates the presence of *B. anthracis* toxin in the sample.

The present disclosure also provides methods for producing a library of expression vectors containing immunoglobulin heavy and light chain-encoding sequences, which when expressed provide for production of an antigen-binding polypeptide that specifically binds an antigen of interest, the method comprising: subjecting RNA isolated from B lymphocytes to nucleic acid amplification in the presence of primer set, wherein said B lymphocytes are obtained from a subject exposed to an amount of antigen of interest effective to elicit an immune response to the antigen in the subject, said primer set comprises primers that specifically bind a collection of immunoglobulin (Ig) heavy chain and light chain variable genes, wherein the primers further contain a restriction enzyme recognition sequences of at least 8 bases, and said subjecting results in production of DNA amplification products comprising primer-introduced restriction enzyme recognition sequences and a nucleic acid sequence of a Ig heavy chain or light chain variable gene, wherein DNA amplification products comprising a sequence of an Ig heavy chain variable gene and DNA amplification products comprising a sequence of an Ig light chain variable gene contain different primer-introduced restriction enzyme recognition sequences; digesting the DNA amplification products with restriction enzymes that recognize said recognition sequences to produced digested DNA; and ligating said digested DNA into an expression cassette having first and second compatible cloning sites, wherein said ligating provides for directional cloning of DNA amplification products comprising a sequence of an Ig light chain variable gene into said first cloning site and for direction cloning of DNA amplification products comprising a sequence of an Ig heavy chain variable gene into said second cloning site; wherein a library of expression vectors containing immunoglobulin heavy and light chain-encoding sequences, which when expressed provide for production of an antigen-binding polypeptide that specifically binds to the antigen of interest.

These and other features will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 1 is a schematic of the nucleotide sequence (SEQ ID NO: 61) and corresponding amino acid sequence (SEQ ID NO: 1) of the heavy-chain of antibody 1A5. The $V_H$-region is in bold (SEQ ID NO: 13). CDR1, CDR2 and CDR3 are underlined (SEQ ID NOs: 14-16, respectively).

FIG. 2 is a schematic of the nucleotide sequence (SEQ ID NO: 62) and corresponding amino acid sequence (SEQ ID NO: 2) of the light-chain of antibody 1A5. The $V_L$-region is in bold (SEQ ID NO: 17). CDR1, CDR2 and CDR3 are underlined (SEQ ID NOs: 18-20, respectively).

FIG. 3 is a schematic of the nucleotide sequence (SEQ ID NO: 63) and corresponding amino acid sequence (SEQ ID NO: 3) of the heavy-chain of antibody 4A12. The $V_H$-region is in bold (SEQ ID NO: 21). CDR1, CDR2 and CDR3 are underlined (SEQ ID NOs: 22-24, respectively).

FIG. 4 is a schematic of the nucleotide sequence (SEQ ID NO: 64) and corresponding amino acid sequence (SEQ ID NO: 4) of the light-chain of antibody 4A12. The $V_L$-region is in bold (SEQ ID NO: 25). CDR1, CDR2 and CDR3 are underlined (SEQ ID NOs: 26-28, respectively).

FIG. 5 is a schematic of the nucleotide sequence (SEQ ID NO: 65) and corresponding amino acid sequence (SEQ ID NO: 5) of the heavy-chain of antibody 24B1. The $V_H$-region is in bold (SEQ ID NO: 29). CDR1, CDR2 and CDR3 are underlined (SEQ ID NOs: 30-32, respectively).

FIG. 6 is a schematic of the nucleotide sequence (SEQ ID NO: 66) and corresponding amino acid sequence (SEQ ID NO: 6) of the light-chain of antibody 24B1. The $V_L$-region is in bold (SEQ ID NO: 33). CDR1, CDR2 and CDR3 are underlined (SEQ ID NOs: 34-36, respectively).

FIG. 7 is a schematic of the nucleotide sequence (SEQ ID NO: 67) and corresponding amino acid sequence (SEQ ID NO: 7) of the heavy-chain of antibody 24G4. The $V_H$-region is in bold (SEQ ID NO: 37). CDR1, CDR2 and CDR3 are underlined (SEQ ID NOs: 38-40, respectively).

FIG. 8 is a schematic of the nucleotide sequence (SEQ ID NO: 68) and corresponding amino acid sequence (SEQ ID NO: 8) of the light-chain of antibody 24G4. The $V_L$-region is in bold (SEQ ID NO: 41). CDR1, CDR2 and CDR3 are underlined (SEQ ID NOs: 42-44, respectively).

FIG. 9 is a schematic of the nucleotide sequence (SEQ ID NO: 69) and corresponding amino acid sequence (SEQ ID NO: 9) of the heavy-chain of antibody 32E12. The $V_H$-region is in bold (SEQ ID NO: 45). CDR1, CDR2 and CDR3 are underlined (SEQ ID NOs: 46-48, respectively).

FIG. 10 is a schematic of the nucleotide sequence (SEQ ID NO: 70) and corresponding amino acid sequence (SEQ ID NO: 10) of the light-chain of antibody 32E12. The $V_L$-region is in bold (SEQ ID NO: 49). CDR1, CDR2 and CDR3 are underlined (SEQ ID NOs: 50-52, respectively).

FIG. 11 is a schematic of the nucleotide sequence (SEQ ID NO: 71) and corresponding amino acid sequence (SEQ ID NO: 11) of the heavy-chain of antibody 33F4. The $V_H$-region is in bold (SEQ ID NO: 53). CDR1, CDR2 and CDR3 are underlined (SEQ ID NOs: 54-56, respectively).

FIG. 12 is a schematic of the nucleotide sequence (SEQ ID NO: 72) and corresponding amino acid sequence (SEQ ID NO: 12) of the light-chain of antibody 33F4. The $V_L$-region is in bold (SEQ ID NO: 57). CDR1, CDR2 and CDR3 are underlined (SEQ ID NOs: 58-60, respectively).

Figure 14:
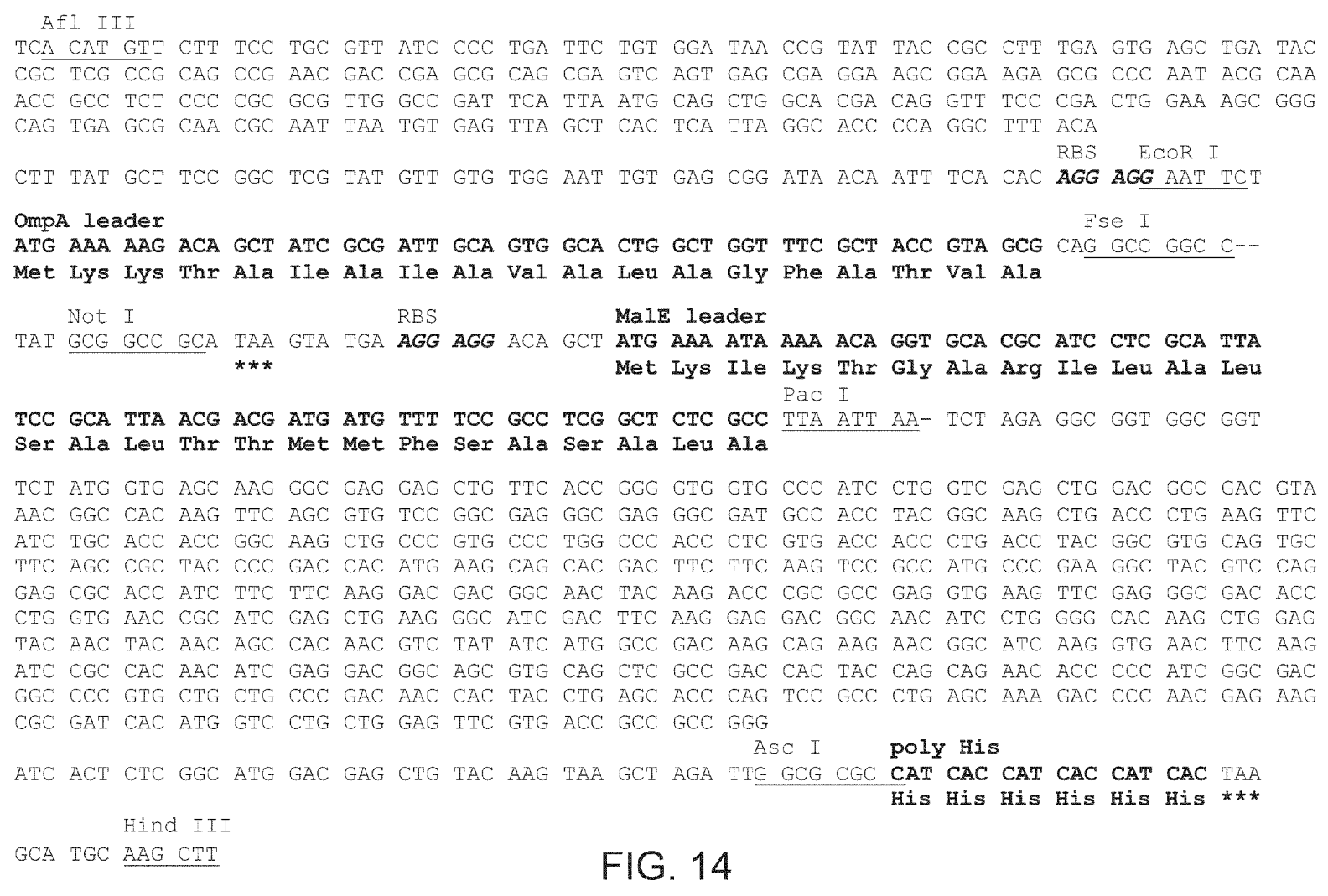

FIG. 14 is a schematic of the nucleotide sequence of the AflIII/HindIII pARC/Fab expression cassette (SEQ ID NO: 73). The amino acid sequences of the OmpA and MalE leader sequences are provided (SEQ ID NOs: 74 and 75, respectively). The amino acid sequence of the poly His tag is also provided (SEQ ID NO: 76). The underlined nucleotides indicate the recognition sites of the indicated restriction enzymes. "***" indicates a stop codon. "RBS" indicates a ribosomal binding site. The bold italic nucleotides indicate the RBSs. The bold nucleotides indicate the nucleotide sequences encoding the corresponding amino acid sequences.

FIG. 15 is a schematic of the nucleotide sequence of the AflIII/HindIII pARC/SC expression cassette (SEQ ID NO: 77). The amino acid sequence of the OmpA leader sequence, an exemplary linker, and a poly His tag are provided (SEQ ID NOS: 74, 78, and 76 respectively). The underlined nucleotides indicate the recognition sites of the indicated restriction enzymes. "***" indicates a stop codon. "RBS" indicates a ribosomal binding site. The bold italic nucleotides indicate the RBSs. The bold nucleotides indicate the nucleotide sequences encoding the corresponding amino acid sequences.

FIG. 16 is a schematic of the nucleotide sequences of primers (SEQ ID NOs: 79-102) that find use in the Example described herein. The nucleotide sequences in bold and underlined indicate the eight-base restriction enzyme recognition sites described in the Example described herein.

FIG. 17 is a schematic of the nucleotide sequences of the primers (SEQ ID NOs: 103-113) that find use in the Example described herein. The nucleotide sequences in bold and underlined indicate the eight-base restriction enzyme recognition sites described in the Example described herein.

FIG. 18 is a schematic of the nucleotide sequence of the AflIII/HindIII pCI/IRES expression cassette (SEQ ID NO: 114). The underlined nucleotides indicate the recognition sites of the indicated restriction enzymes. The bold nucleotides indicate the nucleotide sequences encoding the corresponding amino acid sequences.

FIG. 19A provides an alignment of the $V_H$ regions of antibodies 1A5, 4A12, 24B1, 24G4, 32E12, or 33F4. Amino acid residues that are conserved in all six antibodies are indicated by "*", with conservative substitutions indicated by ":" Underlining denotes CDR1, CDR2, and CDR3 in order from N- to C-terminus of the amino acid sequence provided (which may also be referred to as CDRH1, CDRH2, and CDRH3 to denote these are CDRs of a heavy chain polypeptide).

FIG. 19B provides an alignment of the $V_L$ regions of antibodies 1A5, 4A12, 24B1, 24G4, 32E12, or 33F4. Amino acid residues that are conserved in all six antibodies are indicated by "*", with conservative substitutions indicated by ":" Underlining denotes CDR1, CDR2, and CDR3 in order from N- to C-terminus of the amino acid sequence provided (which may also be referred to as CDRL1, CDRL2, and CDRL3 to denote these are CDRs of a light chain polypeptide).

FIGS. 20-21 are a set of graphs showing in vitro anthrax toxin neutralization by the human monoclonal antibodies 1A5, 4A12, 24B1, 24G4, 32E12, or 33F4. The vertical axis is % toxin neutralization. The horizontal axis is concentration of monoclonal antibody.

DEFINITIONS

Figure 13:
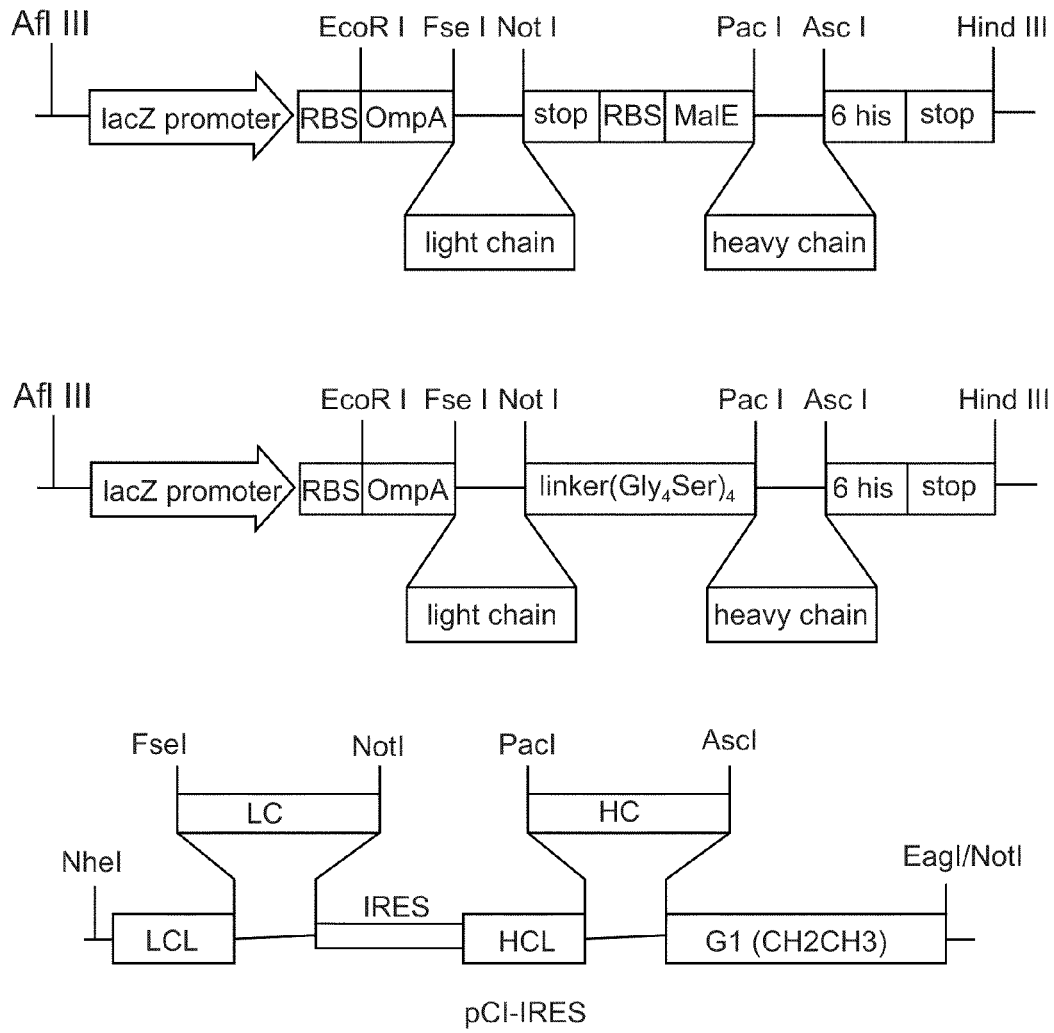
FIG. 13 is a schematic of various expression cassettes suitable for use in the present invention. Panel A depicts the AflIII/HindIII pARC/Fab expression cassette that is cloned into the AflIII/HindIII cloning site of pUC18 to produce the pARC/Fab vector. Panel B depicts the AflIII/HindIII pARC/SC expression cassette that is cloned into the AflIII/HindIII cloning site of pUC18 to produce the pARC/SC vector. Panel C depicts the NheI/NotI pCI/IRES expression cassette that is cloned into the NheI/NotI cloning site of pCI-neo expression vector. "LCL" is the human kappa light chain leader, "LC" is the light chain fragment, "IRES" is the internal ribosome entry site (IRES), "HCL" is the human heavy chain leader, "HC" is the heavy chain Fd region, "G1 (CH2/CH3)" is the human IgG1 CH2 and CH3 constant region domains.

Unless defined otherwise, all technical and scientific terms used herein have the same meaning as commonly understood by those of ordinary skill in the art to which this invention pertains. Any methods and materials similar or equivalent to those described herein can be used in the practice or testing of the present invention, the described methods and materials being exemplary.

As used herein, "protective antigen", abbreviated as "PA", refers to the protective antigen protein produced by the bacterium *B. anthracis*, and include any variants, isoforms and species homologs of anthrax PA, which may be naturally expressed by the bacterium, recombinantly expressed (Welkos et al., *Gene* 69: 287-300 (1988), or produced by synthetic methods. The terms “protective antigen” (and “PA”) include, for example, (1) the 764 amino acid PA, which may include a signal sequence (about 29 amino acids in length in the natural protein) at the N-terminus (for example, disclosed in GenBank accession nos. AAY15236 and P13423), (2) the secreted, unprocessed 83 kD form of PA (PA83; 735 amino acid in length) (for example, disclosed in GenBank accession no. 1ACC), (3) the proteolytically processed 63 kD form of PA (PA63; 569 amino acid in length), and (4) the 20 kDa N-terminal fragment (PA20), which is generated by proteolytic cleavage of PA83, unless a term is specifically limited to one form or the other.

As used herein, “antibody” is used in the broadest sense, and is meant to encompass whole antibodies, monoclonal antibodies (including full length monoclonal antibodies), polyclonal antibodies, multispecific antibodies (e.g., bispecific antibodies), single chain antibodies, full-length antibody, and antibody fragments (e.g., Fab, F(ab), $F(ab')_2$, Fv, single-chain Fab, and the like), which may be produced by recombinant methods and be modified by post-translational modification (e.g., glycosylation) and/or chemical modification (e.g., PEGylation). A “full-length antibody” refers to a complex comprised of at least two heavy (H) chain polypeptides and two light (L) chain polypeptides inter-connected by disulfide bonds. A full-length heavy chain polypeptide includes a heavy chain variable region (abbreviated herein as $V_H$) and a heavy chain constant region. A full length heavy chain constant region includes three domains, CH1, CH2 and CH3. Each full-length light chain polypeptide includes a light chain variable region (abbreviated herein as $V_L$) and a light chain constant region. A full length light chain constant region includes a light chain constant domain, $C_L$. The $V_H$ and $V_L$ regions can be further subdivided into regions of hypervariability, termed complementarity determining regions (CDRs), interspersed with regions that are more conserved, termed framework regions (FR). A full-length $V_H$ or $V_L$ includes three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate binding to host tissues or factors, such as various cells of the immune system (e.g., effector cells) and the first component (Clq) of the classical complement system.

As used herein, the term “antigen-binding fragment” of an antibody (or simply “antibody fragment”), refers to one or more fragments, or a portion, of an antibody that retain the ability to bind to a desired antigen, e.g., a *B. anthracis* antigen, such as PA, It has been shown that the antigen-binding function of an antibody can be performed by fragments of a full-length antibody. The term "antigen-binding fragment", includes, but is not limited to, (1) a Fab fragment, a monovalent fragment that contains the $V_L$, $V_H$, $C_L$ and $C_H$, domains; (2) a F(ab')$_2$ fragment, which refers to a bivalent fragment comprising two Fab fragments covantly linked, usually by a disulfide bridge, at the hinge region; (3) a single chain Fab, (4) a Fd fragment that includes the $V_H$ and $C_{H1}$, domains; (5) a Fv fragment that contains a $V_L$ domain of a light chain polypeptide and a $V_H$ domain of a heavy chain polypeptide, (6) a dAb fragment (Ward et al., *Nature* 341:544-546 (1989)), which contains a $V_H$ domain; and (7) an isolated complementarity determining region (CDR). Furthermore, although the two domains of the Fv fragment, $V_L$ and $V_H$, are coded for by separate genes, they can be joined, e.g., using recombinant methods, by a synthetic linker that enables production as a single polypeptide in which the $V_L$ and $V_H$ regions pair to form monovalent molecules (known as single chain Fv (scFv); see e.g., Bird et al., *Science* 242:423-426 (1988); and Huston et al., *Proc. Natl. Acad. Sci. USA* 85:5879-5883 (1988); which are incorporated by reference herein in their entirety). Such single chain antibodies are intended to be encompassed within the term "antigen-binding fragment" of an antibody. Antigen-binding fragments can be obtained using conventional techniques known to those with skill in the art, and the antigen-binding fragments are screened for desired antigen-binding properties as described above.

The term "specific binding of an antibody" or "antigen-specific antibody" in the context of a characteristics of an antibody refers to the ability of an antibody to preferentially bind to a particular antigen that is present in a homogeneous mixture of different antigens. In certain embodiments, a specific binding interaction will discriminate between desirable and undesirable antigens (e.g., "target" and "non-target" antigens) in a sample, in some embodiments more than about 10 to 100-fold or more (e.g., more than about 1000- or 10,000-fold). In certain embodiments, the affinity between an antibody and antigen when they are specifically bound in an antibody-antigen complex is characterized by a $K_D$ (dissociation constant) of less than $10^{-6}$ M, less than $10^{-7}$ M, less than $10^{-8}$ M, less than $10^{-9}$ M, less than $10^{-9}$ M, less than $10^{-11}$ M, or less than about $10^{-12}$ M or less.

The phrase "specifically binds to an antibody" or "specifically immunoreactive with" is also used when referring to an antigen such as a polypeptide (e.g., a PA of anthrax toxin), especially in the context of a binding reaction which is based on and/or is probative of the presence of the antigen under conditions which may also include a heterogeneous population of other molecules (e.g., as in a sample or in vivo). Thus, under the relevant conditions (e.g., designated immunoassay conditions), the specified antibody or antibodies bind(s) to a particular antigen or antigens and does not bind in a significant amount to other molecules present in the sample, particularly when compared to binding to an epitope of a target antigen against which the antibody was raised.

As used herein, "complementarity determining regions" or "CDRs", also known as hypervariable regions, are present in both the light chain and the heavy chain variable domains, and their amino acids determines the binding and specificity of each particular antibody for the antigen(s) to which it binds. There are at least two techniques for determining CDRs: (1) an approach based on cross-species sequence variability (e.g., Kabat et al., Sequences of Proteins of Immunological Interest (National Institute of Health, Bethesda, Md. 1987); and (2) an approach based on crystallographic studies of antigen-antibody complexes (Chothia et al. (1989), *Nature* 342: 877) (which are incorporated by reference herein in their entirety). The more highly conserved portions of variable domains among antibodies of different antigen binding specificity are referred to as the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat et al.) The constant domains are not directly involved in binding an antibody to an antigen, but exhibit various effector function, such as complement binding, participation of the antibody in antibody-dependent cellular toxicity, and the like. It is to be understood that reference to "a heavy chain complementarity determining region (CDR) comprising contiguous amino acid sequences of a CDRH1, a CDRH2, and a CDRH3" indicates that the CDR includes the recited amino acid sequences of the CDRH1, a CDRH2, and a CDRH3, but may differ in the amino acid sequences of the framework regions of the referenced heavy chain CDR. Likewise, reference to "a light chain CDR comprising contiguous amino acid sequences of a CDRL1, a CDRL2, and a CDRL3" indicates the CDR includes the rectied amino acid sequences of the CDRL1, CDRL2 and CDRL2, but may differ in the amino acid sequences of the framework regions of the referenced light chain CDR. A "contiguous amino acid sequence of a CDR" is meant to encompass both the sub-CDR sequences (i.e., CDR1, CDR2 and CDR3) as well as the framework sequences.

As used herein, the term "neutralizes", and grammatical variations thereof, in the context of the invention, refers to the ability of an antibody to inhibit activity of a antigen to which the antibody binds. For example, where the antibody binds to anthrax toxin protective antigen (PA), a neutralizing antibody is one that can inhibit anthrax toxin activity, e.g., particularly through inhibiting binding of PA to cells, inhibiting entry or translocation of EF or LF into a cell through a pore formed by PA in an endosomal compartment; inhibition of cleavage to generate a PA20 fragment; or other effect, upon binding of the antibody to the PA.

A "variant" of a polypeptide, such as a variant antibody polypeptide chain (variant heavy chain, variant light chain), is defined as a polypeptide that is altered by one or more amino acid residues relative to a reference sequence, e.g., a parent polypeptide, which may be a naturally occurring polypeptide. Such alterations include amino acid substitutions, deletions or insertions, or a combination thereof. Variants of an antibody heavy chain or light chain polypeptide of interest are those retain their activity in binding to an antigen of interest and, in some embodiments, biological activity as a neutralizing antibody.

Guidance in determining which and how many amino acid residues may be substituted, inserted or deleted may be found by comparing the sequence of a polypeptide to the sequence of a polypeptide with a related structure and function e.g., sequences from other sources (e.g., comparison between sequences from mammalian sources, e.g., human, rat, mouse, and the like). For example, acceptable amino acid substitutions, deletions, insertions, and additions in a region of a heavy chain or light chain polypeptide are readily determined by the ordinarily skilled artisan, e.g., by selecting a region outside of a CDR, modifying an amino acid sequence of a framework region, providing for framework region modifications that maintain association of CDRs of compatible heavy and light chain polypeptides, modifications that provide for further posttranslational and/or chemical modification (e.g., glycosylation, PEGylation, and the like), etc.

A "substitution" refers generally to a change that presents as a replacement of one or more amino acids or nucleotides by different amino acids or nucleotides, respectively, as compared to a reference amino acid sequence or polypeptide or nucleic acid. In the context of polypeptides, if a substitution is conservative, the amino acid that is substituted into a polypeptide has similar structural or chemical properties (e.g., charge, polarity, hydrophobicity, and the like) to the amino acid that it is substituting. Conservative substitutions of naturally occurring amino acids usually result in a substitution of a first amino acid with second amino acid from the same group as the first amino acid, where exemplary amino acid groups which provide groups of amino acids that can be considered conservative substitutions for one another are as follows: gly, ala; val, ile, leu; asp, glu; asn, gln; ser, thr; lys, arg; and phe, tyr.

A "deletion" refers generally to a change in an amino acid or nucleotide sequence in which one or more amino acid or nucleotide residues, respectively, are absent as compared to an amino acid sequence or nucleotide sequence of a reference polypeptide or reference nucleic acid. In the context of a polypeptide and polypeptide element amino acid or polynucleotide sequence, a deletion can involve deletion of about 2, about 5, about 10, up to about 20, up to about 30 or up to about 50 or more residues. A polypeptide or nucleic acid may also contain more than one deletion.

An "insertion" or "addition" refers to a change in an amino acid or nucleotide sequence which has presents as the addition of one or more amino acid or nucleotide residues, respectively, as compared to a reference amino acid sequence or nucleotide sequence. "Insertion" generally refers to addition to one or more residues within a sequence of a polypeptide or nucleic acid, while "addition" can be an insertion or refer to amino acid residues added at the N- or C-termini of a polypeptide or to nucleotides added to the 5' or 3' ends of a nucleic acid. An insertion or addition includes insertions or additions of up to about 10, up to about 20, up to about 30 or up to about 50 or more amino acids.

"Corresponding amino acids" or "corresponding nucleotides" refers to amino acid or nucleic acid residues that are at an identical position (i.e., they lie across from each other) when two or more sequences (amino acid or nucleic acid) are aligned. Methods for aligning and numbering amino acid and nucleic acid sequences as known in the art. For example, methods for aligning and numbering antibody sequences are described in Chothia, supra, Kabat supra, and others. As is known in the art (see, e.g. Kabat 1991 Sequences of Proteins of Immunological Interest, DHHS, Washington, D.C.), sometimes one, two or three gaps and/or insertions of up to one, two, three or four residues, or up to about 15 residues (particularly in the L3 and H3CDRs) may be made to one or both of the amino acids of an antibody in order to accomplish an alignment.

A "substitutable position", as in the context of variants of a given antibody heavy chain or light chain polypeptide, refers to a particular residue of an amino acid sequence or of a nucleic acid sequence that may be substituted by different amino acids or nucleic acids, respectively. Substitutions can be selected so as to not significantly decrease binding activity of the antibody (e.g., binding affinity, avidity, and/or specificity). A substitutable positions may also be referred to as "variation tolerant position".

A "natural" antibody is an antibody in which the heavy and light immunoglobulins of the antibody have been naturally selected by the immune system of a multi-cellular organism, as opposed to unnaturally paired antibodies made by recombinant techniques (e.g., phage display, expression in a host cell, etc.) or humanized antibodies. As such, parental antibodies do not usually contain any viral (e.g., bacteriophage M13) -derived sequences. Spleen, lymph nodes and bone marrow are examples of tissues that produce natural antibodies.

A "parent" antibody refers to the template or target for amino acid modifications (or, in the context of nucleic acids, the nucleic acid sequence encoding such a parent antibody).

As used herein, "monoclonal antibody" refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site or epitope. Furthermore, in contrast to conventional (polyclonal) antibody preparations which typically include different antibodies directed against different determinants (epitopes), each monoclonal antibody is directed against a single determinant on the antigen. In some embodiments, the monoclonal antibodies are produced in a host cell that is not contaminated by other immunoglobulins. The modifier "monoclonal" indicates the character of the antibody indicates the character of the antibody as being obtained from a substantially homogeneous population of antibodies, and is not to be construed as requiring production of the antibody by any particular method. For example, the monoclonal antibodies to be used in accordance with the present invention may be made by a hybridoma method as described by Kohler et al., *Nature* 256:495 (1975), or by a recombinant method as described in U.S. Pat. No. 4,816,567 (which are incorporated by reference herein in their entirety).

Monoclonal antibodies described herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA* 81, 6851-6855 (1984); which are incorporated by reference herein in their entirety).

As used herein, the term "epitope" means a determinant capable of specific binding to an antibody. Epitopes typically include chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. When the antibody, or antigen-binding fragment, is capable of binding to PA, the epitope is an amino acid sequence of the PA.

As used herein, the term "human antibody" is intended to include antibodies having at least a variable region, and usually both variable and constant regions derived from human germline immunoglobulin sequences. The human antibodies may include amino acid residues not encoded by human germline immunoglobulin sequences (e.g., mutations introduced by random or site-specific mutagenesis in vitro or by somatic mutation in vivo).

As used herein, a "humanized antibody" refers to an antibody comprising a human framework, at least one CDR derived from a non-human antibody, and in which any constant region present is substantially identical to a human antibody constant region, i.e., at least about 85-90%, or at least 95% identical. In some embodiments, one or more parts of a humanized antibody, except one or more CDRs which can be derived from a non-human antibody, are substantially identical to corresponding parts of one or more native human antibody sequences. In some embodiments, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having specificity. In some embodiments, framework region (FR) residues of the human immunoglobulin are replaced by corresponding non-human residues. Furthermore, humanized antibodies may comprise residues that are not found in the recipient antibody or in the donor antibody. In some embodiments, the humanized antibody comprises substantially all of at least one or two variable domains in which all or substantially all of the hypervariable loops correspond to those of a non-human immunoglobulin and all or substantially all of the FRs are those of a human immunoglobulin sequence. The humanized antibody can optionally further comprise at least a portion of an immunoglobulin constant region (Fc), e.g. that of a human immunoglobulin. (See Jones et al., *Nature* 321, 522 525 (1986); Riechmann et al., *Nature* 332, 323 329 (1988); and Presta, *Curr. Op. Struct. Biol.* 2, 593 596 (1992).) General reviews of humanized antibodies are provided by Morrison, 1985, *Science* 229:1202-1207 and Oi et al., 1986, *BioTechniques* 4:214 (which are incorporated by reference herein in their entirety). Those methods include isolating, manipulating, and expressing the nucleic acid sequences that encode all or part of immunoglobulin Fv variable regions from at least one of a heavy or light chain. Sources of such nucleic acid are well known to those skilled in the art. Suitable humanized antibodies can be produced by CDR substitution, as disclosed in U.S. Pat. No. 5,225,539; Jones et al. 1986 *Nature* 321:552-525; Verhoeyan et al. 1988 *Science* 239:1534; and Beidler et al. 1988 *J. Immunol.* 141:4053-4060 (which are incorporated by reference herein in their entirety).

An "Fv" fragment is the minimum antibody fragment which contains a complete antigen recognition and binding site. This region contains a dimer of one heavy and one light chain variable domain in a tight, non-covalent association ($V_H$-$V_L$ dimer). It is in this configuration that the three CDRs of each variable domain interact to define an antigen-binding site on the surface of the $V_H$-$V_L$ dimer. Collectively, the six CDRs confer antigen-binding specificity to an antibody. However, even a single variable domain (or half of an Fv containing only three CDRs specific for an antigen) has the ability to recognize and bind antigen, although at a lower affinity than the entire binding site.

As used herein, "Fab fragment" or "F(ab)" refers to an antibody fragment comprising a light chain fragment comprising a $V_L$ domain and a constant domain of a light chain, and a $V_H$ domain and a first constant domain ($C_H1$) of a heavy chain. Fab' fragments differ from Fab fragments by the addition of a few residues at the carboxyl terminus of the heavy chain $C_H1$ domain including one or more cysteines from the antibody hinge region. Fab'-SH is the designation herein for Fab' in which the cysteine residue(s) of the constant domains have a free thiol group. F(ab') fragments are produced by cleavage of the disulfide bond at the hinge cysteines of the F(ab')$_2$ pepsin digestion product. Additional chemical couplings of antibody fragments are known to those of ordinary skill in the art.

As used herein, "single-chain Fab fragment" or "single-chain F(ab)" refers to an antibody fragment comprising a light chain fragment comprising a $V_L$ domain and a constant domain of a light chain, and a heavy chain fragment comprising a $V_H$ domain and a first constant domain ($C_H1$) of a heavy chain, wherein the light chain fragment and the heavy chain are linked together with a linker to form a single chain. In some embodiments is about 4 or more amino acids. In certain embodiments, the linker is eight amino acids, such as Gly-Gly-Gly-Gly-Ser-Ser-Ser-Ser (SEQ ID NO: 118).

"Single-chain Fv", "scFv" or "sFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv see Pluckthun in The Pharmacology of Monoclonal Antibodies, vol. 113, Rosenburg et al. eds. Springer-Verlag, New York, pp. 269-315 (1994) (which is incorporated by reference herein in its entirety).

The term "identity" or "homology" shall be construed to mean the percentage of nucleic acid or amino acid residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Of interest are alignments involving contiguous nucleic acid sequences or amino acid sequences. Neither 5' or 3', or N- or C-terminal, extensions nor insertions shall be construed as reducing identity or homology. Methods and computer programs for the alignment are well known in the art. Sequence identity may be measured using sequence analysis software (e.g., Sequence Analysis Software Package, Genetics Computer Group, University of Wisconsin Biotechnology Center, 1710 University Ave., Madison, Wis. 53705). This software matches similar sequences by assigning degrees of homology to various substitutions, deletions, and other modifications.

The terms "protein" or "polypeptide" are intended to be used interchangeably. They refer to a chain of two or more amino acids, usually linked together with peptide or amide bonds, and may include post-translational modification (e.g., glycosylation, or phosphorylation) and/or chemical modification (e.g., PEGylation). Polypeptides can comprise more than one subunit, where each subunit is encoded by a separate DNA sequence.

The terms "nucleic acid molecule", "nucleic acid" and "polynucleotide" are used interchangeably and refer to a polymeric form of nucleotides of any length, either deoxyribonucleotides or ribonucleotides, and in some embodiments also includes analogs thereof (e.g., as in primers). Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, cDNA, recombinant polynucleotides, plasmids, vectors, isolated DNA of any sequence, isolated RNA of any sequence, nucleic acid probes, and primers.

As used herein, the term "host cell" (or "recombinant host cell") refers to a cell into which a recombinant expression vector has been introduced. Such terms refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell"

as used herein. Recombinant host cells include, e.g., mammalian cells (including cell lines) (e.g., CHO cells, lymphocytic cells, etc.), bacteria, yeast, and the like, particularly where the host cell is suitable for production of a heavy chain polypeptide or fragment thereof and/or a light chain polypeptide or fragment thereof.

As used herein, "recombinant" refers to a polynucleotide or polypeptide synthesized, expressed, or otherwise manipulated in vitro (e.g., "recombinant polynucleotide"), to methods of using recombinant polynucleotides to produce gene products in cells or other biological systems, or to a polypeptide ("recombinant polypeptide") encoded by a recombinant polynucleotide. "Recombinant" can also be used to refer to a cell that contains a heterologous nucleic acid, or expresses a peptide or protein encoded by such a heterologous nucleic acid, and usually provides for replication of such heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

As used herein, "heterologous" refers to a first entity (such as, nucleic acid or nucleotide sequence thereof, polypeptide or amino acid thereof, cassette, construct, vector, or host cell) and second entity (such as, nucleic acid or nucleotide sequence thereof, polypeptide or amino acid thereof, cassette, construct, vector, or host cell) are provided in an association that is not normally found in nature. For example, an antibody (a first entity) that is expressed in a bacterial host cell (a second entity) is heterologous to the bacterial host cell.

As used herein, "recombinant expression cassette" or "expression cassette" is a nucleic acid construct, generated recombinantly and/or synthetically, that contains control elements that are capable of facilitating expression of a coding sequence that is operably linked to the control elements and when introduced into a compatible host (capable of providing for expression from such control elements). Expression cassettes include at least promoters and optionally, transcription termination signals. In some embodiments, the recombinant expression cassette includes at least a nucleic acid to be transcribed and a promoter. Additional factors necessary or helpful in effecting expression can also be used as described herein. For example, transcription termination signals, enhancers, and other nucleic acid sequences that influence gene expression, can also be included in an expression cassette.

As used herein, a nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous or, where necessary to join two protein coding regions, contiguous and in reading frame, or at a location capable of effecting transcription of the sequence. For switch sequences, operably linked indicates that the sequences are capable of effecting switch recombination.

As used herein, "encoding" or "encoded by" refers to a nucleic acid sequence which under conditions for transcription (DNA) and for translation (DNA and RNA) for expression provides for production of a polypeptide sequence, wherein the polypeptide sequence or a portion thereof contains an amino acid sequence of at least 3 to 5 amino acids, at least 8 to 10 amino acids, or at least 15 to 20 amino acids from a polypeptide encoded by the nucleic acid sequence. Also encompassed are polypeptide sequences that are immunologically identifiable with a polypeptide encoded by the sequence.

The term "immunologically naïve" denotes an individual (e.g., a mammal such as a human patient) who has not been exposed to a particular antigen in an amount sufficient to elicit a detectable or significant immune response against the antigen.

The phrase "in a sufficient amount to elicit an immune response" (e.g., to an antigen) means that there is a detectable difference between an immune response indicator measured before and after administration of a particular antigen preparation. Immune response indicators include but are not limited to: antibody titer or specificity, as detected by an assay such as enzyme-linked immunoassay (ELISA), flow cytometry, immunoprecipitation, Ouchter-Lowry immunodiffusion; binding detection assays of, for example, spot, Western blot or antigen arrays; cytotoxicity assays, and the like.

A "primed" subject refers to a subject that has been exposed (e.g., by administration) to an antigen (e.g., a PA) in a sufficient amount to elicit an immune response that, upon subsequent exposure to an antigen presenting at least one epitope shared by the first antigen (e.g., as in a PA conjugate), provides for a protective immune response.

"In combination with" as used herein refers to uses where, for example, a first therapy is administered during the entire course of administration of a second therapy; where the first therapy is administered for a period of time that is overlapping with the administration of the second therapy, e.g. where administration of the first therapy begins before the administration of the second therapy and the administration of the first therapy ends before the administration of the second therapy ends; where the administration of the second therapy begins before the administration of the first therapy and the administration of the second therapy ends before the administration of the first therapy ends; where the administration of the first therapy begins before administration of the second therapy begins and the administration of the second therapy ends before the administration of the first therapy ends; where the administration of the second therapy begins before administration of the first therapy begins and the administration of the first therapy ends before the administration of the second therapy ends. As such, "in combination" can also refer to regimen involving administration of two or more therapies. "In combination with" as used herein also refers to administration of two or more therapies which may be administered in the same or different formulations, by the same of different routes, and in the same or different dosage form type.

The terms "subject," "host," "patient," and "individual" are used interchangeably herein to refer to any subject, usually a mammalian subject, for whom diagnosis or therapy is desired, particularly humans. Non-human subjects may include mammalian subjects such as cattle, sheep, goats, horses, donkeys, pigs, dogs, and the like. Where therapy is involved, the subject is any subject susceptible to anthrax infection and/or symptoms of anthrax disease.

As used herein, "detecting" or "assessing" includes any form of qualitative or quantitative measurement, and includes determining if an element is present or absent. The terms "determining", "measuring", "evaluating", "assessing" and "assaying" are used interchangeably and includes quantitative and qualitative determinations. Assessing may be relative or absolute. "Assessing the presence of" includes determining the amount of something present, and/or determining whether it is present or absent. As used herein, the terms "detecting," "determining," "measuring," and "assessing," and "assaying" are used interchangeably and include both quantitative and qualitative determinations.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

As used herein, "contacting" refers to combining two or more entities (e.g., two proteins, an enzyme and a cell, a cell and a candidate agent, etc.). Contacting can occur in a test tube or other container (e.g., binding of an antibody with an antigen), in the body of a subject.

The term "isolated" as used herein is meant to describe a material of interest (e.g., a polynucleotide, a polypeptide, antibody, host cell) that is in an environment different from that in which the material naturally occurs. "Isolated" is meant to include materials that are within samples that are substantially enriched for the material of interest and/or in which the material of interest is purified.

As used herein, the term "purified" refers to a compound (e.g., either a polynucleotide or a polypeptide) that is removed from its natural environment and is at least 60% free, at least 75% free, and at least 90% free up to 100% free from other components with which it is naturally associated.

DETAILED DESCRIPTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction. The publications discussed herein are provided solely for their disclosure prior to the filing date of the present application. Nothing herein is to be construed as an admission that the present invention is not entitled to antedate such publication by virtue of prior invention.

It must be noted that as used herein and in the appended claims, the singular forms "a", "an", and "the" include plural referents unless the context clearly dictates otherwise. Thus, for example, reference to "a cell" includes a plurality of such cells and reference to "the compounds" includes reference to one or more compounds and equivalents thereof known to those skilled in the art, and so forth.

Method of Cloning a Repertoire of Antibodies that Bind an Antigen of Interest

The disclosure provides for a method for obtaining a collection of antibodies that represent a repertoire of antibodies that are generated in response to administration of an antigen to a subject, e.g., to a human. In general, this method involves producing an expression library encoding at least the CDR-containing portion of the variable region of light chain-encoding cDNAs and at least the CDR-containing portion of the variable region of the heavy chain-encoding cDNAs, such that the expression library provides a collection of heavy chain-encoding and light-chain encoding nucleic acids that encodes these corresponding portions of antibodies, which are in turn representative of antibodies elicited in response to exposure of a subject to an antigen. In some embodiments, the antigen of interest is a toxin, e.g., a naturally occurring toxin, e.g., a bacterial toxin, e.g., PA.

In general, the method first involves obtaining mononuclear cells ("MNCs", which include antibody-producing B lymphocytes, also referred to as "B cells") from an animal exposed to an antigen of interest (e.g., such that the MNCs include circulating B cells specific the for antigen of interest), where the exposure is sufficient to elicit an immune response in the animal. Of particular interest is obtaining MNCs, particularly B cells, from a human who has been exposed to an antigen in an amount sufficient to elicit an immune response, more particularly a humoral immune response, to the antigen. In certain embodiments, the MNC is harvested or obtained from the peripheral blood or lymphatic organs of the subject, as may be appropriate or desired.

In certain embodiments, the subject is a human or a non-human animal, can include a mammalian or avian animal. Exemplary non-human mammalian animals include, without limitation, rodents (e.g., mouse, rat), rabbit, ungulates (e.g., horse, cattle, goats, pigs) and the like. An exemplary avian animal is a chicken or other livestock poultry (e.g., turkey). The subject may be naïve or previously exposed to the antigen, and may be exposed to the antigen as a result of vaccination or infection. Suitable antigen preparations include isolated antigen, vaccines (including recombinant vaccines, attenuated organisms (e.g., attenuated viruses or bacteria), and the like, and may include suitable adjuvant(s). Methods for immunizing a subject with an antigen of interest, as well as production of suitable antigen preparations, are well known in the art.

Methods for obtaining MNCs from a subject are well known, and any suitable method can be adapted to the methods disclosed here. Exemplary methods for separation of MNCs from blood (e.g., whole blood, plasma, serum, etc.) include density sedimentation, centrifugation over a suitable medium such as FICOLL™ or HISTOPAQUE®, passage over a nylon-wool column, affinity separation methods (e.g., antigen-coated magnetic beads, panning using an antigen-coated substrate), sorting in a fluorescent cell sorter (e.g., using an antibody against a relevant cell-surface marker, or by binding of a detectably labeled antigen) or by detection of binding of a detectably labeled antigen (e.g., a radiolabeled antigen). Where possible, it is generally preferable to decrease the number of manipulation steps. In addition, it may be desirable, although not necessary, to enrich for B cells in the MNC population obtained, and may be further desirable to enrich for antibody-producing B cells, especially those which produce an antibody that binds an antigen of interest and/or produces an antibody having desirged antigen-binding characteristics. In general, the MNCs (and B cells) can be obtained from whole blood of the animal exposed to the antigen. Separation methods can include appropriate washing steps. Plasma from the blood sample from which the MNCs are isolated can be retained for analysis as desired.

Optionally, an aliquot of MNCs obtained can be cultured under suitable conditions to provide for antibody production by B cells in the MNC population. The supernatant can then be assayed to determine the presence or absence of antibody secreted, and, where desired, determine the antigen specificity and/or isotype. This step can be useful as a double check to verify that the B cells in the population produce an antibody of interest, and further that antigen-specific B cells of the relevant antigen specificity were circulating in the subject at the time of sample collection. Where desired, multiple samples can be obtained from the subject at different time points, and the MNCs from these different timepoints cultured to determine the optimal sample for use in subsequent steps (e.g., a sample producing the higher level of antibody of interest). Samples from the same or different subjects can be pooled where desired.

Once a desired population of mononuclear cells is obtained, RNA is extracted from the cells using any suitable method. The isolated RNA is then used as a template for production of cDNA to generate a cDNA population. This cDNA is then used as a template for nucleic acid amplification, which can be accomplished by any of a variety of techniques (e.g, polymerase chain reaction (PCR)), where amplification is conducted using Ig-specific primers, particularly primers designed to provide for production of a collection of DNA fragments encoding at least the CDR-containing portion of variable region of light chain-encoding cDNA and/or at least the CDR-containing portion of the variable region of the heavy chain-encoding cDNA. Such primers can be based on nucleic acid sequences generally conserved among different heavy chain polypeptide-encoding sequences and on nucleic acid sequences generally conserved among different light chain polypeptide-encoding sequences.

The disclosure provides a set of H- and L-chain specific primers, which are provided in FIGS. 16-17, that encompass all known human V gene families and incorporate the restriction sites of infrequent-cutter restriction enzymes (exemplified by 8 base recognition sequences) compatible with the expression vectors described in more detail below (see expression vectors described in FIG. 13). Use of these primers thus provides for production of amplification products from a wide range of human Ig gene products.

The DNA fragments generated by nucleic acid amplification as described here is referred to as a DNA fragment library, which library contains different nucleic acid sequence encoding different CDR-containing portions of different variable regions of light chain and heavy chain polypeptides. In one embodiment, the DNA fragment library includes nucleic acid encoding full-length variable regions of different heavy and light chain polypeptides, and can further include nucleic acid encoding different full-length heavy chain and light chain polypeptides.

The DNA fragment library produced from the nucleic acid amplification step can then inserted into an expression cassette of an expression vector to generate a cDNA expression library. Any of a number of suitable vectors can be used as the basis for expression vectors. As used herein, the term "vector" refers to a nucleic acid molecule capable of amplifying, maintaining or expressing another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. Exemplary viral vectors include replication defective retroviruses, adenoviruses and adeno-associated viruses.

In some embodiments, the DNA fragments described above are ligated into one of a set of specifically engineered plasmid vectors. These vectors are designed so that cloning of the cDNA fragment requires use of an infrequently cutting enzyme at the ligation site. Other vectors can prove less than optimal, since during library construction it is necessary to digest heavy- and light-chain encoding amplification (e.g., PCR) products with restriction enzymes to facilitate directional cloning into the recipient expression vector. Although other vectors required use of enzymes selected to occur infrequently in germline immunoglobulin genes, recognition sequences for these enzymes often arise as a consequence of somatic mutation, especially in the CDR3 region of the H chain. Although it is usually possible to "engineer around" this problem on a library by library basis, it is more efficient to use methodologies and constructs that minimize the occurrence of the problem from the start.

To this end, the present disclosure provides a matched system of vectors and primers designed specifically for repertoire cloning. In this system the entire light (L) chain and the V/D/J/CH1 domains of the heavy (H) chain are inserted in frame with sequences specifying leader peptides that direct the synthesized product to the periplasmic space of *E. coli*. Vectors are designed with minimal internal sequence homology (for stability), and incorporate features required for protein expression and purification. A central feature of this system is the use of rare-cutting restriction enzymes with 8-base recognition sequences. These sequences do not occur in the human germline Ig genes, and rarely arise in the course of affinity maturation of the response. Exemplary enzymes having recognition sequences of 8 bases or longer include, but are not necessarily limited to, Fse I, Not I, Pac I, Asc I, Sfi I, Swa I, Smi I, Srf I, SgrA I Sgf I Sda I Sbf I, Pme I, Mss I, and FspA I. It will generally be desirable to provide for different enzyme recognition sequences flanking each of the cloning sites for the L and H chains in the construct, as exemplified in FIG. 13.

Primers useful for production of amplification products that can be readily inserted in these expression vectors can be designed so as to include restriction sites for enzymes having recognition sites at least 8 bases in length or greater, and are compatible with the selected expression vector system. Inclusion of the recognition sequence in the primer will result in production of amplification products containing the recognition sequence, so that the DNA produced can be digested with the appropriate enzyme, and readily ligated into the cloning site of the digested vector.

The expression vectors in this embodiment are provided in two formats for antibody expression. The pARC/Fab vector encodes the H and L chains as individual proteins with their own leaders. H and L chain proteins are directed to the periplasmic space following synthesis, where they fold to form dimeric Fab molecules stabilized by inter-chain disulfide bonds. An exemplary vector is illustrated in FIG. 13, Panel A, and is referred to as the pARC/Fab expression vector.

In this embodiment, the expression vector contains, from 5' to 3', a promoter to facilitate expression in a bacterial host cell (exemplified by a lacZ promoter), a ribosome binding site, a first signal sequence (to direct the translated polypeptide to the membrane of the bacterial host), a first cloning site, a first transcriptional stop signal, a second ribosome binding site, a second signal sequence, a second cloning site, an optional detectable label-encoding sequence (exemplified by a His tag) and a second transcriptional stop site. The restriction sites of the first and second cloning sites contain recognition sequences of 8 bases. In general, the first and second cloning sites contain two different restriction sites so as to provide for directional cloning at each of the first and second cloning sites. Thus, the expression cassette usually includes at least four different restriction sites, two for each of the cloning sites, where each of the four restriction sites are for four different restriction enzymes having recognition sequences of 8 bases or longer.

The promoter may be constitutive or inducible, and is generally selected according to the host cell in which the expression vector is to be used. The first and second signal sequences may be the same or different, and may be any suitable signal sequence (e.g., a signal sequence of OmpA, MalE, and the like), which may be selected according to the host cell in which the expression vector is to be used. The detectable label can be any suitable label, with those that facilitate immunodetection and/or immunopurification being of particular interest.

FIG. 13, Panel C illustrates an alternative expression cassette which can provide for dual expression of heavy and light chain polypeptides. In this embodiment, an internal ribosome entry site (IRES) is operably positioned between the two coding sequences so as to facilitate transcription of the heavy and light chain coding sequences as a single mRNA and translation of the encoded sequences from the single mRNA. FIG. 13, Panel C further illustrates an further variation of the expression cassettes in which the expression cassette including operably positioned polynucleotides having sequences encoding a desired light chain leader sequence (LCL), a desired heavy chain leader sequence (HCL), and a desired heavy chain constant region (G1 (CH2CH3)). In this variation, polynucleotides having sequences encoding a desired light chain variable region (composed of the desired CDRs) and a desired heavy chain variable region (composed of the desired CDRs) can be inserted into the vector. The expression vector provided is adapted for expression in a eukaryotic host cell (in contrast to vectors such as pARC/Fab and pARC/SC, which are adapted for expression in a prokaryotic host.

The disclosure also provides an expression vector which allows for expression of Fabs as single chain molecules in which the H and L chains are joined by a flexible linker. An exemplary vector is illustrated in FIG. 13, Panel. B, and is referred to as the pARC/SC vector. Single chain Fabs differ from traditional scFV in that the entire L chain as well as the CH1 region of the heavy chain is synthesized. This latter format avoids problems of unbalanced chain synthesis that may occur in dual expression cassette systems in certain host cells. And, unlike scFvs which are often deposited as inclusion bodies in E coli, a high percentage of Fabs expressed as single chains using this vector are secreted as soluble products into the periplasmic space of the bacterial host, which facilitates screening large expression libraries. The elements of this expression vector are similar to those of the pARC/Fab expression vector described above, except that a linker-encoding sequence is operably inserted between the first and second cloning sites.

The design of the "FAB cassette" (FIG. 13, Panels A and B) in the prokaryotic vector is constructed to facilitate its direct transfer into a eukaryotic expression vector containing the balance of the heavy chain gene sequence. This DNA construct can then be used to transfect eukaryotic cells lines (such as CHO) for the production of antibodies of interest, including heterodimeric, fully human monoclonal antibodies having full-length heavy and light chains, or antigen-binding fragments thereof.

The expression vectors can be introduced into a suitable expression host (e.g., by transfection, lipofection, transformation, etc.) to produce an expression library. Suitable host cell for expression include bacterial cells, such as E. coli, eukaryotic cells, such as CHO cells, and yeast or fungi, such as Saccharomyces (e.g., S. cervesiae) and Pichia (e.g., P. pastoris). Recombinant host cells of the expression library can be cultured under conditions suitable for expression of the encoded polypeptide, e.g., to produce an antibody library, where the antibodies can be enriched for an antigen-binding specificity of interest. The antibodies produced from the expression library may be present intracellularly in the recombinant host cell or, in embodiments of particular interest, secreted into the culture supernatant.

Antigen-binding polypeptides (e.g., antibodies or antigen-binding antibody fragments), having the desired antigen binding specificity can be identified and isolated (including enriched) following expression of the cDNA library. For example, pools of clones or individual clones from such expression libraries can be screened for specific antigen binding. Methods for measuring binding affinity, off rate and other antibody binding kinetics are well known in the art, and may be employed to determine whether an antibody has a high affinity and a slow off rate for an antigen of interest (e.g., PA). In many methods and as is well known in the art, antibody binding kinetics may be measured by ELISA methods or by measuring surface plasmon resonance using, for example, a BIACORE™ biosensor (Pharmacia/Pfizer) or differential scanning calorimetry (Bliznukov et al. 2001 Biochemistry (Mosc) 66:27-33). Methods for measuring binding of antigens to antibodies using surface plasmon resonance are well known in the art (see, e.g., Methods of Dev. Biol. 2003 112: 141-51 and J. Mol. Recognit. 1999 12:310-5) and are readily adapted for use herein.

The method above thus can provide for a library of antigen-binding polypeptides, including whole antibodies or antigen-binding fragments, which bind to an antigen of interest, and can include a range of antibodies that bind the same antigen, but differ in one or more of the epitope bound, binding avidity, binding affinity, or other antibody characteristic. Furthermore, the method can provide for production of a library antigen-binding polypeptides, including whole antibodies or antigen-binding fragments that are representative of a repertoire of antibodies that are generated in response to immunization of a subject with an antigen of interest.

Expression Library of Anti-Anthrax Toxin-Specific Antibodies

The above described method can be used to isolate nucleic acid encoding a library of antibodies that bind an antigen of interest. Anthrax toxin, particularly the protective antigen (PA) of anthrax toxin, is an antigen of interest exemplified herein. It is to be understood while anthrax toxin is exemplified herein, this is not to be limiting as to the antigens to which antibody libraries can be generated using the methods described herein. Rather, the antigen can be any antigen of interest, including full-length polypeptides having a naturally-occurring or non-naturally occurring amino acid sequence, an antigenic fragments of polypeptides, and the like. Antibodies can be produced using the method described above and as further exemplified in the Example section. The following provides a more general description of a method of generating an antibody expression library, with PA as an exemplary antigen.

Mononuclear cells (e.g., from peripheral blood or lymphatic organs) from human or non-human animals exposed to PA in an amount sufficient to elicit an immune response to PA as a result of vaccination or natural exposure are used as a source of mRNA for library procution. The human or non-human donor can be vaccinated with Anthrax Vaccine Adsorbed (AVA, tradename BIOTHRAX®; commercially available from BioPort Corp., Lansing Mich.) or anthrax toxin or a composition useful as an anthrax vaccine, as disclosed in U.S. Pat. Nos. 6,770,479 and 6,387,665, and U.S. Patent Application Pub. Nos. 2005/0112145, 2005/0063986, 2005/0054038, 2004/0018193, 2004/0171121, 2004/0166120, 2004/0076638, and 2004/0009945 (which are incorporated by reference herein in their entirety). In some embodiments, samples for use in mRNA extraction can be enriched for PA-specific B lymphocytes by, for example, using a selection mechanism based on their surface antigen receptor specificity.

The PA-specific B lymphocytes are obtained, mRNA isolated, and cDNA generated from the mRNA. This cDNA then is used as a substrate for nucleic acid amplification to obtain DNA fragments encoding at least the variable regions of heavy and light chain polypeptides. Where the starting cells are from a human source, DNA fragments can be obtained by nucleic acid amplification using a set of H- and L-chain specific primers, particularly those provided in FIGS. 16-17, to provide for amplification of a collection of V gene families, and thus provide for amplification of a wide range of immunoglobulin heavy and light chain fragments. These exemplary primers incorporate restriction sites for restriction enzymes having a recognition sequence of 8 nucleotides, and are compatible with the expression vectors described in more detail below (see expression vectors described in FIG. 13).

Following ligation into an expression vector, the expression vectors are introduced into a suitable host cell (such as *E. coli*) for expression. Individual clones from this expression library are screened for production of PA-binding polypeptides using any of a variety of methods, such as an capture assay or any suitable immunological assay. For example, a suitable capture assay can involve use of an immunoglobulin light chain specific capture antibody (and/or an immunoglobulin heavy chain-specific antibody) immobilized on a substrate (e.g., in a well of a microtiter plate, e.g., a 96 well plate), and incubating the expression products from the library clones (e.g., as cell lysates and/or cell culture supernatants) with the immobilized capture antibody under conditions suitable to provide for specific binding of the capture antibody to the expression products so as to provide for immobilization of expressed antibody fragments (such as Fabs). These captured antibody fragments are then probed using a suitable detectably-labeled PA (such as an $^{125}$I-labeled or enzyme-labeled antigen) to facilitate identification of samples containing antibody fragments that bind PA and thus, in turn to identify those clones that contain a clone that encodes for such an antibody fragment. Clones containing DNA encoding PA-specific binding domains can then be further characterized, e.g., subcloned, antigen-binding characteristics further verified and/or analyzed, and heavy and light chain variable region gene sequences determined using standard molecular biology techniques. The identified clones can then be the basis for further production of PA-binding antibodies or antibody fragments using recombinant techniques. For example, a plasmid can be constructed for introduction into a cell suitable for antibody production (e.g., a eukaryotic cell line (such as CHO), yeast, etc.) and the cell cultured to provide for production of a monoclonal antibody having a desired PA-antigen binding characteristic(s).

In some embodiments, antibodies can be produced using the following procedure: immunoglobulin heavy and light chain mRNA is isolated from circulating B cells collected from humans vaccinated with a PA polypeptide or with an anthrax vaccine, e.g., AVA, anthrax toxin, or a composition useful as an anthrax vaccine as described above. The RNA extract is used to generate a cDNA, which is used as the template for nucleic acid amplification. The primers for use in amplification of cDNA from the RNA extract can be designed to produce amplification products compatible for cloning into an expression vector for expressing the antibody fragments. Exemplary primers particularly suitable for use in the present methods where the cells are obtained from a human source are provided in FIGS. 16 and 17. Exemplary expression cassettes and expression vectors suitable for use with the amplification products produced using these primers are illustrated in FIG. 13. The resulting amplification products are then ligated into expression vectors to produce an expression vector library. The expression vectors, such as those exemplified in FIG. 13, can provide for expression of both the heavy and light chain variable regions from a single construct. The expression vectors of this library are then introduced into a suitable host cell (e.g., *E. coli*) to produce an expression library.

Expression vectors containing DNA amplification products encoding a binding domain specific for the PA of *B. anthracis* are isolated by screening for PA binding of expression products of the expression library (e.g., by use of a selection mechanism based on the surface antigen receptor specificity). These binding domains are then transferred into a suitable expression vector and transfected into a host cell to provide for expression of antibody.

The antibodies can be isolated and tested for a desired function, such as neutralizing activity against *B. anthracis* toxin. Although not intending to be limited by any particular mechanism of action, binding of a neutralizing anti-PA antibody can inhibit (e.g., prevent or reduce) toxin translocation into a cell's cytoplasm at one or more number of different points, e.g., (1) binding of PA to an anthrax toxin receptor (e.g., ATR) on a cell, (2) cleavage of the unprocessed PA83 to the processed PA63 form, (3) formation of a heptamer comprising seven PA63 units, and (4) binding of the toxin to, or otherwise associating with, the heptamer. An anti-PA neutralizing antibody includes those that neutralize anthrax toxin by inhibiting or blocking any one or more of the different points during the pathogenic process through binding to PA. There are two known ATRs (or ANTXR): ANTXR1 (also called ATR/tumor endothelial marker 8; ATR/TEM8) and ANTXR2 (also called capillary morphogenesis gene 2; CMG2). The PA activity is "neutralized", or the antibody is "neutralizing", in any of a variety of ways, including, for example: when binding of the subject antibody to PA inhibits (e.g., prevents or reduces) one or more of the following: (1) PA from binding to a cell surface receptor (e.g., ANTXR1 and/or ANTXR2), (2) protease mediated cleavage of PA into PA20 and PA63 (3) PA from forming a heptamer, (4) internalization of EF and/or LF, (5) EF and/or LF from disabling host innate and/or adaptive immune response, (6) EF- and/or LF-mediated vascular leakage, and (7) *B. anthracis*-mediated cell death.

In vitro assays for determining whether an antibody can neutralize anthrax toxin are well known in the art. Such activity of an antibody can be determined, e.g., by a toxin neutralization assay (TNA, an exemplary TNA is described in Little et al., *Infection and Immunity* 58: 1606-1613 (1990) in which a toxin-sensitive macrophage cell line J774A.1 is exposed to mixtures of LF and PA in the presence of a PA-specific antibody where antibody-mediated neutralization of the toxin results in increased survival of the macrophages; Little et al., *Biochem. Biophys. Res. Commun.* 199: 676-82 (1994); and Little et al., *Microbiol.* 142: 707-715 (1996) (which are incorporated by reference herein in their entirety). In performing a TNA to determine the effectiveness of an antibody, the effective dose (ED) for an antibody capable of achieving 50% ($ED_{50}$) cell viability is measured. PA-specific antibodies useful in the present invention include those which can effect neutralization anthrax toxin in concentrations of less than 5 µg/ml, less than 1 µg/ml, or less than 0.1 µg/ml. Thus, antibodies have an $ED_{50}$ of from about 0.001 to 5 µg/ml, 1 µg/ml or less, or 0.1 µg/ml or less, as measured by TNA.

This method thus can provide antibodies that are fully human monoclonal antibodies which have a desired antigen binding specificity (here exemplified by anti-PA binding) and, where desired, function (e.g., neutralization). The cDNA encoding the antibodies can be sequenced and the nucleotide and predicted amino acid sequences of their respective CDRs, $V_H$ regions, $V_L$ regions, heavy chains and light chains can be determined.

Antibodies that Specifically Bind Protective Antigen (PA)

The present disclosure provides isolated antibodies that specifically bind PA (which includes antigen-binding fragments thereof), where the antibodies are characterized in that they comprise the amino acid sequence of a complementarity determining region (CDR) (e.g., at least one or more of, usually all three of a CDR1, CDR2 or CDR3), of a heavy chain polypeptide and/or light chain polypeptide of an antibody having the designation 1A5, 4A12, 24B1, 24G4, 32E12, or 33F4 (see FIGS. 1-12) and/or compete with such an antibody for specific binding to PA, wherein, wherein the antibody is capable of binding to or neutralizing protective antigen (PA) of *B. anthracis*. Antibodies that compete for specific binding to PA with an anti-PA binding antibody such as an antibody having the designation 1A5, 4A12, 24B1, 24G4, 32E12, or 33F4 can be accomplished according to methods well known in the art. For example, an antibody having a desired PA binding activity can be detectably labeled (e.g., by conjugation to biotin) and the ability of candidate antibodies to compete for binding to PA evaluated by their capacity to compete with the binding of detectably labeled antibody to PA in solution and/or immobilized on a surface (e.g., as on a sepharose bead). The binding of detectably labeled anti-PA antibody in the presence of candidate antibodies is assessed, where a decrease in detectably labeled anti-PA antibody in the presence of a candidate anti-PA antibody indicates the candidate antibody competes for binding with the anti-PA antibody for an epitope of PA. Candidate antibodies can be further screened for neutralizing activity according to methods known in the art, such as the assays exemplified herein.

In some embodiments the antigen-binding polypeptide comprises the contiguous amino acid sequences of the CDRs (CDR1, CDR2, and CDR2) of the heavy and light chain polypeptides of 1A5, 4A12, 24B1, 24G4, 32E12, or 33F4, and may further comprise the contiguous framework sequences of the heavy and light chain polypeptides of 1A5, 4A12, 24B1, 24G4, 32E12, or 33F4, or may have a variant amino acid sequence relative to the heavy and light chain polypeptides of 1A5, 4A12, 24B1, 24G4, 32E12, or 33F4, particularly where the amino acid sequence contains modifications relative to the parent amino acid sequence in a region of the amino acid sequence other than the CDR. Also encompassed are antigen-binding fragments comprising at least the variable regions of the heavy and light polypeptides of the antibody 1A5, 4A12, 24B1, 24G4, 32E12, or 33F4. For convenience, reference to "anti-PA monoclonal antibodies" or "anti-PA mAbs" is meant to encompass the antibodies 1A5, 4A12, 24B1, 24G4, 32E12, and 33F4, as well as modified versions thereof as described in detail herein, which modified antibodies exhibit the PA binding specificity of 1A5, 4A12, 24B1, 24G4, 32E12, or 33F4.

Isolated antibodies having amino acid sequences substantially identical to the amino acid sequence of anti-PA mAbs described herein are also contemplated, e.g., antibodies having a contiguous amino acid sequence of a full-length variable region of a heavy chain or light chain polypeptide of an anti-PA mAb. Thus, the disclosure contemplatese polypeptides and antibodies comprising one or more of the following amino acid sequences: SEQ ID NOs: 1-60, with amino acid sequences of CDRs are indicated in FIGS. 1-12 being of particular interest.

Thus, as is evident above, the disclosure provides antibodies having the PA-binding characteristic(s) of an anti-PA mAb disclosed herein. In certain embodiments a recombinant monoclonal antibody having a antigen-binding characteristics of anti-PA mAb has a heavy chain having an amino acid sequence that is substantially identical (e.g., at least about 80%, at least about 85%, at least about 90%, at least about 95% or at least about 98% identical) to that of the contiguous sequence of the anti-PA mAb heavy chain variable domain, and a light chain that is substantially identical (e.g., at least about 80%, at least about 85%, at least about 90%, at least about 95% or at least about 98% identical) to the contiguous sequence of an anti-PA mAb light chain variable domain. In particular embodiments, a recombinant antibody has framework or CDR amino acid sequences that are substantially identical (e.g., at least about 80%, at least about 85%, at least about 90%, at least about 95% or at least about 98% identical) to a contiguous framework sequence or a contiguous CDR sequence of any of the heavy or light chain sequences shown in FIGS. 1-12. Such polypeptides are useful in constructing chimeric antibodies having antigen-binding specificity of an anti-PA mAb. Such contiguous sequences can include the CDRs of the light chain polypeptides (L-CDR1, L-CDR2, L-CDR3) and/or heavy chain polypeptides (H-CDR1, H-CDR2, H-CDR3).

In certain embodiments, recombinant monoclonal antibodies contain a heavy or light chain that is encoded by a polynucleotide that hybridizes under high stringency conditions to a full length anti-PA heavy or light chain-encoding nucleic acid. High stringency conditions include incubation at 50° C. or higher in 0.1×SSC (15 mM saline/0.15 mM sodium citrate).

In certain embodiments, recombinant monoclonal antibodies may contain a heavy or light chain that is encoded by a polynucleotide having a nucleotide sequence that is at least 80% identical to (e.g., at least 85%, at least 90%, at least 95%, at least 98%) to a contiguous sequence of a anti-PA heavy or light chain-encoding nucleic acid. The percentage identity is based on the shorter of the sequences compared. Well known programs such as BLASTN (2.0.8) (Altschul et al. (1997) *Nucl. Acids. Res.* 25:3389-3402) using default parameters and no filter may be employed to make a sequence comparison.

The recombinant monoclonal antibody may be a full-length antibody or any chimera thereof, for example. Methods for producing chimeric antibodies are known in the art. See e.g., Morrison et al (Science 1985 229:1202); Oi et al (BioTechniques 1986 4:214); Gillies et al. (J. Immunol. Methods 1989 125:191-202) and U.S. Pat. Nos. 5,807,715, 4,816,567 and 4,816,397, which are incorporated herein by reference in their entirety.

The amino acid sequences of the CDRs of the heavy and light chains of anti-PA are provided in FIGS. 1-12, with the framework and CDR regions indicated for anti-PA light and heavy chains.

The present disclosure also provides polypeptides comprising the amino acid sequence at least one of CDR1, CDR2 and CDR3 of a heavy chain anti-PA mAb disclosed herein as well as polypeptides comprising the amino acid sequence of at least one of CDR1, CDR2 and CDR3 of a light chain of anti-PA mAb disclosed herein. In some embodiments, the isolated polypeptide comprises the amino acid sequences of the $V_H$ region of a heavy chain or the $V_L$ region of a light chain of an anti-PA mAb. When provided as a heterodimer of heavy and light chains (as in a FAb) or as a combination of heterodimers (as in a whole antibody), the heterodimer may be composed of heavy chain and light chain derived from the same or different, usually the same, anti-PA antibody.

The present disclosure provides for an isolated anti-PA antibody that is of any isotype, such as, IgG, IgM, IgA, IgD, or IgE. In some embodiments, the antibody is glycosylated, and may be hyperglycosylated (e.g., through introduction of glycosylation sites). In certain embodiments, the antibody comprises a glycosylation pattern that is normal for an antibody expressed from a human cell.

The antigen-binding portions of the anti-PA antibodies can be used to generate chimeric antibodies of any desired isotype or having any desired function (e.g., a detectable label, etc.). As used herein, "isotype" refers to the antibody class (e.g., IgM or IgG1) that is conferred by a heavy chain constant region. An isolated antibody can be of any antibody isotype, e.g., IgG1, IgG2, IgG3, IgG4, IgM, IgA1, IgA2, secretory IgA, IgD, and IgE.

The anti-PA antibodies can also be provided with different glycosylation patterns, e.g., unglycosylated, partially glycosylated, or fully or hyperglycosylated forms. As used herein, "glycosylation pattern" refers to a co-translational and/or post-translational modification of an antibody produced whereby a pattern of carbohydrate units is covalently attached to the antibody by the host cell in which the antibody is produced. Different host cells can produce different glycosylation patterns. Specific glycosylations includes N-linked glycosylation to the amide nitrogen of an asparagine side chain and O-linked glycosylation to the hydroxy oxygen of a serine or threonine side chain. For example, an antibody produced in a eukaryotic cell, e.g., a CHO cell, would have a glycosylation pattern. As most bacterial species naturally do not glycosylate protein, an antibody produced in such a bacterial host cell, e.g., *E. coli*, would have no "glycosylation pattern".

Bispecific antibodies, humanized antibodies, mutant antibodies, and the like having amino acid sequences comprising one or more of the CDRs of the anti-PA mAbs are also contemplated. In some embodiments, the bispecific antibodies, mutant antibodies, and the like have an amino acid sequence that comprises the three CDRs of the antibodies 1A5, 4A12, 24B1, 24G4, 32E12, or 33F4. In certain embodiments, the bispecific antibodies, mutant antibodies, and the like that have an amino acid sequence that comprises the $V_H$ region and/or the $V_L$ region of the antibodies 1A5, 4A12, 24B1, 24G4, 32E12, or 33F4.

In certain embodiments, human monoclonal antibodies to PA, or antigen-binding fragments thereof, can be derivatized or linked to another functional molecule, e.g., another antibody fragment (e.g., an Fab' fragment) to generate a bispecific or multispecific molecule which binds to multiple binding sites or target epitopes. For example, an antibody or antigen-binding portion can be functionally linked (e.g., by chemical coupling, genetic fusion, noncovalent association or otherwise) to one or more other binding molecules, such as another antibody or antibody fragment.

As used herein, the term "multispecific antibody", also referred to as a "diabody", includes an antibody, or antigen-binding fragment thereof, comprising two or more different binding specificities. For example, the molecule may bind to, or interact with, (a) a first PA epitope and (b) a second PA epitope, and/or (c) a third PA epitope. Alternatively or in addition, the multispecific antibody may bind to a PA epitope and to an antigen other than PA. Multispecific antibodies thus encompass bispecific, trispecific, tetraspecific, and other multispecific molecules which are directed to antigens. For example, a bispecific antibody comprises two antigen-binding sites, which fragments comprise a heavy chain variable domain ($V_H$) connected to a light chain variable domain ($V_L$) in the same polypeptide chain ($V_H$-$V_L$). By using a linker that is too short to accommodate efficient pairing between the two domains on the same chain, the domains predominately pair with the complementary domains of another chain and create two antigen-binding sites.

The disclosure also provides antibodies that are modified by conjugation to a moiety that can provide for a desired characteristic (e.g., increase in serum half-life, anthrax toxin neutralizing activity, etc.). Such antibody conjugates are exemplified below.

Modified Antibodies Having Antigen Binding Specificity of an Anti-PA mAb

The above-described recombinant monoclonal antibodies having an antigen binding region of anti-PA mAb may be modified to provide modified antibodies that bind a PA epitope, and have a desired activity, e.g., anthrax toxin neutralizing activity, enhanced serum half-life, reduced immunogenicity, and the like. The modified antibodies may be made by substituting, adding, or deleting at least one amino acid of an above-described anti-PA mAb. In one embodiment, the anti-PA mAb is modified to provide a humanized antibody for human therapeutic use, or another type of modified antibody. In general, these modified antibodies have the general antigen-binding characteristics of the anti-PA mAb, and contain at least the CDRs of a anti-PA mAb heavy chain polypeptide and an anti-PA mAb light chain polypeptide.

Guidance for amino acid substitutions that may be made can be found in the accompanying FIGS. 1-12 and 19, which illustrate the sequences and positions of the CDRs in the heavy and light chain polypeptides of anti-PA mAbs. For example, in some embodiments, variants can be generated by making amino acid changes (e.g., substitutions, particularly conservative amino acid substitutions) in the areas outside the CDRs so identified. Further guidance for amino acid substitutions can be found by aligning the amino acid sequences of other anti-PA epitope antibodies with that of anti-PA mAbs, and noting regions that are conserved or variable, and making changes in the variable regions that lie outside the CDRs.

In particular embodiments, these methods include making one or more amino acid substitutions (e.g., one, up to two, up to three, up to four or up to five of more, usually up to 10 or more). An amino acid substitution may be at any position, and the amino acid at that position may be substituted by an amino acid of any identity. A modified antibody has the same general characteristics of the anti-PA mAb. In one embodiment, after a substitutable position has been identified by alignment of the sequences provided herein with the sequences of other antibodies, the amino acids at that position may be substituted. In particular embodiments, an amino acid substitution may be a humanizing substitution (e.g., a substitution that make the amino acid sequence more similar to that of a human antibody, particularly an anti-PA mAb), a directed substitution (e.g., a substitution that make the amino acid sequence of an antibody more similar to that of a related antibody in the same group), a random substitution (e.g., a substitution with any of the 20 naturally-occurring amino acids) or a conservative substitution (e.g., a substitution with an amino acid having biochemical properties similar to that being substituted).

In certain embodiments, modified antibodies may contain a heavy or light chain that is encoded by a polynucleotide that hybridizes under high stringency conditions to a anti-PA mAb heavy or light chain-encoding nucleic acid, particularly to the fragments encoding CDR1, CDR2 and CDR3 of the variable region of an anti-PA mAb light chain polypeptide and to fragments encoding CDR1, CDR2, and CDR3 of the variable region of an anti-PA mAb heavy chain polypeptide. High stringency conditions include incubation at 50° C. or higher in 0.1×SSC (15 mM saline/0.15 mM sodium citrate).

In certain embodiments, modified antibodies of the invention may contain a heavy or light chain that is encoded by a polynucleotide that is at least 80% identical to (e.g., at least 85%, at least 90%, at least 95%, at least 98%) a contiguous anti-PA mAb heavy or light chain-encoding nucleic acid. The percentage identity is based on the shorter of the sequences compared. Well known programs such as BLASTN (2.0.8) (Altschul et al. (1997) *Nucl. Acids. Res.* 25:3389-3402) using default parameters and no filter may be employed to make a sequence comparison.

Polyethylene Glycol (PEG)-Modified Antibodies

Anti-PA antibodies contemplated herein include PEGylated anti-PA antibodies, with PEGylated recombinant anti-PA antibodies having antigen specificity of anti-PA mAb being of particular interest. Methods and reagents suitable for PEGylation of an antibody are well known in the art. In general, PEG suitable for conjugation to an antibody is generally soluble in water at room temperature, and has the general formula R(O—CH$_2$—CH$_2$)$_n$O—R, where R is hydrogen or a protective group such as an alkyl or an alkanol group, and where n is an integer from 1 to 1000. Where R is a protective group, it generally has from 1 to 8 carbons.

In many embodiments, PEG has at least one hydroxyl group, e.g., a terminal hydroxyl group, which hydroxyl group is modified to generate a functional group that is reactive with an amino group, e.g., an epsilon amino group of a lysine residue, a free amino group at the N-terminus of a polypeptide, or any other amino group such as an amino group of asparagine, glutamine, arginine, or histidine.

In other embodiments, PEG is derivatized so that it is reactive with free carboxyl groups in the antibody polypeptide, e.g., the free carboxyl group at the carboxyl terminus of the antibody polypeptide. Suitable derivatives of PEG that are reactive with the free carboxyl group at the carboxyl-terminus of a heavy chain or light chain polypeptide include, but are not limited to PEG-amine, and hydrazine derivatives of PEG (e.g., PEG-NH—NH$_2$).

In other embodiments, PEG is derivatized such that it comprises a terminal thiocarboxylic acid group, —COSH, which selectively reacts with amino groups to generate amide derivatives. Because of the reactive nature of the thio acid, selectivity of certain amino groups over others is achieved. For example, —SH exhibits sufficient leaving group ability in reaction with N-terminal amino group at appropriate pH conditions such that the $\epsilon$-amino groups in lysine residues are protonated and remain non-nucleophilic. On the other hand, reactions under suitable pH conditions may make some of the accessible lysine residues to react with selectivity.

In other embodiments, the PEG comprises a reactive ester such as an N-hydroxy succinimidate at the end of the PEG chain. Such an N-hydroxysuccinimidate-containing PEG molecule reacts with select amino groups at particular pH conditions such as neutral 6.5-7.5. For example, the N-terminal amino groups may be selectively modified under neutral pH conditions. However, if the reactivity of the reagent were extreme, accessible-NH$_2$ groups of lysine may also react.

The PEG can be conjugated directly to an amino acid residues of the antibody, or through a linker. In some embodiments, a linker is added to an antibody polypeptide, forming a linker-modified antibody polypeptide. Such linkers provide various functionalities, e.g., reactive groups such sulfhydryl, amino, or carboxyl groups to couple a PEG reagent to the linker-modified antibody polypeptide.

In some embodiments, the PEG conjugated to the antibody polypeptide is linear. In other embodiments, the PEG conjugated to the antibody polypeptide is branched. Branched PEG derivatives such as those described in U.S. Pat. No. 5,643,575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

PEG having a molecular weight in a range of from about 2 kDa to about 100 kDa, is generally used, where the term "about," in the context of PEG, indicates that in preparations of polyethylene glycol, some molecules will weigh more, some less, than the stated molecular weight. For example, PEG suitable for conjugation to antibody has a molecular weight of from about 2 kDa to about 5 kDa, from about 5 kDa to about 10 kDa, from about 10 kDa to about 15 kDa, from about 15 kDa to about 20 kDa, from about 20 kDa to about 25 kDa, from about 25 kDa to about 30 kDa, from about 30 kDa to about 40 kDa, from about 40 kDa to about 50 kDa, from about 50 kDa to about 60 kDa, from about 60 kDa to about 70 kDa, from about 70 kDa to about 80 kDa, from about 80 kDa to about 90 kDa, or from about 90 kDa to about 100 kDa.

Preparing PEG-Antibody Conjugates

As discussed above, the PEG moiety can be attached, directly or via a linker, to an amino acid residue at or near the N-terminus, internally, or at or near the C-terminus of the antibody polypeptide. Conjugation can be carried out in solution or in the solid phase.

N-Terminal Linkage

Methods for attaching a PEG moiety to an amino acid residue at or near the N-terminus of an antibody polypeptide are known in the art. In some embodiments, known methods for selectively obtaining an N-terminally chemically modified antibody are used. For example, a method of protein modification by reductive alkylation which exploits differential reactivity of different types of primary amino groups (lysine versus the N-terminus) available for derivatization in a particular protein can be used. Under the appropriate reaction conditions, substantially selective derivatization of the protein at the N-terminus with a carbonyl group containing polymer is achieved. The reaction is performed at pH which allows one to take advantage of the $pK_a$ differences between the $\epsilon$-amino groups of the lysine residues and that of the $\alpha$-amino group of the N-terminal residue of the protein. By such selective derivatization attachment of a PEG moiety to the antibody is controlled: the conjugation with the polymer takes place predominantly at the N-terminus of the antibody and no significant modification of other reactive groups, such as the lysine side chain amino groups, occurs.

C-Terminal Linkage

MonoPEGylation can be accomplished by using a PEG reagent that is selective for the C-terminus of a polypeptide, which can be prepared with or without spacers. For example, polyethylene glycol modified as methyl ether at one end and having an amino function at the other end may be used as the starting material.

Preparing or obtaining a water-soluble carbodiimide as the condensing agent can be carried out. Coupling antibody with a water-soluble carbodiimide as the condensing reagent is generally carried out in aqueous medium with a suitable buffer system at an optimal pH to effect the amide linkage. A high molecular weight PEG can be added to the protein covalently to increase the molecular weight.

The reagents selected will depend on process optimization studies. A non-limiting example of a suitable reagent is EDC or 1-ethyl-3-(3-dimethylaminopropyl)carbodiimide. The water solubility of EDC allows for direct addition to a reaction without the need for prior organic solvent dissolution.

Even though the use of PEG amine has been mentioned above by name or structure, such derivatives are meant to be exemplary only, and other groups such as hydrazine derivatives as in PEG-NH—$NH_2$ which will also condense with the carboxyl group of the antibody protein, can also be used. In addition to aqueous phase, the reactions can also be conducted on solid phase. Polyethylene glycol can be selected from list of compounds of molecular weight ranging from 300-40000. The choice of the various polyethylene glycols will also be dictated by the coupling efficiency and the biological performance of the purified derivative in vitro and in vivo i.e., circulation times, anti viral activities etc.

Additionally, suitable spacers can be added to the C-terminal end of the antibody heavy chain and/or light chain protein. The spacers may have reactive groups such as SH, $NH_2$ or COOH to couple with appropriate PEG reagent to provide the high molecular weight Antibody derivatives. A combined solid/solution phase methodology can be devised for the preparation of C-terminal pegylated antibody polypeptides.

If desired, PEGylated antibody is separated from unPEGylated antibody using any known method, including, but not limited to, ion exchange chromatography, size exclusion chromatography, and combinations thereof.

Antibody-Fusion Proteins

The invention also contemplates recombinant antibodies having the antigen specificity of a anti-PA mAb, where the antibody is modified to include a heterologous protein. For example, a anti-PA mAb heavy chain polypeptide or anti-PA mAb light chain polypeptide may be joined to a reporter protein or to a protein having a desired anti-bacterial effect. In one embodiment, the invention provides a CDR of an anti-PA mAb light chain polypeptide or a CDR of a heavy chain anti-PA mAb polypeptide which is linked to a heterologous polypeptide, i.e., is linked to a polypeptide to which it is not normally associated in the native anti-PA mAb. Methods for producing a fusion protein of interest when provided a nucleic acid sequence are well known in the art.

Anti-PA Antibody Libraries

The present invention also provides for a library of antibodies, comprising one or more of the anti-PA mAbs disclosed herein. In some embodiments, the library comprises 2, 3, 4, 5, 6, 10, 15, 20 or more different antibodies or antigen binding fragments having anti-PA binding characteristics of the anti-PA mAbs disclosed herein. In certain embodiments, the library is provided as an array wherein the array can be used in, for example, methods for detection of PA in a sample as well as in screening methods to identify peptides (e.g., synthetic peptides) or molecules that specifically bind to these mAbs (which can in turn be useful to elicit an antibody response that would result in production of antibodies that bind the PA epitope bound by the anti-PA mAbs disclosed herein).

Nucleic Acids Encoding the Polypeptides or Antibodies

The present disclosure also provides isolated or recombinant nucleic acid comprising a nucleotide sequence encoding an anti-PA mAb and related polypeptides described herein. In some embodiments, the isolated or recombinant nucleic acid comprises a nucleotide sequence encoding the polypeptide that is operably linked to a promoter, wherein the antibody is capable of expression in a host cell. The invention also provides for vectors comprising the nucleic acid described herein.

In certain embodiments the polynucleotide encodes a polypeptide having an amino acid sequence that is substantially identical (e.g., at least about 80%, at least about 85%, at least about 90%, at least about 95% or at least about 98% identical) to that of the contiguous sequence of the anti-PA mAb heavy chain variable domain, and/or encodes a light chain polypeptide that is substantially identical (e.g., at least about 80%, at least about 85%, at least about 90%, at least about 95% or at least about 98% identical) to the contiguous sequence of an anti-PA mAb light chain variable domain. In particular embodiments, a recombinant polynucleotide encodes a polypeptide comprising framework or CDR amino acid sequences that are substantially identical (e.g., at least about 80%, at least about 85%, at least about 90%, at least about 95% or at least about 98% identical) to a contiguous framework sequence or a contiguous CDR sequence of any of the heavy or light chain sequences shown in FIGS. 1-12. Such contiguous sequences can include those encoding the CDRs of the light chain polypeptides (L-CDR1, L-CDR2, L-CDR3) and/or heavy chain polypeptides (H-CDR1, H-CDR2, H-CDR3).

In some embodiments, the nucleic acid comprises a nucleotide sequence encoding a polypeptide having an amino acid sequence of any of SEQ ID NOs: 1-60. In certain embodiments, the nucleic acid comprises a nucleotide sequence of any of SEQ ID NOs: 61-72.

Nucleic acid compositions of particular interest comprise a sequence of DNA having an open reading frame (ORF) that encodes a polypeptide or antibody and is capable, under appropriate conditions, of being expressed and transport of the polypeptide or antibody out of the host cell. Also encompassed in this term are nucleic acids that are homologous, substantially similar or identical to the nucleic acids disclosed herein.

The polynucleotides and constructs thereof can be generated synthetically by a number of different protocols known to those of skill in the art. Appropriate polynucleotide constructs are purified using standard recombinant DNA techniques as described in, e.g., Sambrook et al., *Molecular Cloning: A Laboratory Manual, 2nd Ed.*, (1989) Cold Spring Harbor Press, Cold Spring Harbor, N.Y., and under current regulations described in U.S. Dept. of HHS, National Institute of Health (NIH) Guidelines for Recombinant DNA Research, which are incorporated by reference herein in their entirety.

Also provided are constructs comprising the nucleic acids described herein inserted into a vector, where such constructs may be used for the expression of the polypeptides and antibodies of this invention. In some embodiments, a single vector (e.g., a plasmid) will contain nucleic acid coding sequence for a polypeptide or antibody.

Also provided are expression cassettes or systems that find use in, among other applications, the synthesis of the polypeptides or antibodies. For expression, the polypeptide or antibody encoded by a polynucleotide is expressed in any convenient expression system, including, e.g., bacterial, yeast, insect, amphibian and mammalian systems. In the expression vector, a polynucleotide is linked to a regulatory sequence as appropriate to obtain the desired expression properties. These regulatory sequences can include promoters (attached either at the 5' end of the sense strand or at the 3' end of the antisense strand), enhancers, terminators, operators, repressors, and inducers. The promoters can be regulated or constitutive. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the species from which the nucleic acid is obtained, or may be derived from exogenous sources. Expression vectors of particular interest are those described herein, and illustrated in FIG. 13.

Promoters may be either constitutive or regulatable. Inducible elements are DNA sequence elements that act in conjunction with promoters and may bind either repressors (e.g. lacO/LAC Iq repressor system in *E. coli*) or inducers (e.g. gall/GAL4 inducer system in yeast). In such cases, transcription is virtually "shut off" until the promoter is derepressed or induced, at which point transcription is "turned-on".

Expression vectors generally have convenient restriction sites located near the promoter sequence to provide for the insertion of nucleic acid sequences encoding heterologous proteins. A selectable marker operative in the expression host may be present. Expression cassettes may be prepared comprising a transcription initiation region, the gene or fragment thereof, and a transcriptional termination region. After introduction of the DNA, the cells containing the construct may be selected by means of a selectable marker, the cells expanded and then used for expression.

Methods of Producing Anti-PA mAbs

Methods of producing an antibody described herein generally involve culturing a host cell described herein under conditions whereby the antibody is expressed. The antibodies can be produced by a variety of techniques, including conventional monoclonal antibody methodology, see, e.g., Harlow et al., *Using Antibodies—A Laboratory Manual*, Cold Spring Harbor Lab. Press, Cold Spring Harbor, N.Y. (1999).

Expression Systems and Host Cells

As will be appreciated by those in the art, the type of host cells suitable for use can vary widely. In some embodiments, the host cell is a bacterial cell, a yeast cell or a mammalian cell. In certain embodiments, the host cell is a bacterial cell, such as *E. coli*. In certain embodiments, the host cell is a yeast cell, such as a *Saccharomyces* or *Pichia* cell. In certain embodiments, the host cell is a eukaryotic cell. In certain embodiments, the host is a mammalian cell, such as a cell from a mouse, rat, rabbit, primate or human. Suitable cells include known research cells, including, but not limited to, Jurkat T cells, NIH3T3 cells, CHO, Cos, etc.

The above described expression systems may be employed with prokaryotes or eukaryotes in accordance with conventional ways, depending upon the purpose for expression. In some embodiments, a unicellular organism, such as *E. coli, B. subtilis, S. cerevisiae, Pichia*, insect cells in combination with baculovirus vectors, or cells of a higher organism such as vertebrates, e.g., COS 7 cells, HEK 293, CHO, *Xenopus* Oocytes, or the like, may be used as the expression host cells. In other situations, it is desirable to use eukaryotic cells, where the expressed protein will benefit from native folding and post-translational modifications, including glycosylation.

In general, any suitable host cell, vector and promoter can be used in connection with the anti-PA-encoding nucleic acids of the invention. Of particular interest are vectors having an insert encoding at least a CDR of a anti-PA mAb heavy chain polypeptide and/or at least a CDR of a anti-PA mAb light chain polypeptide, with expression vectors that provide for expression of both a anti-PA mAb heavy and light chain polypeptide from a single vector being of particular interest, including those exemplified in FIG. 13. It should be noted that while FIG. 13 illustrates the light chain coding sequence is positioned 5' of the heavy chain coding sequence, vectors having the heavy chain coding sequence 5' of the light chain coding sequence are also contemplated.

Any cell suitable for expression of expression cassettes may be used as a host cell. For example, yeast, insect, plant, etc., cells. In many embodiments, a mammalian host cell line that does not naturally produce antibodies, e.g., mammalian cells that are not hybridoma cells, B cells, or spleen cells. It may also be of interest to use cells that provide for altered glycosylation of the recombinant antibody, or which lack glycosylation. Exemplary cells include, but are not limited to: monkey kidney cells (COS cells), monkey kidney CVI cells transformed by SV40 (COS-7, ATCC CRL 165 1); human embryonic kidney cells (HEK-293); baby hamster kidney cells (BHK, ATCC CCL 10); chinese hamster ovary-cells (CHO); mouse sertoli cells (TM4); monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TRI cells (Mather et al., Annals N.Y. Acad. Sci 383:44-68 (1982)); NIH/3T3 cells (ATCC CRL-1658); and mouse L cells (ATCC CCL-1). Additional cell lines will be readily apparent to those of ordinary skill in the art upon reading the present disclosure.

For long-term, high-yield production of recombinant antibodies, stable expression may be used. For example, cell lines, which stably express the antibody molecule may be engineered. Rather than using expression vectors which contain viral origins of replication, host cells can be transformed with immunoglobulin expression cassettes and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into a chromosome and grow to form foci which in turn can be cloned and expanded into cell lines. Such engineered cell lines may be particularly useful in screening and evaluation of compounds that interact directly or indirectly with the antibody molecule.

Methods of introducing nucleic acids into cells are well known in the art. Suitable methods include electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995. In some embodiments lipofectamine and calcium mediated gene transfer technologies are used.

After the subject nucleic acids have been introduced into a cell, the cell is typically incubated, normally at 37° C., sometimes under selection, for a period of about 1-24 hours in order to allow for the expression of the antibody. In embodiments of particular interest, the antibody is typically secreted into the supernatant of the media in which the cell is cultured.

Antibody Isolation

Once a recombinant antibody molecule of the invention has been produced, it may be isolated and, where desired, purified by any suitable method known in the art. Exemplary methods include chromatography (e.g., ion exchange, affinity, particularly by affinity for the specific antigen after Protein A, and sizing column chromatography), centrifugation, differential solubility, or by any other standard technique for the purification of proteins. In many embodiments, antibodies are secreted from the cell into culture medium and harvested from the culture medium.

In general, antibody expressed from a host cell is isolated from either the periplasmic space (e.g., in bacterial hosts) or the surrounding growth medium. The location of the expressed protein is dependent on the particular strain utilized as the host. For example, *E. coli* strains which show high levels of excretion are strains MC1061, JM103 and 706.

Where the antibody is isolated from the periplasmic space, the cell wall may be penetrated to provide for release of the proteins without disruption of the cytoplasmic membrane. One technique of removal of periplasmic proteins is that originally described by Zinder et al., *Proc. Natl. Acad. Sci. USA* 42:586-590 (1956), which involves removal of the cell wall. Periplasmic proteins may also be isolated by a mechanism which does not require removal of the cell wall, but instead causes release of the polypeptides or antibodies. Cells are placed in a hypertonic sucrose medium containing EDTA; this medium causes the cells to lose water and shrink, so that the cytoplasmic membrane draws away from the cell wall. The cells are then placed in a magnesium chloride solution which induces an osmotic shock: the osmotic pressure outside the cell decreases, causing water to rush into the cell, which swells the cell and causes the expulsion of periplasmic proteins beyond the outer membrane. Variations in the foregoing procedures will be readily apparent to one skilled in the art.

Pharmaceutical Compositions

The present disclosure also provides for a pharmaceutical composition comprising any of the antibodies described herein (such as, the human anti-PA mAbs 1A5, 4A12, 24B1, 24G4, 32E12, or 33F4) and a pharmaceutically acceptable carrier. Pharmaceutical compositions can be provided as substantially free from any etiologic agents, infectious agents (particularly those infectious for the subject to which the composition is to be administered, e.g., a human), human blood components, and the like. In some embodiments the antibodies, and pharmaceutical compositions comprising thereof, are substantially free from any contaminants normally found in a mammalian or bacterial cell extract or preparations.

The pharmaceutical composition can optionally further comprising an additional therapeutic agent. The additional therapeutic agent is selected from an antibiotic, a PA vaccine, or a second antibody, wherein the second antibody binds to *B. anthracis*, *B. anthracis* spores, or anthrax toxin, or fragment thereof, such as PA, LF or EF. In some embodiments, the compositions include a combination of multiple (e.g., two or more) isolated human anti-PA antibodies, or antigen-binding fragments thereof. In certain embodiments, each of the antibodies, or antigen-binding fragments thereof, binds to a distinct, pre-selected epitope of PA.

As used herein, "pharmaceutically acceptable carrier" includes any and all any suitable substances which provide a pharmaceutically acceptable vehicle for administration of a compound(s) of interest to a subject (e.g., an antibody). "As such, pharmaceutically acceptable excipients can comprise solvents, dispersion media, coatings, antibacterial and antifungal agents, isotonic and absorption delaying agents, and the like that are physiologically compatible. In some embodiments, the carrier is suitable for intravenous, intramuscular, subcutaneous, parenteral, spinal or epidermal administration (e.g., by injection or infusion). Depending on the route of administration, the active compound, e.g, antibody, bispecific and multispecific molecule, may be coated in a material to protect the compound from the action of acids and other natural conditions that may inactivate the compound. Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions is contemplated. Supplementary active compounds can also be incorporated into the compositions.

Actual dosage levels of the antibodies in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the antibody employed in the pharmaceutical composition at levels lower than that required in order to achieve the desired therapeutic effect and gradually increase the dosage until the desired effect is achieved. In general, a suitable daily dose of a composition will be that amount of the compound which is the lowest dose effective to produce a therapeutic effect. Such an effective dose will generally depend upon the factors described above.

Any mode of parenteral administration is suitable for use in the present invention. Administrations include intravenous, intramuscular, intraperitoneal, or subcutaneous, or administered proximal to the site of the target. If desired, the effective daily dose of a therapeutic composition may be administered as two, three, four, five, six or more sub-doses administered separately at appropriate intervals throughout the day, optionally, in unit dosage forms. The antibody of the present invention can be administered alone or in a pharmaceutical formulation.

The term "therapeutically effective" in reference to dose of an antibody means an amount of the antibody which reduces a sign or a symptom associated with anthrax infection or anthrax toxin toxicity by at least about 20%, about 40%, about 60%, or by at least about 80%, or by complete reduction relative to untreated subjects. In some embodiments, a therapeutically effective amount of an antibody is an amount sufficient to prevent death in a subject exposed to anthrax. The ability of an antibody to reduce signs and/or symptoms, including preventing death, associated with anthrax infection can be evaluated in an animal model system predictive of efficacy of the antibody in treating human anthrax infection.

Alternatively, a therapeutically effective amount of an antibody can be evaluated by examining the antibody's ability to neutralize an anthrax toxin in vitro in a toxin neutralization assay, which is well known in the art and described supra. One of ordinary skill in the art would be able to determine such therapeutically effective amounts based on factors such as the subject's size, the severity of the signs and/or subject's symptoms, and the particular composition or route of administration selected.

Compositions containing an antibody for therapeutic use must be sterile and fluid to the extent that the composition is deliverable by syringe. In addition to water, the carrier can be an isotonic buffered saline solution, ethanol, polyol (e.g., glycerol, propylene glycol, and liquid polyetheylene glycol, and the like), and suitable mixtures thereof. Proper fluidity can be maintained, e.g., by use of coating such as lecithin, by maintenance of required particle size in the case of dispersion and by use of surfactants. In many cases, isotonic agents, e.g., sugars, polyalcohols such as mannitol or sorbitol, and sodium chloride, can be included in the composition. Long-term absorption of the injectable compositions can be brought about by including in the composition an agent which delays absorption, e.g., aluminum monostearate or gelatin.

Methods of Use

The antibodies (e.g., human monoclonal antibodies) have utility in therapy and/or detection of anthrax. The antibodies can be used to elicit in vivo or in vitro one or more of the following biological activities: (1) prevent entry or translocation of anthrax toxin into the cell; (2) prevent binding of protective antigen to ATR (such as ANTXR1 and/or ANTXR2) on cells that express ATR; (3) inhibit cleavage of PA83 to PA63; (4) prevent formation of the PA heptamer; (5) block or reduce binding of a toxin (edema factor or lethal factor) to the heptamer; (6) inhibit or prevent internalization of EF and/or LF; (7) neutralize lethal factor or edema factor such that the toxins are unable to cause physiological damage to the cell (such as disabling host innate and/or adaptive immune response); and/or (8) otherwise protect cells against the lethal effects of toxins.

When the antibodies of the present invention are human or humanized antibodies, they are significantly less immunogenic and more therapeutically effective and useful when administered to human patients than non-human antibodies, such as murine or bovine antibodies. When treating human patients, human antibodies are even less immunogenic and more therapeutically effective and useful than humanized antibodies.

Methods of inhibiting a physiological activity of *B. anthracis* PA in a subject susceptible to infection by *B. anthracis* or susceptible to anthrax toxin toxicity are also contemplated. Such methods generally involve administering to the subject an effective amount of an anti-PA mAb described herein in the subject or the cell, such that the physiological activity of the PA is inhibited. Anti-PA mAbs that have neutralizing activity against anthrax toxin are of particular interest in such methods.

The invention also provides for a method of treating or reducing the toxicity of anthrax toxin. Such methods find application both in vivo and in vitro. In each method, an anti-PA mAb is administered to a subject or, for in vitro methods, contacted with a material suspected of having anthrax toxin (e.g., as a material suspected of being contaminated with anthrax toxin) in an amount effective to provide for neutralization of toxin by the antibody.

Any subject having or susceptible to anthrax toxin exposure can be treated according to the methods disclosed herein. In some embodiments, the subject is infected with *B. anthracis* or has been exposed to anthrax toxin, or is at risk of infection or exposure.

In some embodiments, the method of treating or reducing the toxicity of anthrax exposure in a subject further comprises administering an additional therapeutic agent. In certain embodiments, the additional therapeutic agent is an antibiotic or vaccine.

The invention also provides for a method for detecting the presence of *B. anthracis* PA in a sample comprising: (a) contacting the sample with the anti-PA antibody under conditions which allow for formation of a complex comprising the anti-PA antibody and the PA; and (b) detecting the formation of the complex.

The antibodies and methods of the present invention have numerous in vitro and in vivo diagnostic and therapeutic utilities involving the diagnosis, reducing and treatment of anthrax toxin toxicity. For example, anti-PA antibodies can be administered to a subject to treat and/or reduce, or prevent, anthrax toxin toxicity. The anthrax toxin toxicity may arise from anthrax exposure or infection by *B. anthracis*. In addition, a blood or tissue sample can be removed from a subject and contacted with an antibody under conditions which allow detection of anthrax PA in the sample in order to diagnose an anthrax infection in the subject.

In a particular embodiment, an anti-PA antibody are used in vivo to treat, prevent or diagnose anthrax exposure or infection. In one prophylactic use, the subject has not been exposed to anthrax, and therefore can undergo a prophylactic-preexposure treatment with a human antibody to prevent or reduce the risk of infection by anthrax or toxicity associated with anthrax exposure. In another prophylactic use, a subject known to have been exposed to anthrax, but who does not display signs or symptoms of disease, can undergo a post-exposure prophylactic treatment to prevent the pathology associated with anthrax disease progression. In a therapeutic treatment, the subject has been exposed to anthrax toxin or *B. anthracis* (cells or spores), is infected and exhibits signs and/or symptoms of the disease. Antibodies can be used in both of the prophylactic settings and in therapeutic treatment of anthrax.

For example, the antibodies and methods of the present invention can be used to treat a subject which has been (or suspected of having been) infected with *B. anthracis* and/or displays signs and/or symptoms of anthrax infection or exposure of anthrax or anthrax toxin. Such signs and/or symptoms can include one or more of the following: low $pO_2$ (oxygen in blood), elevated body temperature (measured fever), adventitious sounds on lung exam, low blood pressure (or other signs of shock), widened mediastinum on chest X-ray (e.g., due to lysis of lymph nodes draining the lungs), or other signs typically known to be associated with uncontrolled pulmonary anthrax infection and toxin release; symptoms can include shortness of breath, cough, chills, fever, weakness, pain with deep breath, or other symptoms generally associated with pulmonary anthrax. Cutaneous anthrax begins as a pruritic papule or vesicle that enlarges and erodes (1-2 days) leaving a necrotic ulcer with subsequent formation of a central black eschar. Gastrointestinal anthrax may result in pharyngeal lesions with sore throat, dypshagia marked neck swelling and regional lymphadenopathy, or intestinal infection characterized by fever, severe abdominal pain, massive ascites, hematemesis, and bloody diarrhea. As with any form of anthrax, hemorrhagic meningitis can result from hematogenous spread of the organism from the primary site.

Suitable routes of administering the antibodies (e.g., human monoclonal antibodies) in vivo and in vitro are well known in the art and can be selected by those of ordinary skill. For example, the antibody compositions can be administered by injection (e.g., intravenous or subcutaneous) as described supra. Suitable dosages of the molecules used will depend on the age and weight of the subject and the concentration and/or formulation of the antibody composition. A therapeutically effective dosage of antibody of the present invention for administration to a patient in need of (1) treatment (e.g., following infection with anthrax or exposure to anthrax or anthrax toxin, and showing clinical signs and/or symptoms), (2) prophylactic treatment (e.g., prevention of clinical manifestations of anthrax toxin toxicity such as neutropenia, clinical signs and/or clinical symptoms in patients suspected of exposure to anthrax or in patients infected with anthrax, but not showing clinical signs or symptoms), or (3) prophylaxis (e.g., prevention of anthrax toxin toxicity prior to exposure or infection by anthrax, including use in individuals who are allergic to antibiotics or where the anthrax is antibiotic resistant or in combination with vaccine therapy where the vaccine could take up to 18 months for efficacy), against anthrax toxin toxicity includes dosages from 0.1 mg/kg to 100 mg/kg. In particular embodiments, the skilled practitioner may administer from 0.3 mg/kg to 50 mg/kg or from about 1 mg/kg to 12 mg/kg. The dosage will depend on, inter alia, the health of the patient, whether infection by anthrax is present, whether signs or symptoms of anthrax disease are present, and whether administration is for prophylaxis. The skilled practitioner will appreciate that dosage of an antibody can be modified depending on these factors.

The following dosing regimens should, therefore, not be construed as limiting. For example, if a subject exhibits signs of anthrax infection or anthrax toxin exposure, then a substantially high dose can be administered, e.g., at least 25 mg/kg, or 50 mg/kg or even 100 mg/kg, in order to save the patients life. Alternatively, a subject who is believed to be infected but exhibits no signs or symptoms can benefit from relatively lower dosage, e.g, less than 12-15 mg/kg or even 1-3 mg/kg. In the subject who receives an anthrax vaccine, and therefore it is desirable to provide a therapeutic antibody to provide immediate protection against any anthrax exposure prior to suitable plasma levels of the patient's own antibodies from the vaccine, the practitioner can use intermediate dosage ranges, e.g., 12-50 mg/kg.

The antibodies can be co-administered with one or more other therapeutic or immunostimulatory agents. The antibody can be administered before, after or concurrently with the agent or can be co-administered with other known therapies including anthrax vaccines (e.g. AVA, or any of the vaccine compositions disclosed above), antibodies against LF, EF, PA, and B. anthracis antibiotics. Exemplary antibiotics to which B. anthracis is sensitive to include ciprofloxacin, doxycycline, chloramphenicol, clindamycin, tetracycline, rifampin, and vancomycin.

Immunodetection Methods

In some embodiments, the invention provides methods for detecting the presence of PA in a sample, which may include measuring an amount of anthrax PA, comprising contacting the test sample, and optionally a control sample, with a polypeptide and antibodies, or an antigen-binding fragment thereof, which specifically binds to PA, under conditions that allow for formation of a complex between the antibody, or antigen-binding fragment thereof, and PA. The formation of a complex is then detected, wherein a difference between complex formation of the sample compared to the control sample is indicative the presence of PA in the sample.

Antibodies reactive with PA can be used to detect anthrax toxin in a sample, which may be a biological sample or a non-biological sample. Such detection methods can be used in the context of diagnosis, as well as in identification of materials that may be contaminated with B. anthracis, and/or anthrax toxin.

In some embodiments, anti-PA antibodies can be used to detect levels of PA in a biological sample (e.g., in blood from an anthrax-infected subject), which levels can then be linked to certain disease symptoms. This can be achieved using any suitable detection assay, e.g., by contacting a test sample (and optionally a control sample) with the anti-PA antibody under conditions that allow for the formation of a complex between the antibody and protective antigen. The presence or absence of PA-antibody complexes is detected, and may optionally be compared to a level of a level of PA-antibody binding of a positive or negative control.

Suitable immunodetection techniques include, but are not necessarily limited to, both in vitro methods and in vivo (imaging) methods. Where the methods are in vitro, the biological sample can be any sample in which a PA antigen may be present, including but not limited to, blood samples (including whole blood, serum, etc.), tissues, whole cells (e.g., intact cells), tissue or cell extracts, as well as samples obtained from other sources (e.g., packages, letters, food products, and the like). Assays can take a wide variety of forms, such as competition, direct reaction, or sandwich type assays. Exemplary assays include Western blots; enzyme-labeled and mediated immunoassays, such as ELISAs; biotin/avidin type assays; radioimmunoassays; immunoelectrophoresis; immunoprecipitation, and the like. The reactions generally include detectable labels such as fluorescent, chemiluminescent, radioactive, enzymatic labels or dye molecules, or other methods for detecting the formation of a complex between antigen in the sample and the antibody or antibodies reacted therewith.

The assays can involve separation of unbound antibody in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Where a solid support is used, the solid support is usually first reacted with a solid phase component (e.g., an anti-PA antibody) under suitable binding conditions such that the component is sufficiently immobilized to the support. In some instances, immobilization to the support can be enhanced by first coupling the antibody to a protein with better binding properties, or that provides for immobilization of the antibody on the support with out significant loss of antibody binding activity or specificity. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind antibodies the support include polysaccharides, polylactic acids, polyglycolic acids, polymeric amino acids, amino acid copolymers, and the like, with the proviso that the molecule used to immobilize the antibody does not adversely impact the ability of the antibody to specifically bind antigen. Such molecules and methods of coupling these molecules to the antigens, are well known to those of ordinary skill in the art. See, e.g., Brinkley, M. A. Bioconjugate Chem. (1992) 3:2-13; Hashida et al., J. Appl. Biochem. (1984) 6:56-63; and Anjaneyulu and Staros, International J. of Peptide and Protein Res. (1987) 30:117-124.

After reacting the solid support with the solid phase component, any non-immobilized solid-phase components are removed from the support by washing, and the support-bound component is then contacted with a biological sample suspected of containing PAs under suitable binding conditions. After washing to remove any non-bound ligand, a secondary binder moiety is added under suitable binding conditions, wherein the secondary binder is capable of associating selectively with the bound ligand. The presence or absence of the secondary binder can then be detected using techniques well known in the art.

An ELISA method can be used, wherein the wells of a microtiter plate are coated with anti-PA antibody according to the present invention. A biological sample containing or suspected of containing PA is then added to the coated wells. After a period of incubation sufficient to allow antibody binding, the plate(s) can be washed to remove unbound moieties and a detectably labeled secondary binding molecule added. The secondary binding molecule is allowed to react with any captured antigen, the plate washed and the presence or absence of the secondary binding molecule detected using methods well known in the art.

Where desired, the presence or absence of bound PA from a biological sample can be readily detected using a secondary binder comprising an antibody directed against the antibody ligands. For example, a number of anti-human immunoglobulin (Ig) molecule are known in the art which can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the antibodies and PA form complexes under precipitating conditions. For example, the antibody can be attached to a solid phase particle (e.g., an agarose bead or the like) using coupling techniques known in the art, such as by direct chemical or indirect coupling. The antibody-coated particle is then contacted under suitable binding conditions with a biological sample suspected of containing PA to provide for formation of particle-antibody-PA complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above.

The above-described assay reagents, including the anti-PA antibodies, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

Kits

Kits having one or more of the compositions disclosed herein and useful for practicing one or more of the methods disclosed herein are also contemplated. The kits can include one or more of, depending upon the intended use of the kit, the compositions described herein, such as: an anti-PA mAb, a nucleic acid encoding the same (especially a nucleic acid encoding a CDR of a heavy and/or light chain of anti-PA mAb), expression vectors (which may optionally contain anti-PA mAb encoding nucleic acid(s), primers to facilitate production of DNA fragments for use with expression vectors disclosed herein, or a recombinant cell containing anti-PA mAb-encoding nucleic acid. Other optional components of the kit include: buffers, etc., for administering the anti-PA mAb, and/or for performing an immunodetection assay. The various components of the kit may be present in separate containers or certain compatible components may be precombined into a single container, as desired.

In addition to above-mentioned components, the subject kits typically further include instructions for using the components of the kit to practice the disclosed methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Deposit Information:

The following materials were deposited with the American Type Culture.

| ATCC Deposit No. | Description |
| --- | --- |
| PTA-8051 | Strain designation: CHORI MONO MIX. A mixture of plasmid DNA, each encoding both the heavy and light chains of human monoclonal antibodies 1A5, 4A12, 24B1, 24G4, 32E12, or 33F4 |
| PTA-8207 | Strain designation: CHORI VECTOR MIX. A mixture of plasmid DNA each encoding expression vectors pARC/Fab, pARC/SC, or pCI/IRES |

This deposit is provided merely as convenience to those of skill in the art, and is not an admission that a deposit is required under 35 U.S.C. §112. The sequence of the polynucleotides contained within the deposited material, as well as the amino acid sequence of the polypeptides encoded thereby, are incorporated herein by reference and are controlling in the event of any conflict with the written description of sequences herein. A license may be required to make, use, or sell the deposited material, and no such license is granted hereby.

Retrieval of Individual Clones from Deposit of Pooled Clones

The CHORI MONO MIX deposit was prepared by separately transfecting DNA encoding the human monoclonal antibodies 1A5, 4A12, 24B1, 24G4, 32E12, and 33F4 into *E. coli* cells for expansion and plasmid production. Plasmid DNA was prepared from each of the clones, and a mixture was made containing each plasmid at equal concentration, and the mixture aliquoted such that tube contained at least 100 ng of each plasmid.

The CHORI VECTOR MIX deposit was prepared by separately transfecting DNA encoding the vectors pARC/Fab, pARC/SC, and pCI/IRES into *E. coli* cells for expansion and plasmid production. Plasmid DNA was prepared from each of the clones, and a mixture was made containing each plasmid at equal concentration, and the mixture aliquoted such that tube contained at least 100 ng of each plasmid.

Particular clones can be obtained from the composite deposit using methods well known in the art. For example, a bacterial cell containing a particular clone can be identified by isolating single colonies, and identifying colonies containing the specific clone through standard colony hybridization techniques, using an oligonucleotide probe or probes designed to specifically hybridize to a sequence of the clone insert (e.g., a probe based upon a sequence of the polynucleotide) The probe should be designed to have a Tm of approximately 80° C. (assuming 2° C. for each A or T and 4° C. for each G or C). Positive colonies can then be picked, grown in culture, and the recombinant clone isolated. Alternatively, probes designed in this manner can be used to PCR to isolate a nucleic acid molecule from the pooled clones according to methods well known in the art, e.g., by purifying the cDNA from the deposited culture pool, and using the probes in PCR reactions to produce an amplified product having the corresponding desired polynucleotide sequence. Alternatively, each clone insert can be directly sequenced using the T7 promoter sequencing primer.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Vector Production

This example describes production of exemplary expression vectors having cloning sites for heavy and light chain coding sequences and using infrequently cutting enzymes having recognition sequences of 8 bases or longer are described in this example.

pARC/Fab

The pARC/Fab vector, illustrated in FIG. 13, Panel A, was designed for the expression of antibody Fab fragments in a bacterial host, especially *E. coli*. The vector was constructed by inserting the pARC/Fab expression cassette (see FIG. 13, Panel C) into the Afl III/Hind III cloning site of pUC18. Full light chains are generated by means of PCR and inserted into the Fse I/Not I cloning site. Heavy chain Fd fragments (VH+CH1) generated by means of PCR can be inserted into the Pac I/Asc I cloning site. The four "cloning" restriction enzymes have 8 base recognition sequences that do not occur in any known immunoglobulin germline gene, and rarely arise during the course of somatic hypermutation The OmpA and MalE leader sequences direct the respective proteins into the periplasmic space where interchain and intrachain disulfide bonds are formed to produce Fab molecules. Fabs are purified from *E. coli* lysates by utilizing metal-chelate chromatography and the poly His tag added to the heavy chain fragment.

pARC/SC

This vector is designed for the expression of single chain antibody Fab fragments in a bacterial host, especially *E. coli*. The vector was constructed by inserting the pARC/SC expression cassette (see FIG. 13, Panel B) into the Afl III/Hind III cloning site of pUC18. Full light chains are generated by means of PCR and inserted into the Fse I/Not I cloning site. Heavy chain Fd fragments (VH+CH1) can be generated by means of PCR and inserted into the Pac I/Asc I cloning site. The four "cloning" restriction enzymes have 8 base recognition sequences that do not occur in any known immunoglobulin germline gene, and rarely arise during the course of somatic hypermutation The linker sequence allows the Fab to be synthesized as a single chain. The OmpA leader sequence direct the protein into the periplasmic space where intrachain disulfide bonds are formed to produce single chain Fab molecules. Fabs are purified from *E. coli* lysates by utilizing metal-chelate chromatography and the poly His tag added to the heavy chain fragment.

pCI/IRES

This vector is designed for the expression of Fabs isolated using either pARC/Fab or pARC/SC vectors as complete IgG molecules in mammalian cell lines such as CHO and HEK. The vector was constructed by inserting the PCI/IRES cassette (see FIG. 13, Panel C) into the Nhe I/Eag I cloning site of the pCI-Neo expression vector (Promega). Full light chains are transferred into the Fse I/Not I cloning site. Heavy chain Fd fragments (VH+CH1) can be transferred into the Pac I/Asc I cloning site. The expression cassette is a bicistronic construct utilizing an internal ribosome entry site (IRES) sequence to facilitate the expression of both heavy and light chain protein from a single mRNA sequence. The vector supplies the light chain leader sequence, the heavy chain leader sequence and the second and third domains of the IgG1 constant region. The product is secreted into the culture medium, and is purified using standard Protein A or Protein G affinity chromatography.

Example 2

Production of Antibody Expression Library Having Antigen Binding Specificity for Pa of *B. Anthracis*

Adult humans were immunized using the PA protein of *B. anthracis*. Blood is collected prior to vaccination and 30 days following vaccination to determine serum antibody response.

A 100-mL blood sample is collected 7 days following vaccination for the isolation of mononuclear cells (MNCs).

The MNCs were isolated from the 7-day post-vaccination blood sample by using Ficoll-Hypaque. An aliquot ($10^6$ cells) is placed into culture for 7 days in 1 mL RPM1 1640 medium supplemented with 5% fetal calf serum, the supernatant is assayed for PA protein specific antibody production, and the heavy chain and light chain isotypes of secreted antibody were determined. PA protein is biotynylated and used to arm avidin-coated paramagnetic beads. These PA-coated beads are washed and added to $2\times10^7$ MNCs (preabsorbed with avidin-coated paramagnetic beads), and the mixture is incubated on ice for 30 min. PA-binding cells are then isolated with a magnet. Positively selected cells are washed twice with cold phosphate-buffered saline-0.5% bovine serum albumin and used for RNA extraction.

RNA is prepared from affinity-isolated cells (RNEasy, Qiagen, Valencia Calif.), and cDNA is prepared by using Thermoscript reverse transcription-PCR system (GIBCO BRL, Carlsbad, Calif.) according to the manufacturer's instructions. cDNA is used as a template in the PCR to generate heavy chain Fd fragments (VDJ-CH1) and total κ and λ chains for insertion into the expression vector.

Heavy chain PCR fragments are inserted into the PacI/AscI site of the pARC/Fab or pARC/SC vector, and the resultant products are expanded in E. coli. Bulk light chain PCR fragments are inserted into the FseI/NotI site of the heavy chain library, and the resultant ligation products transfected into XL1-Blue E. coli cells. This results in an expression library in which both heavy and light chains are synthesized from a single construct and transported to the periplasmic space where functional antibody Fabs are assembled. Individual colonies are manually picked and inoculated into 2 ml, 96 well culture plates. Following replica plating, cultures are grown overnight. In order to extract Fab protein for screening, the cultures are centrifuged and the cell pellets lysed in buffer by repeated rounds of freezing and thawing. Samples are centrifuged and lysate transferred onto 96 well assay plates that have been coated with anti-human light chain antibody. The Fab proteins from the samples are allowed to bind to the anti-human light chain antibody in the wells. This is followed by a washed, and radio-labeled antigen is added to each well. Wells containing antigen-specific Fabs are identified using a Storm™ phosphoimager (Molecular Dynamics, Inc, Sunnyvale, Calif.). The clones that screen positive are streaked for single colony isolation from the replica plate, and individual colonies re-screened to verify binding. The heavy and light chain variable region sequences of the antigen-binding clones are determined by standard methodologies using chain-specific sequencing primers. Subsequent sequence analysis identifies the germline genes that encode the individual variable regions, and this delineates the degree to which they have diverged in sequence during the course of affinity maturation.

Individual clones which are chosen for expansion are then cultured at a large scale, and the Fab protein extracted and purified by metal chelate chromatography utilizing the polyhistidine region incorporated into the pARC expression vector.

The pARC/Fab and pARC/SC expression vector systems use a matched system of vectors and primers. In this system the entire light chain and the V/D/J/CH1 domains of the heavy chain are inserted in frame with sequences specifying leader peptides that direct the synthesized product to the periplasmic space of E. coli. Vectors are designed with minimal internal sequence homology for increased stability. The vectors use rare-cutting restriction enzymes with eight-base recognition sequences. These sequences do not occur in the human germline immunoglobulin genes, and rarely arise in the course of affinity maturation of the response.

The antibody fragments can be expressed using two formats. The pARC/Fab vector encodes the heavy and light chains as individual proteins with their own leaders. Heavy and light chain proteins are directed to the periplasmic space following synthesis, where they fold to form dimeric Fab molecules stabilized by inter-chain disulfide bonds. This format is highly homologous to the native structure of the antibody. The pARC/Fab vector expresses antibody Fab fragments in E. coli. The vector is constructed by inserting the pARC/Fab expression cassette (see FIG. 13, Panel A) into the AflIII/HindIII cloning site of pUC18. Full light chains are generated by means of PCR and inserted into the FseI/NotI cloning site of pARC/Fab. Heavy chain Fd fragments ($V_H$+$C_{H1}$) are generated by means of PCR and inserted into the PacI/AscI cloning site of pARC/Fab. Suitable primers for the PCR are shown in FIGS. 16 and 17. These four restriction enzymes have eight-base recognition sequences that do not occur in any known immunoglobulin germline gene, and rarely arise during the course of somatic hypermutation. The OmpA and MalE leader sequences direct the respective polypeptides into the periplasmic space where interchain and intrachain disulfide bonds are formed to produce Fab antibody fragments. Using this vector system, the heavy chain fragment has a poly His tag at the C-terminus of the polypeptide, which allows purification of the Fab antibody fragments from E. coli lysates using metal-chelate chromatography.

Alternately, the antibody fragments can be expressed as a single chain molecule in which the heavy and light chains are joined by a flexible linker. Single chain Fabs differ from traditional scFV in that the entire light chain as well as the CH1 region of the heavy chain is synthesized. This format eliminates problems of unbalanced chain synthesis seen with traditional "double chain" Fab expression systems. Further, unlike scFvs which are often deposited as inclusion bodies in E. coli, these single chain Fab fragments are mainly secreted as soluble products into the periplasmic space of the E. coli host cells. This facilitates screening of large expression libraries. The pARC/Fab and pARC/SC vectors allow for the Fabs to be easily switched between the two as required. The heavy and light chain specific primers shown in FIGS. 16 and 17 encompass all known V gene families and incorporate the required restriction sites. These primers are useful in amplifying a wide range of human immunoglobulin gene products.

The pARC/SC vector expresses single chain antibody Fab fragments in E. coli. The vector is constructed by inserting the pARC/SC expression cassette (see FIG. 13, Panel B) into the AflIII/HindIII cloning site of pUC18. Full light chains are generated by means of PCR and inserted into the FseI/NotI cloning site. Heavy chain Fd fragments ($V_H$+$C_{H1}$) are generated by means of PCR and inserted into the PacI/AscI cloning site. Suitable primers for the PCR are shown in FIGS. 16 and 17. These four restriction enzymes have eight-base recognition sequences that do not occur in any known immunoglobulin germline gene, and rarely arise during the course of somatic hypermutation. The linker sequence allows the Fab to be synthesized as a single chain Fab molecule. The OmpA leader sequence directs the polypeptide into the periplasmic space where intrachain disulfide bonds are formed to produce single chain Fab antibody fragments. Using this vector system, the heavy chain fragment has a poly His tag at the C-terminus of the polypeptide, which allows purification of the single chain Fab antibody fragments from E. coli lysates using metal-chelate chromatography.

In an alternate method, the PCR fragments are cloned into the pCI/IRES expression vector, where the NheI/NotI expression cassette is inserted into NheI/NotI cloning site of pCI-neo. The pCI-neo mammalian vector is commercially available from Promega Corp. (Madison, Wis.). The structure of the NheI/NotI expression cassette is depicted in FIG. 13, Panel C. The nucleotide sequence of the NheI/NotI expression cassette is depicted in FIG. 18. The IRES sequence is derived from the IRES sequence of the pIRESpuro3 vector (commercially available from BD Biosciences, San Jose, Calif.). The amino acid sequences of the leader sequences and heavy chain constant domain are provided in the table below:

| Sequence Encoded | Amino Acid Sequence |
|---|---|
| human kappa light chain leader | Met Glu Ala Pro Ala Gln Leu Leu Phe Leu Leu Leu Leu Trp Leu Pro Asp Thr Thr Gly (SEQ ID NO: 115) |
| human heavy chain leader | Met Glu Phe Gly Leu Ser Trp Leu Phe Leu Val Ala Ile Leu Lys Gly Val Gln Cys (SEQ ID NO: 116) |
| human heavy CH2/CH3 constant domain | Ala Arg His Thr Cys Pro Pro Cys Pro Ala Pro Glu Leu Leu Gly Gly Pro Ser Val Phe Leu Phe Pro Pro Lys Pro Lys Asp Thr Leu Met Ile Ser Arg Thr Pro Glu Val Thr Cys Val Val Val Asp Val Ser His Glu Asp Pro Glu Val Lys Phe Asn Trp Tyr Val Asp Gly Val Glu Val His Asn Ala Lys Thr Lys Pro Arg Glu Glu Gln Tyr Asn Ser Thr Tyr Arg Val Val Ser Val Leu Thr Val Leu His Gln Asp Trp Leu Asn Gly Lys Glu Tyr Lys Cys Lys Val Ser Asn Lys Ala Leu Pro Ala Pro Ile Glu Lys Thr Ile Ser Lys Ala Lys Gly Gln Pro Arg Glu Pro Gln Val Tyr Thr Leu Pro Pro Ser Arg Asp Glu Leu Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Lys Leu Thr Val Asp Lys Ser Arg Trp Gln Gln Gly Asn Val Phe Ser Cys Ser Val Met His Glu Ala Leu His Asn His Tyr Thr Gln Lys Ser Leu Ser Leu Ser Pro Gly Lys (SEQ ID NO: 117) |

An amino acid sequence encoded 5' of the coding sequence for the CH2/CH3 amino acid sequence is indicated as SEQ ID NO:119. The heavy chain PCR fragments are inserted into the PacI/AscI site of the pCI/IRES vector, and the resultant products are expanded in *E. coli*. The light chain PCR fragments are inserted into the FseI/NotI site of the heavy chain library, and the resultant ligation products transfected into a suitable mammalian cell, such as CHO. The pCI/IRES vector encodes the heavy and light chains as individual proteins with their respective human light chain leader and the human heavy chain leader. The pCI/IRES vector expresses the antibody in a mammalian cell.

Example 3

Anti-PA Antibodies

Anti-PA antibodies were generated by collecting a 100 ml peripheral blood sample from a human donor 7 days following the 6th immunization with AVA (Anthrax Vaccine Adsorbed (BioThrax). This sample was used for the isolation of mononuclear cells (MNCs). MNCs were isolated from the 7-day post-vaccination blood sample using Ficoll-Hypaque. An aliquot ($1\times10^6$ cells) was placed into culture for 7 days in 1 ml RPMI 1640 supplemented with 5% fetal calf serum and the supernatant assayed for PA-specific antibody production. PA was biotinylated as previously described and used to "arm" avidin-coated paramagnetic beads (Immunotech Inc., Marseilles, France). These PA-coated beads were washed and added to $2\times10^7$ MNC that had been pre-absorbed with avidin-coated magnetic beads. The mixture was then incubated on ice for 30 min. PA-binding cells were isolated with a magnet. Positively selected cells were washed twice with cold PBS/ 0.5% BSA, and used for RNA extraction.

Construction of Fab expression libraries: Expression libraries were constructed using the pARC vector system described herein. Total RNA was prepared from affinity-isolated cells (RNAeasy, Qiagen, Valencia, Calif.) and cDNA prepared using the Thermoscript RT-RCR System (GIBCO BRL, Carlsbad, Calif.) according to the manufacturers instructions. cDNA was used as a template in the polymerase chain reaction (PCR) to generate H chain Fd fragments (VDJ-CH1) and total kappa and lambda L chains for insertion into the expression vector. L chain fragments were inserted into the Fse I/Not I site of the pARC vector, and the resulting L chain library electroporated into XL1-Blue *E. coli* cells. An aliquot was plated to determine transformation efficiency, and the balance expanded for 8 hrs. Plasmid DNA was purified from the expanded culture, digested with Pac I and Asc I, purified, and the H chain Fd fragments ligated into the Pac I/Asc I site of L chain library plasmid DNA. The FdxL library was electroporated into XL1-Blue cells, plated at low density on LB/carbenicillin plates, grown overnight, and individual colonies selected for analysis.

Identification of PA-specific Fabs: Individual transformed *E. coli* colonies were selected, mastered onto an LB/carbenicillin agar plate, and grown in 1 ml overnight cultures in deep well 96-well plates under antibiotic selection. Bacteria were pelleted by centrifugation, re-suspended in 140 µl lysis buffer (PBS+protease inhibitor cocktail (Complete, Roche Molecular Biochemicals, Indianapolis, Ind.), rapidly frozen and thawed 3 times using liquid nitrogen, and the cellular debris pelleted by centrifugation. Fifty ml of the lysate was added to assay plates that had been coated overnight with human light-chain specific antibody (Biosource International, Camarillo, Calif.) and incubated for 2 hrs at 37° C. to facilitate capture of the Fabs. Plates were then washed and 50 µl $^{125}$I-PA added to each well. Following incubation at 37° C. for 2 hrs, plates were washed, placed on a PhosphorImager detection plate (Molecular Dynamics, Sunnyvale, Calif.). Following exposure, the PhosphorImager plates were scanned, and PA binding wells identified. Residual lysate from corresponding clones was re-assayed for binding. Positive cultures were identified on the master plates, streaked for isolation, individual colonies picked and grown overnight and Fab production and PA binding verified. For selected clones, heavy and light chain gene sequences were isolated by restriction enzyme digest and ligated into the pCI/IRES vector. Vector DNA was then expanded in *E. coli*, purified, and transfected into CHO cells for full chain antibody production. Antibody was purified from the supernatant using Protein A chromatography.

Results. The use of any of the above method resulted in an expression library of anti-PA antibodies. Six human anti-PA antibodies were isolated, and the nucleic acid and amino acid sequences determined. These anti-PA antibodies were given the designations: 1A5, 4A12, 24B1, 24G4, 32E12, or 33F4 (see FIGS. 1-12). FIGS. 1-12 indicate the position of the CDRs of the heavy and light chain variable regions. Alignment of the $V_H$ and $V_L$ regions of the antibodies is shown in FIG. 19.

The binding specificity of the mAbs is as follows:
Antibody 1A5 is specific for epitopes residing in the PA63 domain of the PA molecule
Antibody 4A12 is specific for epitopes resideing in the Domain 4 of the PA molecule
Antibody 24B1 is specific for epitopes resideing in the PA63 domain of the PA molecule
Antibody 24G4 is specific for epitopes resideing in the PA63 domain of the PA molecule
Antibody 33F4 is specific for epitopes resideing in the PA20 domain of the PA molecule
The Domain specificity of 32E12 has not yet been determined.

Example 4

Characterization of Anti-PA mAbs

PA Neutralization Assay. LF (*B. anthracis* lethal factor) rapidly kills the murine cell line RAW 264.7 in the presence of PA. Antibodies that neutralize PA function block this cytotoxicity when co-cultured with the PA/LA-RAW 264.7 mix. This forms the basis of a toxin neutralization assay. To test antibodies for their ability to neutralize PA, titrated amounts of antibody are added to cultures of RAW 264.7 cells along with 300 ng PA and 1000 ng LF. Cells are cultured for 12 hrs, and cell viability then assayed. The amount of antibody required to cause a 50% reduction of cytotoxicity ($IC_{50}$) is determined and can be used to compare the relative effectiveness of different antibodies in neutralizing toxin.

Figure 20:
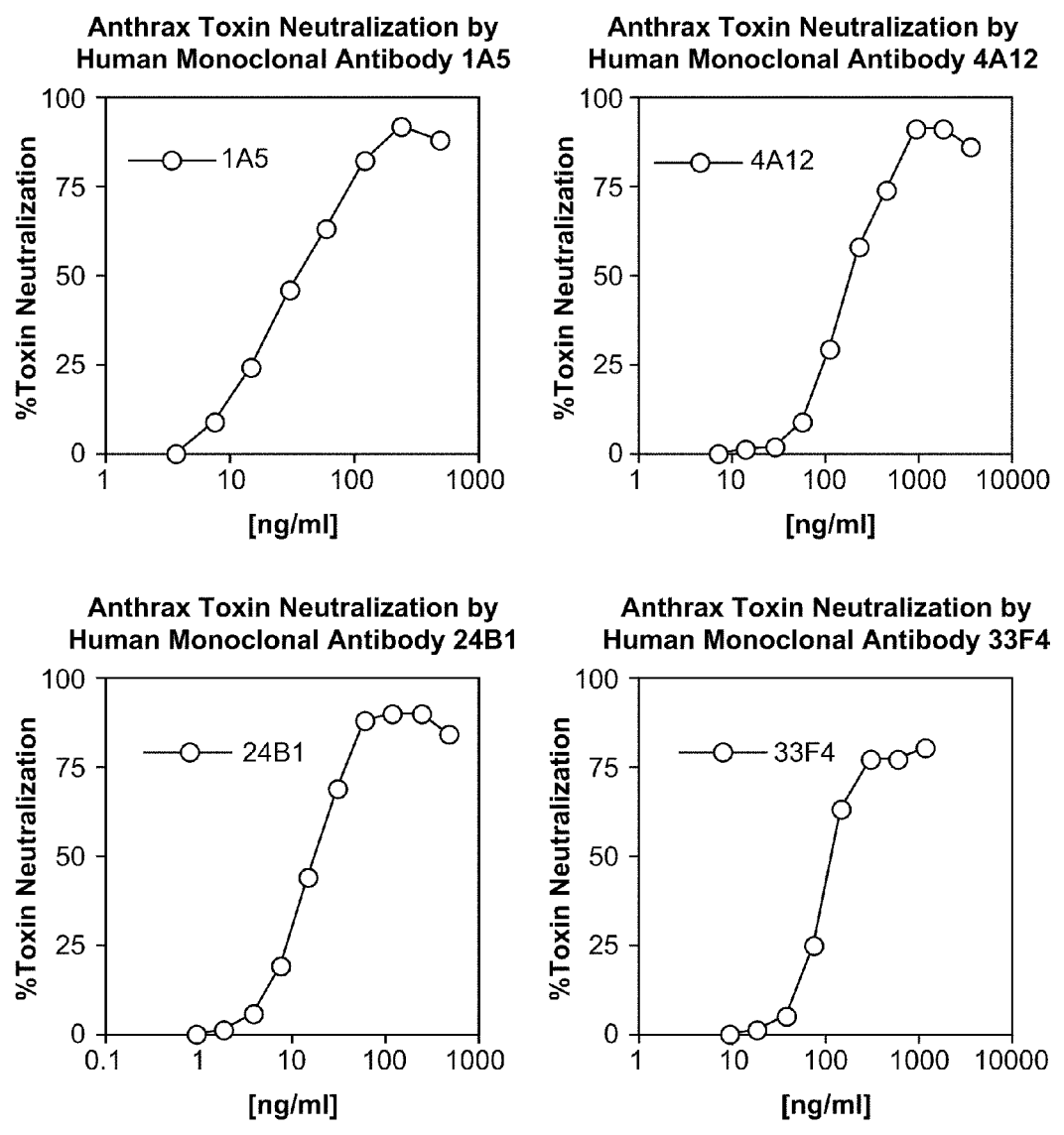
Figure 21:
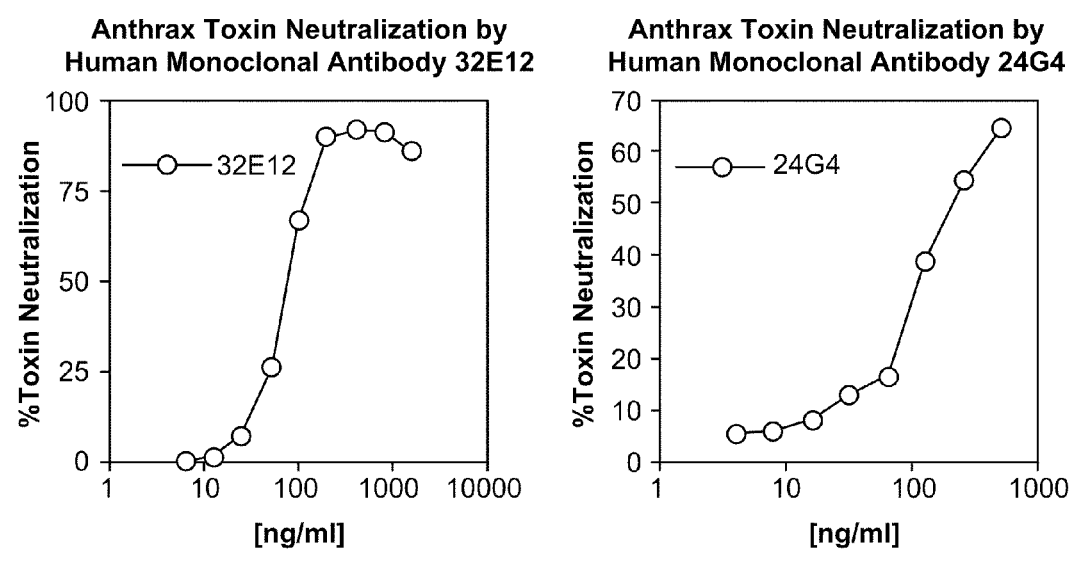

The results of the in vitro neutralization assays are shown in FIGS. 20 and 21. All antibodies neutralize PA at stoichiometric ratios that indicate one antibody molecule is able to neutralize more than one PA molecule. For each of the monoclonals, the ratio of antibody to PA (Ab:PA) at which 50% neutralization (IC50) occurs is as follows:
For antibody 1A5, Ab:PA ratio at $IC_{50}$=1:16
For antibody 4A12, Ab:PA ratio at $IC_{50}$=1:3
For antibody 24B1, Ab:PA ratio at $IC_{50}$=1:30
For antibody 24G4, Ab:PA ratio at $IC_{50}$=1:2.6
For antibody 33F4, Ab:PA ratio at $IC_{50}$=1:4.5
For antibody 32E12, Ab:PA ratio at $IC_{50}$=1:7
These ratios are indicative of highly efficient toxin neutralization and sufficient to suggest that PA toxin neutralization could be achieved at therapeutically practical levels.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. An isolated antibody, or antigen binding fragment thereof, comprising:
    a heavy chain polypeptide comprising contiguous amino acid sequences of complementarity determining regions (CDRs) CDRH1, CDRH2, and CDRH3 of a variable heavy chain polypeptide having the amino acid sequence of SEQ ID NO: 13;
    and a light chain polypeptide comprising contiguous amino acid sequences of a CDRL1, a CDRL2; and
    a CDRL3 of a variable light chain polypeptide having the amino acid sequence of SEQ ID NO: 17, wherein the antibody, or antigen binding fragment thereof binds to protective antigen (PA).

2. A pharmaceutical composition comprising a pharmaceutically acceptable carrier and the isolated antibody, or antigen binding fragment thereof, of claim 1.

3. A library of antibodies comprising the antibody, or antigen binding fragment thereof, of claim 1 and at least one antibody selected from the group consisting of 4A12, 24B1, 24G4, 32E12, and 33F4.

4. A method of producing a polypeptide, the method comprising:
    culturing a host cell comprising a nucleic acid encoding the antibody, or antigen binding fragment thereof, according to claim 1 under conditions to provide for polypeptide expression.

5. An isolated antibody, or an antigen binding fragment thereof, comprising:
    a heavy chain polypeptide comprising contiguous amino acid sequences of the complementarity determining regions (CDRs) CDRH1, CDRH2, and CDRH3 of a variable heavy chain polypeptide having the amino acid sequence of SEQ ID NO: 21; and
    a light chain polypeptide comprising contiguous amino acid sequences of a CDRL1, a CDRL2, and a CDRL3 of a variable light chain polypeptide having the amino acid sequence of SEQ ID NO: 25, wherein the antibody, or antigen binding fragment thereof binds to protective antigen (PA).

6. A pharmaceutical composition comprising a pharmaceutically acceptable carrier and the isolated antibody, or antigen binding fragment thereof, of claim 5.

7. A library of antibodies comprising the antibody, or antigen binding fragment thereof of claim 5 and at least one antibody selected from the group consisting of 1A5, 24B1, 24G4, 32E12, and 33F4.

8. An isolated antibody, or an antigen binding fragment thereof, comprising:
    a heavy chain polypeptide comprising contiguous amino acid sequences of the complementarity determining regions (CDRs) CDRH1, CDRH2, and CDRH3 of a variable heavy chain polypeptide having the amino acid sequence of SEQ ID NO: 29; and
    a light chain polypeptide comprising contiguous amino acid sequences of a CDRL1, a CDRL2, and a CDRL3 of a variable light chain polypeptide having the amino acid sequence of SEQ ID NO: 33, wherein the antibody, or antigen binding fragment thereof binds to protective antigen (PA).

9. A pharmaceutical composition comprising a pharmaceutically acceptable carrier and the isolated antibody, or antigen binding fragment thereof, of claim 8.

10. A library of antibodies comprising the antibody, or antigen binding fragment thereof of claim 8 and at least one antibody selected from the group consisting of 1A5, 4A12, 24G4, 32E12, and 33F4.

11. An isolated antibody, or an antigen binding fragment thereof, comprising:
    a heavy chain polypeptide comprising contiguous amino acid sequences of the complementarity determining regions (CDRs) CDRH1, CDRH2, and CDRH3 of a variable heavy chain polypeptide having the amino acid sequence of SEQ ID NO: 37; and
    a light chain polypeptide comprising contiguous amino acid sequences of a CDRL1, a CDRL2, and a CDRL3 of a variable light chain polypeptide having the amino acid sequence of SEQ ID NO: 41, wherein the antibody, or antigen binding fragment thereof binds to protective antigen (PA).

12. A pharmaceutical composition comprising a pharmaceutically acceptable carrier and the isolated antibody, or antigen binding fragment thereof, of claim 11.

13. A library of antibodies comprising the antibody, or antigen binding fragment thereof of claim 11 and at least one antibody selected from the group consisting of 1A5, 4A12, 24B1, 32E12, and 33F4.

14. An isolated antibody, or an antigen binding fragment thereof, comprising:
    a heavy chain polypeptide comprising contiguous amino acid sequences of the complementarity determining regions (CDRs) CDRH1, CDRH2, and CDRH3 of a variable heavy chain polypeptide having the amino acid sequence of SEQ ID NO: 45; and
    a light chain polypeptide comprising contiguous amino acid sequences of a CDRL1, a CDRL2, and a CDRL3 of a variable light chain polypeptide having the amino acid sequence of SEQ ID NO: 49, wherein the antibody, or antigen binding fragment thereof binds to protective antigen (PA).

15. A pharmaceutical composition comprising a pharmaceutically acceptable carrier and the isolated antibody, or antigen binding fragment thereof, of claim 14.

16. A library of antibodies comprising the antibody, or antigen binding fragment thereof of claim 14 and at least one antibody selected from the group consisting of 1A5, 4A12, 24B1, 24G4, and 33F4.

17. An isolated antibody, or an antigen binding fragment thereof, comprising:
    a heavy chain polypeptide comprising contiguous amino acid sequences of the complementarity determining regions (CDRs) CDRH1, CDRH2, and CDRH3 of a variable heavy chain polypeptide having the amino acid sequence of SEQ ID NO: 53; and a light chain polypeptide comprising contiguous amino acid sequences of a CDRL1, a CDRL2, and a CDRL3 of a variable light chain polypeptide having the amino acid sequence of SEQ ID NO: 57, wherein the antibody, or antigen binding fragment thereof binds to protective antigen (PA).

18. A pharmaceutical composition comprising a pharmaceutically acceptable carrier and the isolated antibody, or antigen binding fragment thereof, of claim 17.

19. A library of antibodies comprising the antibody, or antigen binding fragment thereof of claim 17 and at least one antibody selected from the group consisting of 1A5, 4A12, 24B1, 24G4, and 32E12.

20. A method of producing a polypeptide, the method comprising:
 culturing a host cell comprising a nucleic acid encoding the antibody, or antigen binding fragment thereof, according to claim 5 under conditions to provide for polypeptide expression.

21. A method of producing a polypeptide, the method comprising:
 culturing a host cell comprising a nucleic acid encoding the antibody, or antigen binding fragment thereof, according to claim 8 under conditions to provide for polypeptide expression.

22. A method of producing a polypeptide, the method comprising:
 culturing a host cell comprising a nucleic acid encoding the antibody, or antigen binding fragment thereof, according to claim 11 under conditions to provide for polypeptide expression.

23. A method of producing a polypeptide, the method comprising:
 culturing a host cell comprising a nucleic acid encoding the antibody, or antigen binding fragment thereof, according to claim 14 under conditions to provide for polypeptide expression.

24. A method of producing a polypeptide, the method comprising:
 culturing a host cell comprising a nucleic acid encoding the antibody, or antigen binding fragment thereof, according to claim 17 under conditions to provide for polypeptide expression.

* * * * *

SEQUENCE LISTING

```
<160> NUMBER OF SEQ ID NOS: 119

<210> SEQ ID NO 1
<211> LENGTH: 449
<212> TYPE: PRT
<213> ORGANISM: Homo sapiens

<400> SEQUENCE: 1

Glu Leu Ile Asn Leu Gln Glu Ser Gly Pro Gly Leu Val Lys Pro Ser
1               5                   10                  15

Glu Thr Leu Ser Leu Thr Cys Thr Val Ser Gly Gly Ala Met Asn Ser
            20                  25                  30

His Phe Trp Ser Trp Ile Arg Gln Ser Pro Gly Lys Gly Leu Glu Trp
        35                  40                  45

Ile Gly Tyr Ile Tyr Ser Gly Gly Thr Thr Asn Tyr Asp Pro Ser Leu
    50                  55                  60

Lys Ser Arg Val Ala Ile Ser Ile Asp Thr Ser Lys Lys Gln Phe Ser
```

```
               65                  70                  75                  80
Leu Lys Leu Arg Ser Val Thr Ala Ala Asp Thr Ala Val Tyr Tyr Cys
                    85                  90                  95
Ala Arg Gly Asp Met Val Thr Gly Asp Pro Gly Asp Tyr Trp Gly Gln
                    100                 105                 110
Gly Thr Leu Val Thr Val Ser Ser Ala Ser Thr Lys Gly Pro Ser Val
                    115                 120                 125
Phe Pro Leu Ala Pro Ser Ser Lys Ser Thr Ser Gly Gly Thr Ala Ala
                    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                    165                 170                 175
Leu Gln Ser Ser Gly Leu Tyr Ser Leu Ser Ser Val Val Thr Val Pro
                    180                 185                 190
Ser Ser Ser Leu Gly Thr Gln Thr Tyr Ile Cys Asn Val Asn His Lys
                    195                 200                 205
Pro Ser Asn Thr Lys Val Asp Lys Thr Val Glu Arg Lys Cys Trp Ala
210                 215                 220
Arg His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                    245                 250                 255
Arg Thr Pro Glu Val Thr Cys Val Val Val Asp Val Ser His Glu Asp
                    260                 265                 270
Pro Glu Val Lys Phe Asn Trp Tyr Val Asp Gly Val Glu Val His Asn
                    275                 280                 285
Ala Lys Thr Lys Pro Arg Glu Glu Gln Tyr Asn Ser Thr Tyr Arg Val
                    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                    325                 330                 335
Thr Ile Ser Lys Ala Lys Gly Gln Pro Arg Glu Pro Gln Val Tyr Thr
                    340                 345                 350
Leu Pro Pro Ser Arg Asp Glu Leu Thr Lys Asn Gln Val Ser Leu Thr
                    355                 360                 365
Cys Leu Val Lys Gly Phe Tyr Pro Ser Asp Ile Ala Val Glu Trp Glu
                    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                    405                 410                 415
Ser Arg Trp Gln Gln Gly Asn Val Phe Ser Cys Ser Val Met His Glu
                    420                 425                 430
Ala Leu His Asn His Tyr Thr Gln Lys Ser Leu Ser Leu Ser Pro Gly
                    435                 440                 445
Lys

<210> SEQ ID NO 2
<211> LENGTH: 224
<212> TYPE: PRT
<213> ORGANISM: Homo sapiens

<400> SEQUENCE: 2
```

```
Glu Ala Gly Gln Val Met Thr Gln Thr Pro Leu Ser Leu Pro Val Thr
1               5                   10                  15

Leu Gly Gln Ser Ala Ser Ile Ser Cys Arg Ser Ser Gln Ser Leu Val
            20                  25                  30

Ser Ser Asp Gly Lys Thr Tyr Leu Asn Trp Phe His Gln Arg Pro Gly
        35                  40                  45

Gln Ser Pro Arg Arg Leu Ile Tyr Lys Val Ser Lys Arg Asp Ser Gly
    50                  55                  60

Val Pro Asp Arg Phe Ser Gly Ser Gly Ser Gly Thr Asp Phe Thr Leu
65                  70                  75                  80

Lys Ile Ser Arg Val Glu Ala Glu Asp Val Gly Val Tyr Phe Cys Met
                85                  90                  95

Gln Ala Thr His Trp Leu Trp Thr Phe Gly Gln Gly Thr Lys Val Glu
            100                 105                 110

Ile Lys Arg Thr Val Ala Ala Pro Ser Val Phe Ile Phe Pro Pro Ser
        115                 120                 125

Asp Glu Gln Leu Lys Ser Gly Thr Ala Ser Val Val Cys Leu Leu Asn
    130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
            180                 185                 190

Tyr Glu Lys His Lys Val Tyr Ala Cys Glu Val Thr His Gln Gly Leu
        195                 200                 205

Ser Ser Pro Val Thr Lys Ser Phe Asn Arg Gly Glu Cys Ala Ala Ala
    210                 215                 220

<210> SEQ ID NO 3
<211> LENGTH: 451
<212> TYPE: PRT
<213> ORGANISM: Homo sapiens

<400> SEQUENCE: 3

Glu Leu Ile Asn Leu Val Gln Ser Gly His Glu Val Lys Gln Pro Gly
1               5                   10                  15

Ala Ser Val Lys Leu Ser Cys Lys Ala Ser Gly Tyr Ser Phe Ser Ser
            20                  25                  30

Tyr Phe Val His Trp Val Arg Gln Ala Pro Gly Gln Gly Phe Glu Trp
        35                  40                  45

Met Gly Met Ile Asn Pro Arg Gly Gly Ser Thr Asn Tyr Ala Gln Lys
    50                  55                  60

Phe Gln Gly Arg Val Thr Met Thr Arg Glu Thr Ser Thr Thr Thr Val
65                  70                  75                  80

Tyr Met Glu Leu Ser Gly Leu Arg Ser Asp Asp Ser Ala Val Tyr Tyr
                85                  90                  95

Cys Ala Arg Val Asn Trp Ala Tyr Gly Asp Tyr Asp Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Gly Gly Thr
    130                 135                 140

Ala Ala Leu Gly Cys Leu Val Lys Asp Tyr Phe Pro Glu Pro Val Thr
145                 150                 155                 160
```

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Gln Thr Tyr Thr Cys Asn Val Asn
            195                 200                 205

His Lys Pro Ser Asn Thr Lys Val Asp Lys Thr Val Glu Arg Lys Cys
210                 215                 220

Trp Ala Arg His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 4
<211> LENGTH: 219
<212> TYPE: PRT
<213> ORGANISM: Homo sapiens

<400> SEQUENCE: 4

Glu Ala Gly Gln Gln Met Thr Gln Ser Pro Ser Ser Leu Ser Ala Ser
1               5                   10                  15

Val Gly Asp Arg Val Thr Ile Thr Cys Arg Ala Ser Gln Ser Ile Ala
            20                  25                  30

Arg Tyr Leu Asn Trp Tyr Gln Gln Arg Pro Gly Lys Ala Pro Lys Val
        35                  40                  45

Leu Ile Tyr Asp Ala Ser Ser Leu His Thr Gly Val Pro Ser Arg Phe
    50                  55                  60

Ser Gly Ser Gly Ser Gly Thr Asp Phe Thr Leu Thr Ile Ser Ser Leu
65                  70                  75                  80

```
Arg Pro Glu Asp Phe Ala Thr Tyr Tyr Cys Gln Gln Thr Tyr Ser Thr
                85                  90                  95

Pro Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Ala Ala Ala
    210                 215

<210> SEQ ID NO 5
<211> LENGTH: 451
<212> TYPE: PRT
<213> ORGANISM: Homo sapiens

<400> SEQUENCE: 5

Glu Leu Ile Asn Leu Val Glu Ser Gly Gly Leu Val Gln Pro Gly
1               5                   10                  15

Arg Ser Leu Arg Leu Ser Cys Ala Ala Ser Gly Phe Thr Phe Asp Asp
            20                  25                  30

Tyr Ala Met His Trp Val Arg Gln Val Ala Gly Lys Gly Leu Glu Trp
        35                  40                  45

Val Ser Gly Ile Asn Trp Asn Ser Ala Asn Ile Ala Tyr Ala Asp Ser
    50                  55                  60

Val Lys Gly Arg Phe Thr Ile Ser Arg Asp Asn Ala Lys Lys Leu Val
65                  70                  75                  80

Tyr Leu Gln Met His Ser Leu Arg Ala Glu Asp Thr Ala Val Tyr Tyr
                85                  90                  95

Cys Ala Lys Asp Met Tyr Gly Gly Gly Tyr Phe Phe Ala Lys Trp
                100                 105                 110

Gly Gln Gly Ser Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Leu Gly Thr Gln Thr Tyr Ile Cys Asn Val Asn
        195                 200                 205

His Lys Pro Ser Asn Thr Lys Val Asp Lys Thr Val Glu Arg Lys Cys
    210                 215                 220

Trp Ala Arg His Thr Cys Pro Pro Cys Pro Ala Pro Glu Leu Leu Gly
225                 230                 235                 240
```

```
Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 6
<211> LENGTH: 218
<212> TYPE: PRT
<213> ORGANISM: Homo sapiens

<400> SEQUENCE: 6

Glu Ala Gly Gln Gln Leu Thr Gln Ser Pro Ser Ser Leu Ser Ala Ser
1               5                   10                  15

Glu Gly Asp Arg Val Thr Ile Thr Cys Arg Ala Ser Gln Ser Ile Ser
            20                  25                  30

Asn Trp Leu Ala Trp Tyr Gln Gln Lys Pro Gly Lys Ala Pro Lys Leu
        35                  40                  45

Leu Ile Tyr Lys Ala Ser Ser Leu Glu Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Asp Asp Phe Ala Thr Tyr Tyr Cys Gln Gln Tyr Ser Gly Ser
                85                  90                  95

Ala Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160
```

```
Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val Thr Lys
            195                 200                 205

Ser Phe Asn Arg Gly Glu Cys Ala Ala Ala
        210                 215

<210> SEQ ID NO 7
<211> LENGTH: 454
<212> TYPE: PRT
<213> ORGANISM: Homo sapiens

<400> SEQUENCE: 7

Glu Leu Ile Asn Leu Val Glu Ser Gly Gly Gly Leu Ile Gln Pro Gly
1               5                   10                  15

Gly Ser Leu Arg Leu Ser Cys Thr Ala Ser Gly Phe Thr Val Asn Ser
            20                  25                  30

Met Tyr Met Asn Trp Phe Arg Gln Ala Pro Gly Lys Gly Leu Glu Trp
        35                  40                  45

Val Ser Ile Ile Tyr Ser Asp Gly Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Ser Ser Leu Arg Ala Glu Asp Thr Ala Val Tyr Tyr Cys
                85                  90                  95

Ala Arg Ala Pro Gln Tyr Asp Leu Trp Thr Gly Pro Leu Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Thr Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Trp Ala Arg His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320
```

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
            355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys
    450

<210> SEQ ID NO 8
<211> LENGTH: 219
<212> TYPE: PRT
<213> ORGANISM: Homo sapiens

<400> SEQUENCE: 8

Glu Ala Gly Gln Gln Leu Thr Gln Ser Pro Ser Ser Leu Ser Ala Ser
1               5                   10                  15

Val Gly Asp Arg Val Thr Ile Thr Cys Arg Ala Ser Gln Gly Ile Ser
            20                  25                  30

Arg Tyr Leu Ala Trp Tyr Gln Gln Lys Pro Gly Lys Ala Pro Lys Leu
            35                  40                  45

Leu Ile Tyr Ala Ala Ser Thr Leu Gln Ser Gly Val Pro Ser Arg Phe
50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Leu Asn Ser Tyr
            85                  90                  95

Pro Leu Thr Phe Gly Gly Gly Thr Arg Val Glu Val Lys Arg Thr Val
            100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
            195                 200                 205

Lys Ser Phe Asn Arg Gly Glu Cys Ala Ala Ala
210                 215

<210> SEQ ID NO 9

<211> LENGTH: 450
<212> TYPE: PRT
<213> ORGANISM: Homo sapiens

<400> SEQUENCE: 9

```
Leu Gln Glu Ser Gly Pro Gly Leu Val Lys Pro Ser Glu Thr Leu Ser
1               5                   10                  15

Leu Thr Cys Thr Val Ser Gly Gly Ser Ile Ser Gly Asn Tyr Trp Ser
            20                  25                  30

Trp Ile Arg Gln Pro Ala Gly Lys Gly Leu Glu Trp Ile Gly Arg Ile
        35                  40                  45

Tyr Ile Ser Gly Ser Thr Thr Tyr Lys Pro Ser Leu Lys Ser Arg Val
50                  55                  60

Thr Met Ser Val Asp Thr Ser Lys Asn Gln Phe Ser Leu Lys Leu Thr
65                  70                  75                  80

Ser Val Thr Ala Ala Asp Thr Ala Val Tyr Tyr Cys Ala Arg Asp Lys
                85                  90                  95

Asp Tyr Phe Ile Ser Gly Ser Tyr Tyr Asn Trp Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Thr Val Glu Arg Lys Cys Trp
210                 215                 220

Ala Arg His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 10
<211> LENGTH: 215
<212> TYPE: PRT
<213> ORGANISM: Homo sapiens

<400> SEQUENCE: 10

Glu Ala Gly Gln Val Leu Thr Gln Ser Pro Ala Thr Leu Ser Val Ser
1               5                   10                  15

Pro Gly Glu Arg Ala Thr Leu Ser Cys Arg Ala Ser Gln Ser Val Gly
                20                  25                  30

Ser Asn Leu Ala Trp Tyr Gln Gln Lys Pro Gly Gln Ala Pro Arg Leu
            35                  40                  45

Leu Ile Tyr Gly Ala Ser Thr Arg Ala Thr Gly Ile Pro Ala Arg Phe
        50                  55                  60

Ser Gly Ser Gly Ser Gly Thr Glu Phe Thr Leu Thr Ile Ser Ser Leu
65                  70                  75                  80

Gln Ser Glu Asp Phe Ala Val Tyr Tyr Cys Gln Gln Trp Thr Phe
                85                  90                  95

Gly Gln Gly Thr Lys Val Glu Ile Lys Arg Thr Val Ala Ala Pro Ser
                100                 105                 110

Val Phe Ile Phe Pro Pro Ser Asp Glu Gln Leu Lys Ser Gly Thr Ala
            115                 120                 125

Ser Val Val Cys Leu Leu Asn Asn Phe Tyr Pro Arg Glu Ala Lys Val
        130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Leu Tyr Ala Cys
                180                 185                 190

Glu Val Thr His Gln Gly Leu Ser Ser Pro Val Thr Lys Ser Phe Asn
            195                 200                 205

Arg Gly Glu Cys Ala Ala Ala
    210                 215

<210> SEQ ID NO 11
<211> LENGTH: 457
<212> TYPE: PRT
<213> ORGANISM: Homo sapiens

<400> SEQUENCE: 11

Glu Leu Ile Asn Leu Val Glu Ser Gly Gly Gly Val Val Arg Pro Gly
1               5                   10                  15

Arg Ser Leu Arg Leu Ser Cys Ala Ala Ser Gly Ile Ile Phe Ser Ser
                20                  25                  30

Tyr Thr Met His Trp Val Arg Gln Ala Pro Gly Lys Gly Leu Glu Trp
            35                  40                  45
```

Val Ala Leu Ile Ser Tyr Asp Gly Thr Asn Lys Asn Tyr Gly Asp Ser
 50                  55                  60

Val Thr Gly Arg Phe Thr Ile Ser Arg Asp Asn Ser Lys Asn Thr Leu
 65                  70                  75                  80

Tyr Leu Gln Met Asn Ser Leu Arg Pro Glu Asp Thr Ala Val Tyr Tyr
                 85                  90                  95

Cys Ala Arg Ala Arg Val Ile Val Pro Ala Gly Ser Asn Tyr Asn Gln
            100                 105                 110

Tyr Gly Met Asp Val Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Asn
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Thr Val Glu Arg Lys Cys Trp Ala Arg His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 12

```
<211> LENGTH: 215
<212> TYPE: PRT
<213> ORGANISM: Homo sapiens

<400> SEQUENCE: 12

Glu Ala Gly Gln Ser Val Leu Thr Gln Pro Pro Ser Val Ser Val Ser
1               5                   10                  15

Pro Gly Gln Thr Ala Ser Ile Thr Cys Ser Gly Asn Lys Leu Gly Asn
            20                  25                  30

Lys Tyr Ala Cys Trp Tyr Gln Gln Lys Pro Gly Gln Ser Pro Ile Leu
        35                  40                  45

Ile Ile Tyr Gln Asp Lys Lys Arg Pro Ser Gly Ile Pro Glu Arg Phe
    50                  55                  60

Ser Gly Ser Asn Ser Gly Asn Thr Ala Thr Leu Thr Ile Ser Gly Thr
65                  70                  75                  80

Gln Ala Met Asp Glu Ala Asp Tyr Tyr Cys Gln Ala Trp Asp Ser Asp
                85                  90                  95

Thr Val Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 13
<211> LENGTH: 120
<212> TYPE: PRT
<213> ORGANISM: Homo sapiens

<400> SEQUENCE: 13

Glu Leu Ile Asn Leu Gln Glu Ser Gly Pro Gly Leu Val Lys Pro Ser
1               5                   10                  15

Glu Thr Leu Ser Leu Thr Cys Thr Val Ser Gly Gly Ala Met Asn Ser
            20                  25                  30

His Phe Trp Ser Trp Ile Arg Gln Ser Pro Gly Lys Gly Leu Glu Trp
        35                  40                  45

Ile Gly Tyr Ile Tyr Ser Gly Thr Thr Asn Tyr Asp Pro Ser Leu
    50                  55                  60

Lys Ser Arg Val Ala Ile Ser Ile Asp Thr Ser Lys Lys Gln Phe Ser
65                  70                  75                  80

Leu Lys Leu Arg Ser Val Thr Ala Ala Asp Thr Ala Val Tyr Tyr Cys
                85                  90                  95

Ala Arg Gly Asp Met Val Thr Gly Asp Pro Gly Asp Tyr Trp Gly Gln
            100                 105                 110

Gly Thr Leu Val Thr Val Ser Ser
        115                 120
```

```
<210> SEQ ID NO 14
<211> LENGTH: 5
<212> TYPE: PRT
<213> ORGANISM: Homo sapiens

<400> SEQUENCE: 14

Ser His Phe Trp Ser
1               5

<210> SEQ ID NO 15
<211> LENGTH: 16
<212> TYPE: PRT
<213> ORGANISM: Homo sapiens

<400> SEQUENCE: 15

Tyr Ile Tyr Ser Gly Gly Thr Thr Asn Tyr Asp Pro Ser Leu Lys Ser
1               5                   10                  15

<210> SEQ ID NO 16
<211> LENGTH: 11
<212> TYPE: PRT
<213> ORGANISM: Homo sapiens

<400> SEQUENCE: 16

Gly Asp Met Val Thr Gly Asp Pro Gly Asp Tyr
1               5                   10

<210> SEQ ID NO 17
<211> LENGTH: 115
<212> TYPE: PRT
<213> ORGANISM: Homo sapiens

<400> SEQUENCE: 17

Glu Ala Gly Gln Val Met Thr Gln Thr Pro Leu Ser Leu Pro Val Thr
1               5                   10                  15

Leu Gly Gln Ser Ala Ser Ile Ser Cys Arg Ser Ser Gln Ser Leu Val
            20                  25                  30

Ser Ser Asp Gly Lys Thr Tyr Leu Asn Trp Phe His Gln Arg Pro Gly
        35                  40                  45

Gln Ser Pro Arg Arg Leu Ile Tyr Lys Val Ser Lys Arg Asp Ser Gly
    50                  55                  60

Val Pro Asp Arg Phe Ser Gly Ser Gly Ser Gly Thr Asp Phe Thr Leu
65                  70                  75                  80

Lys Ile Ser Arg Val Glu Ala Glu Asp Val Gly Val Tyr Phe Cys Met
                85                  90                  95

Gln Ala Thr His Trp Leu Trp Thr Phe Gly Gln Gly Thr Lys Val Glu
            100                 105                 110

Ile Lys Arg
        115

<210> SEQ ID NO 18
<211> LENGTH: 16
<212> TYPE: PRT
<213> ORGANISM: Homo sapiens

<400> SEQUENCE: 18

Arg Ser Ser Gln Ser Leu Val Ser Ser Asp Gly Lys Thr Tyr Leu Asn
1               5                   10                  15

<210> SEQ ID NO 19
<211> LENGTH: 7
<212> TYPE: PRT
```

<213> ORGANISM: Homo sapiens

<400> SEQUENCE: 19

Lys Val Ser Lys Arg Asp Ser
1               5

<210> SEQ ID NO 20
<211> LENGTH: 9
<212> TYPE: PRT
<213> ORGANISM: Homo sapiens

<400> SEQUENCE: 20

Met Gln Ala Thr His Trp Leu Trp Thr
1               5

<210> SEQ ID NO 21
<211> LENGTH: 122
<212> TYPE: PRT
<213> ORGANISM: Homo sapiens

<400> SEQUENCE: 21

Glu Leu Ile Asn Leu Val Gln Ser Gly His Glu Val Lys Gln Pro Gly
1               5                   10                  15

Ala Ser Val Lys Leu Ser Cys Lys Ala Ser Gly Tyr Ser Phe Ser Ser
            20                  25                  30

Tyr Phe Val His Trp Val Arg Gln Ala Pro Gly Gln Gly Phe Glu Trp
        35                  40                  45

Met Gly Met Ile Asn Pro Arg Gly Gly Ser Thr Asn Tyr Ala Gln Lys
    50                  55                  60

Phe Gln Gly Arg Val Thr Met Thr Arg Glu Thr Ser Thr Thr Thr Val
65                  70                  75                  80

Tyr Met Glu Leu Ser Gly Leu Arg Ser Asp Asp Ser Ala Val Tyr Tyr
                85                  90                  95

Cys Ala Arg Val Asn Trp Ala Tyr Gly Asp Tyr Asp Phe Asp Tyr Trp
            100                 105                 110

Gly Gln Gly Thr Leu Val Thr Val Ser Ser
        115                 120

<210> SEQ ID NO 22
<211> LENGTH: 5
<212> TYPE: PRT
<213> ORGANISM: Homo sapiens

<400> SEQUENCE: 22

Ser Tyr Phe Val His
1               5

<210> SEQ ID NO 23
<211> LENGTH: 17
<212> TYPE: PRT
<213> ORGANISM: Homo sapiens

<400> SEQUENCE: 23

Met Ile Asn Pro Arg Gly Gly Ser Thr Asn Tyr Ala Gln Lys Phe Gln
1               5                   10                  15

Gly

<210> SEQ ID NO 24
<211> LENGTH: 12
<212> TYPE: PRT
<213> ORGANISM: Homo sapiens

```
<400> SEQUENCE: 24

Val Asn Trp Ala Tyr Gly Asp Tyr Asp Phe Asp Tyr
1               5                   10

<210> SEQ ID NO 25
<211> LENGTH: 110
<212> TYPE: PRT
<213> ORGANISM: Homo sapiens

<400> SEQUENCE: 25

Glu Ala Gly Gln Gln Met Thr Gln Ser Pro Ser Ser Leu Ser Ala Ser
1               5                   10                  15

Val Gly Asp Arg Val Thr Ile Thr Cys Arg Ala Ser Gln Ser Ile Ala
            20                  25                  30

Arg Tyr Leu Asn Trp Tyr Gln Gln Arg Pro Gly Lys Ala Pro Lys Val
        35                  40                  45

Leu Ile Tyr Asp Ala Ser Ser Leu His Thr Gly Val Pro Ser Arg Phe
    50                  55                  60

Ser Gly Ser Gly Ser Gly Thr Asp Phe Thr Leu Thr Ile Ser Ser Leu
65                  70                  75                  80

Arg Pro Glu Asp Phe Ala Thr Tyr Tyr Cys Gln Gln Thr Tyr Ser Thr
                85                  90                  95

Pro Leu Thr Phe Gly Gly Gly Thr Lys Val Glu Ile Lys Arg
            100                 105                 110

<210> SEQ ID NO 26
<211> LENGTH: 11
<212> TYPE: PRT
<213> ORGANISM: Homo sapiens

<400> SEQUENCE: 26

Arg Ala Ser Gln Ser Ile Ala Arg Tyr Leu Asn
1               5                   10

<210> SEQ ID NO 27
<211> LENGTH: 7
<212> TYPE: PRT
<213> ORGANISM: Homo sapiens

<400> SEQUENCE: 27

Asp Ala Ser Ser Leu His Thr
1               5

<210> SEQ ID NO 28
<211> LENGTH: 9
<212> TYPE: PRT
<213> ORGANISM: Homo sapiens

<400> SEQUENCE: 28

Gln Gln Thr Tyr Ser Thr Pro Leu Thr
1               5

<210> SEQ ID NO 29
<211> LENGTH: 122
<212> TYPE: PRT
<213> ORGANISM: Homo sapiens

<400> SEQUENCE: 29

Glu Leu Ile Asn Leu Val Glu Ser Gly Gly Gly Leu Val Gln Pro Gly
1               5                   10                  15

Arg Ser Leu Arg Leu Ser Cys Ala Ala Ser Gly Phe Thr Phe Asp Asp
            20                  25                  30
```

```
Tyr Ala Met His Trp Val Arg Gln Val Ala Gly Lys Gly Leu Glu Trp
             35                  40                  45
Val Ser Gly Ile Asn Trp Asn Ser Ala Asn Ile Ala Tyr Ala Asp Ser
 50                  55                  60
Val Lys Gly Arg Phe Thr Ile Ser Arg Asp Asn Ala Lys Lys Leu Val
 65                  70                  75                  80
Tyr Leu Gln Met His Ser Leu Arg Ala Glu Asp Thr Ala Val Tyr Tyr
                 85                  90                  95
Cys Ala Lys Asp Met Tyr Gly Gly Gly Tyr Phe Phe Ala Lys Trp
            100                 105                 110
Gly Gln Gly Ser Leu Val Thr Val Ser Ser
            115                 120
```

<210> SEQ ID NO 30
<211> LENGTH: 5
<212> TYPE: PRT
<213> ORGANISM: Homo sapiens

<400> SEQUENCE: 30

```
Asp Tyr Ala Met His
 1               5
```

<210> SEQ ID NO 31
<211> LENGTH: 17
<212> TYPE: PRT
<213> ORGANISM: Homo sapiens

<400> SEQUENCE: 31

```
Gly Ile Asn Trp Asn Ser Ala Asn Ile Ala Tyr Ala Asp Ser Val Lys
 1               5                  10                  15
Gly
```

<210> SEQ ID NO 32
<211> LENGTH: 12
<212> TYPE: PRT
<213> ORGANISM: Homo sapiens

<400> SEQUENCE: 32

```
Asp Met Tyr Gly Gly Gly Tyr Phe Phe Ala Lys
 1               5                  10
```

<210> SEQ ID NO 33
<211> LENGTH: 109
<212> TYPE: PRT
<213> ORGANISM: Homo sapiens

<400> SEQUENCE: 33

```
Glu Ala Gly Gln Gln Leu Thr Gln Ser Pro Ser Ser Leu Ser Ala Ser
 1               5                  10                  15
Glu Gly Asp Arg Val Thr Ile Thr Cys Arg Ala Ser Gln Ser Ile Ser
            20                  25                  30
Asn Trp Leu Ala Trp Tyr Gln Gln Lys Pro Gly Lys Ala Pro Lys Leu
        35                  40                  45
Leu Ile Tyr Lys Ala Ser Ser Leu Glu Ser Gly Val Pro Ser Arg Phe
 50                  55                  60
Ser Gly Ser Gly Ser Gly Thr Glu Phe Thr Leu Thr Ile Ser Ser Leu
 65                  70                  75                  80
Gln Pro Asp Asp Phe Ala Thr Tyr Tyr Cys Gln Gln Tyr Ser Gly Ser
                 85                  90                  95
```

```
Ala Thr Phe Gly Gln Gly Thr Lys Val Glu Ile Lys Arg
            100                 105
```

<210> SEQ ID NO 34
<211> LENGTH: 11
<212> TYPE: PRT
<213> ORGANISM: Homo sapiens

<400> SEQUENCE: 34

```
Arg Ala Ser Gln Ser Ile Ser Asn Trp Leu Ala
1               5                   10
```

<210> SEQ ID NO 35
<211> LENGTH: 7
<212> TYPE: PRT
<213> ORGANISM: Homo sapiens

<400> SEQUENCE: 35

```
Lys Ala Ser Ser Leu Glu Ser
1               5
```

<210> SEQ ID NO 36
<211> LENGTH: 8
<212> TYPE: PRT
<213> ORGANISM: Homo sapiens

<400> SEQUENCE: 36

```
Gln Gln Tyr Ser Gly Ser Ala Thr
1               5
```

<210> SEQ ID NO 37
<211> LENGTH: 125
<212> TYPE: PRT
<213> ORGANISM: Homo sapiens

<400> SEQUENCE: 37

```
Glu Leu Ile Asn Leu Val Glu Ser Gly Gly Leu Ile Gln Pro Gly
1               5                   10                  15

Gly Ser Leu Arg Leu Ser Cys Thr Ala Ser Gly Phe Thr Val Asn Ser
            20                  25                  30

Met Tyr Met Asn Trp Phe Arg Gln Ala Pro Gly Lys Gly Leu Glu Trp
        35                  40                  45

Val Ser Ile Ile Tyr Ser Asp Gly Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Ser Ser Leu Arg Ala Glu Asp Thr Ala Val Tyr Tyr Cys
                85                  90                  95

Ala Arg Ala Pro Gln Tyr Asp Leu Trp Thr Gly Pro Leu Tyr Gly Met
            100                 105                 110

Asp Val Trp Gly Gln Gly Thr Thr Val Thr Val Ser Ser
            115                 120                 125
```

<210> SEQ ID NO 38
<211> LENGTH: 5
<212> TYPE: PRT
<213> ORGANISM: Homo sapiens

<400> SEQUENCE: 38

```
Ser Met Tyr Met Asn
1               5
```

<210> SEQ ID NO 39
<211> LENGTH: 16
<212> TYPE: PRT
<213> ORGANISM: Homo sapiens

<400> SEQUENCE: 39

Ile Ile Tyr Ser Asp Gly Ser Thr Phe Tyr Ala Asp Ser Val Lys Gly
1               5                   10                  15

<210> SEQ ID NO 40
<211> LENGTH: 16
<212> TYPE: PRT
<213> ORGANISM: Homo sapiens

<400> SEQUENCE: 40

Ala Pro Gln Tyr Asp Leu Trp Thr Gly Pro Leu Tyr Gly Met Asp Val
1               5                   10                  15

<210> SEQ ID NO 41
<211> LENGTH: 110
<212> TYPE: PRT
<213> ORGANISM: Homo sapiens

<400> SEQUENCE: 41

Glu Ala Gly Gln Gln Leu Thr Gln Ser Pro Ser Ser Leu Ser Ala Ser
1               5                   10                  15

Val Gly Asp Arg Val Thr Ile Thr Cys Arg Ala Ser Gln Gly Ile Ser
            20                  25                  30

Arg Tyr Leu Ala Trp Tyr Gln Gln Lys Pro Gly Lys Ala Pro Lys Leu
        35                  40                  45

Leu Ile Tyr Ala Ala Ser Thr Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gly Gln Leu Asn Ser Tyr
                85                  90                  95

Pro Leu Thr Phe Gly Gly Gly Thr Arg Val Glu Val Lys Arg
            100                 105                 110

<210> SEQ ID NO 42
<211> LENGTH: 11
<212> TYPE: PRT
<213> ORGANISM: Homo sapiens

<400> SEQUENCE: 42

Arg Ala Ser Gln Gly Ile Ser Arg Tyr Leu Ala
1               5                   10

<210> SEQ ID NO 43
<211> LENGTH: 7
<212> TYPE: PRT
<213> ORGANISM: Homo sapiens

<400> SEQUENCE: 43

Ala Ala Ser Thr Leu Gln Ser
1               5

<210> SEQ ID NO 44
<211> LENGTH: 9
<212> TYPE: PRT
<213> ORGANISM: Homo sapiens

<400> SEQUENCE: 44

```
Gln Gln Leu Asn Ser Tyr Pro Leu Thr
1               5
```

```
<210> SEQ ID NO 45
<211> LENGTH: 121
<212> TYPE: PRT
<213> ORGANISM: Homo sapiens

<400> SEQUENCE: 45
```

```
Leu Gln Glu Ser Gly Pro Gly Leu Val Lys Pro Ser Glu Thr Leu Ser
1               5                   10                  15

Leu Thr Cys Thr Val Ser Gly Gly Ser Ile Ser Gly Asn Tyr Trp Ser
            20                  25                  30

Trp Ile Arg Gln Pro Ala Gly Lys Gly Leu Glu Trp Ile Gly Arg Ile
        35                  40                  45

Tyr Ile Ser Gly Ser Thr Thr Tyr Lys Pro Ser Leu Lys Ser Arg Val
    50                  55                  60

Thr Met Ser Val Asp Thr Ser Lys Asn Gln Phe Ser Leu Lys Leu Thr
65                  70                  75                  80

Ser Val Thr Ala Ala Asp Thr Ala Val Tyr Tyr Cys Ala Arg Asp Lys
                85                  90                  95

Asp Tyr Phe Ile Ser Gly Ser Tyr Tyr Asn Trp Phe Asp Pro Trp Gly
            100                 105                 110

Gln Gly Thr Leu Val Thr Val Ser Ser
        115                 120
```

```
<210> SEQ ID NO 46
<211> LENGTH: 5
<212> TYPE: PRT
<213> ORGANISM: Homo sapiens

<400> SEQUENCE: 46
```

```
Gly Asn Tyr Trp Ser
1               5
```

```
<210> SEQ ID NO 47
<211> LENGTH: 16
<212> TYPE: PRT
<213> ORGANISM: Homo sapiens

<400> SEQUENCE: 47
```

```
Arg Ile Tyr Ile Ser Gly Ser Thr Thr Tyr Lys Pro Ser Leu Lys Ser
1               5                   10                  15
```

```
<210> SEQ ID NO 48
<211> LENGTH: 16
<212> TYPE: PRT
<213> ORGANISM: Homo sapiens

<400> SEQUENCE: 48
```

```
Asp Lys Asp Tyr Phe Ile Ser Gly Ser Tyr Tyr Asn Trp Phe Asp Pro
1               5                   10                  15
```

```
<210> SEQ ID NO 49
<211> LENGTH: 106
<212> TYPE: PRT
<213> ORGANISM: Homo sapiens

<400> SEQUENCE: 49
```

```
Glu Ala Gly Gln Val Leu Thr Gln Ser Pro Ala Thr Leu Ser Val Ser
1               5                   10                  15

Pro Gly Glu Arg Ala Thr Leu Ser Cys Arg Ala Ser Gln Ser Val Gly
```

```
                         20                  25                  30
Ser Asn Leu Ala Trp Tyr Gln Gln Lys Pro Gly Gln Ala Pro Arg Leu
         35                  40                  45

Leu Ile Tyr Gly Ala Ser Thr Arg Ala Thr Gly Ile Pro Ala Arg Phe
     50                  55                  60

Ser Gly Ser Gly Ser Gly Thr Glu Phe Thr Leu Thr Ile Ser Ser Leu
65                  70                  75                  80

Gln Ser Glu Asp Phe Ala Val Tyr Tyr Cys Gln Gln Gly Trp Thr Phe
                 85                  90                  95

Gly Gln Gly Thr Lys Val Glu Ile Lys Arg
                100                 105

<210> SEQ ID NO 50
<211> LENGTH: 11
<212> TYPE: PRT
<213> ORGANISM: Homo sapiens

<400> SEQUENCE: 50

Arg Ala Ser Gln Ser Val Gly Ser Asn Leu Ala
1               5                   10

<210> SEQ ID NO 51
<211> LENGTH: 7
<212> TYPE: PRT
<213> ORGANISM: Homo sapiens

<400> SEQUENCE: 51

Gly Ala Ser Thr Arg Ala Thr
1               5

<210> SEQ ID NO 52
<211> LENGTH: 5
<212> TYPE: PRT
<213> ORGANISM: Homo sapiens

<400> SEQUENCE: 52

Gln Gln Gly Trp Thr
1               5

<210> SEQ ID NO 53
<211> LENGTH: 128
<212> TYPE: PRT
<213> ORGANISM: Homo sapiens

<400> SEQUENCE: 53

Glu Leu Ile Asn Leu Val Glu Ser Gly Gly Gly Val Val Arg Pro Gly
1               5                   10                  15

Arg Ser Leu Arg Leu Ser Cys Ala Ala Ser Gly Ile Ile Phe Ser Ser
            20                  25                  30

Tyr Thr Met His Trp Val Arg Gln Ala Pro Gly Lys Gly Leu Glu Trp
         35                  40                  45

Val Ala Leu Ile Ser Tyr Asp Gly Thr Asn Lys Asn Tyr Gly Asp Ser
     50                  55                  60

Val Thr Gly Arg Phe Thr Ile Ser Arg Asp Asn Ser Lys Asn Thr Leu
65                  70                  75                  80

Tyr Leu Gln Met Asn Ser Leu Arg Pro Glu Asp Thr Ala Val Tyr Tyr
                 85                  90                  95

Cys Ala Arg Ala Arg Val Ile Val Pro Ala Gly Ser Asn Tyr Asn Gln
                100                 105                 110

Tyr Gly Met Asp Val Trp Gly Gln Gly Thr Thr Val Thr Val Ser Ser
```

```
              115                 120                 125
```

<210> SEQ ID NO 54
<211> LENGTH: 5
<212> TYPE: PRT
<213> ORGANISM: Homo sapiens

<400> SEQUENCE: 54

```
Ser Tyr Thr Met His
1               5
```

<210> SEQ ID NO 55
<211> LENGTH: 17
<212> TYPE: PRT
<213> ORGANISM: Homo sapiens

<400> SEQUENCE: 55

```
Leu Ile Ser Tyr Asp Gly Thr Asn Lys Asn Tyr Gly Asp Ser Val Thr
1               5                   10                  15

Gly
```

<210> SEQ ID NO 56
<211> LENGTH: 18
<212> TYPE: PRT
<213> ORGANISM: Homo sapiens

<400> SEQUENCE: 56

```
Ala Arg Val Ile Val Pro Ala Gly Ser Asn Tyr Asn Gln Tyr Gly Met
1               5                   10                  15

Asp Val
```

<210> SEQ ID NO 57
<211> LENGTH: 110
<212> TYPE: PRT
<213> ORGANISM: Homo sapiens

<400> SEQUENCE: 57

```
Glu Ala Gly Gln Ser Val Leu Thr Gln Pro Pro Ser Val Ser Val Ser
1               5                   10                  15

Pro Gly Gln Thr Ala Ser Ile Thr Cys Ser Gly Asn Lys Leu Gly Asn
                20                  25                  30

Lys Tyr Ala Cys Trp Tyr Gln Gln Lys Pro Gly Gln Ser Pro Ile Leu
            35                  40                  45

Ile Ile Tyr Gln Asp Lys Lys Arg Pro Ser Gly Ile Pro Glu Arg Phe
        50                  55                  60

Ser Gly Ser Asn Ser Gly Asn Thr Ala Thr Leu Thr Ile Ser Gly Thr
65                  70                  75                  80

Gln Ala Met Asp Glu Ala Asp Tyr Tyr Cys Gln Ala Trp Asp Ser Asp
                85                  90                  95

Thr Val Val Phe Gly Gly Gly Thr Lys Leu Thr Val Leu Gly
            100                 105                 110
```

<210> SEQ ID NO 58
<211> LENGTH: 11
<212> TYPE: PRT
<213> ORGANISM: Homo sapiens

<400> SEQUENCE: 58

```
Ser Gly Asn Lys Leu Gly Asn Lys Tyr Ala Cys
1               5                   10
```

<210> SEQ ID NO 59
<211> LENGTH: 7
<212> TYPE: PRT
<213> ORGANISM: Homo sapiens

<400> SEQUENCE: 59

Gln Asp Lys Lys Arg Pro Ser
1               5

<210> SEQ ID NO 60
<211> LENGTH: 9
<212> TYPE: PRT
<213> ORGANISM: Homo sapiens

<400> SEQUENCE: 60

Gln Ala Trp Asp Ser Asp Thr Val Val
1               5

<210> SEQ ID NO 61
<211> LENGTH: 1350
<212> TYPE: DNA
<213> ORGANISM: Homo sapiens

<400> SEQUENCE: 61

```
gagttaatta atctgcagga gtcgggccca ggactggtga agccctcgga gaccctgtcc      60
ctcacctgca ctgtctctgg tggcgccatg aacagtcact tctggagttg gatccggcag     120
tccccaggga aggactggag gtggattggg tatatctatt ccggtgggac taccaactac     180
gacccctccc tcaagagtcg agtcgccatt tcaatagaca cgtccaagaa gcagttctcc     240
ctgaaattga ggtctgtgac cgccgcggac acggccgtgt attattgtgc gagaggagac     300
atggtgactg gggatccggg cgactactgg ggccagggca ccctggtcac cgtctcctca     360
gcctccacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagac agttgagcgc     660
aaatgttggg cgcgccacac atgcccaccg tgcccagcac ctgaactcct ggggggaccg     720
tcagtcttcc tcttcccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020
gccaaagggc agccccgaga accacaggtg tacaccctgc ccccatcccg ggatgagctg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaatga                                     1350
```

<210> SEQ ID NO 62
<211> LENGTH: 675
<212> TYPE: DNA
<213> ORGANISM: Homo sapiens

<400> SEQUENCE: 62

```
gaggccggcc aggtgatgac tcagactcca ctctccctgc ccgtcaccct tggacagtcg      60
gcctccatct cctgcaggtc tagtcaaagc ctcgtatcca gtgatggaaa gacctacttg     120
aattggtttc accagaggcc aggccaatct ccaaggcgcc taatttataa ggtttctaag     180
cgggactctg gggtccccga cagattcagc ggcagtgggt caggcactga tttcacactg     240
aaaatcagca gggtggaggc tgaggatgtt ggggtttatt tctgcatgca agctacacac     300
tggctttgga cgttcggcca agggaccaag gtggaaatca aacgaactgt ggctgcacca     360
tctgtcttca tcttcccgcc atctgatgag cagttgaaat ctggaactgc ctctgttgtg     420
tgcctgctga ataacttcta tcccagagag gccaaagtac agtggaaggt ggataacgcc     480
ctccaatcgg gtaactccca ggagagtgtc acagagcagg acagcaagga cagcacctac     540
agcctcagca gcaccctgac gctgagcaaa gcagactacg agaaacacaa agtctacgcc     600
tgcgaagtca cccatcaggg cctgagctcg cccgtcacaa agagcttcaa caggggagag     660
tgtgcggccg catga                                                      675
```

<210> SEQ ID NO 63
<211> LENGTH: 1356
<212> TYPE: DNA
<213> ORGANISM: Homo sapiens

<400> SEQUENCE: 63

```
gagttaatta atctggtgca gtctggccat gaggtgaagc agcctggggc ctcagtgaag      60
ctttcctgca aggcatctgg atactccttc agcagttact ttgtccactg ggtgcgacag     120
gcccctggac aagggtttga gtggatggga atgatcaacc ctcgtggtgg tagcacaaac     180
tacgcacaga gttccagggg cagagtcacc atgaccaggg agacgtccac gaccacggtc     240
tacatggagc tgagcggcct gagaagtgat gactcggccg tttattactg tgctagagtc     300
aattgggcct acgtgactac cgactttgac tactggggcc agggaaccct ggtcaccgtc     360
tcctcagctt ccaccaaggg cccatcggtc ttccccctgg cgccctgctc caggagcacc     420
tctgggggca cagcggccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca cctgcaacgt gaatcacaag cccagcaaca ccaaggtgga caagacagtt     660
gagcgcaaat gttggcgcg ccacacatgc ccaccgtgcc cagcacctga actcctgggg     720
ggaccgtcag tcttcctctt ccccccaaaa cccaaggaca cctcatgat c tcccggacc     780
cctgaggtca catgcgtggt ggtggacgtg agccacgaag accctgaggt caagttcaac     840
tggtacgtgg acggcgtgga ggtgcataat gccaagacaa agccgcggga ggagcagtac     900
aacagcacgt accgtgtggt cagcgtcctc accgtcctgc accaggactg gctgaatggc     960
aaggagtaca gtgcaaggt ctccaacaaa gccctcccag cccccatcga gaaaaccatc    1020
tccaaagcca aagggcagcc ccgagaacca caggtgtaca ccctgccccc atcccgggat    1080
gagctgacca agaaccaggt cagcctgacc tgcctggtca aaggcttcta tcccagcgac    1140
atcgccgtgg agtgggagag caatgggcag ccggagaaca actacaagac cacgcctccc    1200
gtgctggact ccgacggctc cttcttcctc tacagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaatga                              1356
```

<210> SEQ ID NO 64
<211> LENGTH: 660
<212> TYPE: DNA
<213> ORGANISM: Homo sapiens

<400> SEQUENCE: 64

```
gaggccggcc agcagatgac ccagtctcca tcctccctgt ctgcatctgt aggagacaga      60
gtcaccatca cttgccgggc aagtcagagc attgccaggt atttaaattg gtatcagcag     120
agaccaggga aagcccccaa ggtcctgatc tatgatgcat ccagtctaca tactggggtc     180
ccatcaaggt tcagtggcag tggatctggg acagatttca ctctcaccat cagcagtctg     240
cgccctgaag attttgcaac ttactactgt caacagactt acagtactcc cctcactttc     300
ggcggaggga ccaaggtgga gatcaaacga actgtggctg caccatctgt cttcatcttc     360
ccgccatctg atgagcagtt gaaatctgga actgcctctg ttgtgtgcct gctgaataac     420
ttctatccca gagaggccaa agtacagtgg aaggtggata acgccctcca atcgggtaac     480
tcccaggaga gtgtcacaga gcaggacagc aaggacagca cctacagcct cagcagcacc     540
ctgacgctga gcaaagcaga ctacgagaaa cacaaagtct acgcctgcga agtcaccat     600
cagggcctga gctcgcccgt cacaaagagc ttcaacaggg gagagtgtgc ggccgcatga     660
```

<210> SEQ ID NO 65
<211> LENGTH: 1356
<212> TYPE: DNA
<213> ORGANISM: Homo sapiens

<400> SEQUENCE: 65

```
gagttaatta atctggtgga gtctggggga ggcttggtac agcctggcag gtccctgaga      60
ctctcctgtg cagcctctgg attcaccttt gatgattatg ccatgcactg ggtccggcaa     120
gttgcaggga agggcctgga gtgggtctca ggtattaatt ggaatagtgc taacatcgcc     180
tatgcggact ctgtgaaggg ccgattcacc atctccagag acaacgccaa gaaattagtc     240
tatctacaga tgcacagtct gagagctgag gacacggccg tatattactg tgcaaaagat     300
atgtatggcg gtggcgggta cttctttgcc aagtggggcc agggatccct ggtcaccgtc     360
tcctcagcct ccaccaaggg cccatcggtc ttccccctgg cacccctctc caagagcacc     420
tctgggggca cagcggccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagacagtt     660
gagcgcaaat gttgggcgcg ccacacatgc ccaccgtgcc cagcacctga actcctgggg     720
ggaccgtcag tcttcctctt ccccccaaaa cccaaggaca cctcatgat ctccccggacc     780
cctgaggtca catgcgtggt ggtggacgtg agccacgaag accctgaggt caagttcaac     840
tggtacgtgg acggcgtgga ggtgcataat gccaagacaa agccgcggga ggagcagtac     900
aacagcacgt accgtgtggt cagcgtcctc accgtcctgc accaggactg gctgaatggc     960
aaggagtaca gtgcaaggt ctccaacaaa gccctcccag ccccccatcga gaaaaccatc    1020
tccaaagcca aagggcagcc ccgagaacca caggtgtaca ccctgccccc atcccgggat    1080
gagctgacca agaaccaggt cagcctgacc tgcctggtca aaggcttcta tcccagcgac    1140
atcgccgtgg agtgggagag caatgggcag ccggagaaca actacaagac cacgcctccc    1200
gtgctggact ccgacggctc cttcttcctc tacagcaagc tcaccgtgga caagagcagg    1260
```

```
tggcagcagg ggaacgtctt ctcatgctcc gtgatgcatg aggctctgca caaccactac    1320
acgcagaaga gcctctccct gtctccgggt aaatga                              1356

<210> SEQ ID NO 66
<211> LENGTH: 657
<212> TYPE: DNA
<213> ORGANISM: Homo sapiens

<400> SEQUENCE: 66
gaggccggcc agcagttgac ccagtctcca tcctccctgt ctgcatctga aggagacaga      60
gtcaccatca cttgccgggc cagtcagagt attagtaatt ggttggcctg gtatcagcag     120
aaaccaggga aagcccctaa actcctgatc tataaggcat ctagtttaga aagtggggtc     180
ccatccaggt tcagcggcag tggatctggg acagaattca ctctcaccat cagcagcctg     240
cagcctgatg atttcgcaac ttattattgc caacagtata gtggttctgc gacgttcggc     300
caagggacca aggtggagat caaacgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag acagcacct acagcctcag cagcaccctg      540
acgctgagca agcagacta cgagaaacac aaactctacg cctgcgaagt cacccatcag      600
ggcctgagct cgcccgtcac aaagagcttc aacaggggag agtgtgcggc cgcatga        657

<210> SEQ ID NO 67
<211> LENGTH: 1365
<212> TYPE: DNA
<213> ORGANISM: Homo sapiens

<400> SEQUENCE: 67
gagttaatta atctggtgga gtctggggga ggcttgatcc agcctggggg gtccctgaga      60
ctctcctgta cagcctctgg gttcacggtc aatagcatgt acatgaactg gttccgccag     120
gctccaggga aggggctgga gtgggtctca attatttata gcgatggtag cacattctac     180
gcagactccg tgaagggccg attcaccatc tccagagaca attccaagaa caccctgtat     240
cttcaactga gcagcctgag agccgaggac acggccgtat attactgtgc gagagcgccc     300
cagtacgatt tgtggactgg tccccttac gggatggacg tctggggcca agggaccacg      360
gtcaccgtct cctcagcctc caccaagggc ccatcggtct tccccctggc gccctgctcc     420
aggagcacct ccgagagcac agcggccctg ggctgcctgg tcaaggacta cttccccgaa     480
ccggtgacgg tgtcgtggaa ctcaggcgct ctgaccagcg gcgtgcacac cttcccggct     540
gtcctacagt cctcaggact ctactccctc agcagcgtgg tgaccgtgac ctccagcaac     600
ttcggcaccc agacctacac ctgcaacgta gatcacaagc ccagcaacac caaggtggac     660
aagacagttg agcgcaaatg ttgggcgcgc cacacatgcc caccgtgccc agcacctgaa     720
ctcctggggg gaccgtcagt cttcctcttc cccccaaaac ccaaggacac cctcatgatc     780
tcccggaccc ctgaggtcac atgcgtggtg gtggacgtga gccacgaaga ccctgaggtc     840
aagttcaact ggtacgtgga cggcgtggag gtgcataatg ccaagacaaa gccgcgggag     900
gagcagtaca acagcacgta ccgtgtggtc agcgtcctca ccgtcctgca ccaggactgg     960
ctgaatggca aggagtacaa gtgcaaggtc tccaacaaag cccteccagc ccccatcgag    1020 aaaaccatct ccaaagccaa agggcagccc cgagaaccac aggtgtacac cctgccccca    1080
tcccgggatg agctgaccaa gaaccaggtc agcctgacct gcctggtcaa aggcttctat    1140
```

```
cccagcgaca tcgccgtgga gtgggagagc aatgggcagc cggagaacaa ctacaagacc    1200
acgcctcccg tgctggactc cgacggctcc ttcttcctct acagcaagct caccgtggac    1260
aagagcaggt ggcagcaggg gaacgtcttc tcatgctccg tgatgcatga ggctctgcac    1320
aaccactaca cgcagaagag cctctccctg tctccgggta aatga                    1365

<210> SEQ ID NO 68
<211> LENGTH: 660
<212> TYPE: DNA
<213> ORGANISM: Homo sapiens

<400> SEQUENCE: 68
gaggccggcc agcagttgac ccagtctcca tcctccctgt ctgcatctgt aggagacaga      60
gtcaccatca cttgccgggc cagtcagggc attagtcgtt atttagcctg gtatcagcaa     120
aaaccaggga aagcccctaa gctcctgatc tatgctgcat ccactttgca aagtggggtc     180
ccatcaaggt tcagcggcag tggatctggg acagatttca ctctcaccat cagcagcctg     240
cagcctgaag attttgcaac ttattactgt caacagctta atagttaccc actcactttc     300
ggcggaggga ccagggtgga ggtcaaacga actgtggctg caccatctgt cttcatcttc     360
ccgccatctg atgagcagtt gaaatctgga actgcctctg ttgcgtgcct gctgaataac     420
ttctatccca gagaggccaa agtacagtgg aaggtggata acgccctcca atcgggtaac     480
tcccaggaga gtgtcacaga gcaggacagc aaggacagca cctacagcct cagcagcacc     540
ctgacgctga gcaaagcaga ctacgagaaa cacaaagtct acgcctgcga agtcacccat     600
cagggcctga gctcgcccgt cacaaagagc ttcaacaggg gagagtgtgc ggccgcatga     660

<210> SEQ ID NO 69
<211> LENGTH: 1353
<212> TYPE: DNA
<213> ORGANISM: Homo sapiens

<400> SEQUENCE: 69
ctgcaggagt cgggcccagg actggtgaag ccttcggaga ccctgtccct cacctgcact      60
gtctctggtg gctccatcag tggaaattac tggagctgga tccggcagcc cgccgggaag     120
ggactggagt ggattgggcg tatctatatt agtgggagca ccacttataa cccctccctc     180
aagagtcgag tcaccatgtc agtagacacg tccaaaaacc agttctccct gaagctgacg     240
tctgtgaccg ccgcggacac ggccgtgtat tactgtgcga gagacaaaga ttactttatt     300
tcgggaagtt attataattg gttcgacccc tggggccagg gaaccctggt caccgtctcc     360
tcagcctcca ccaagggccc atcggtcttc cccctggcac cctcctccaa gagcacctct     420
gggggcacag cggccctggg ctgcctggtc aaggactact tccccgaacc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gacagttgag     660
cgcaaatgtt gggcgcgcca cacatgccca ccgtgcccag cacctgaact cctgggggga     720
ccgtcagtct tcctcttccc cccaaaaccc aaggacaccc tcatgatctc ccggaccccct    780 gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcccagccc ccatcgagaa aaccatctcc    1020
```

```
aaagccaaag ggcagccccg agaaccacag gtgtacaccc tgcccccatc ccgggatgag    1080
ctgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa tga                                  1353

<210> SEQ ID NO 70
<211> LENGTH: 648
<212> TYPE: DNA
<213> ORGANISM: Homo sapiens

<400> SEQUENCE: 70
gaggccggcc aggtgttgac gcagtctcca gccaccctgt ctgtgtctcc aggggaaaga      60
gccaccctct cctgcagggc cagtcagagt gttggcagca acttagcctg gtaccagcag     120
aaacctggcc aggctcccag gctcctcatc tatggtgcat ccaccagggc cactggtatc     180
ccagccaggt tcagtggcag tgggtctggg acagagttca ctctcaccat cagcagcctg     240
cagtctgaag attttgcagt ttattactgt cagcaggggt ggacgttcgg ccaagggacc     300
aaggtggaaa tcaaacgaac tgtggctgca ccatctgtct tcatcttccc gccatctgat     360
gagcagttga aatctggaac tgcctctgtt gtgtgcctgc tgaataactt ctatcccaga     420
gaggccaaag tacagtggaa ggtggataac gccctccaat cgggtaactc ccaggagagt     480
gtcacagagc aggacagcaa ggacagcacc tacagcctca gcagcaccct gacgctgagc     540
aaagcagact acgagaaaca caaactctac gcctgcgaag tcacccatca gggcctgagc     600
tcgcccgtca caaagagctt caacagggga gagtgtgcgg ccgcatga                  648

<210> SEQ ID NO 71
<211> LENGTH: 1374
<212> TYPE: DNA
<213> ORGANISM: Homo sapiens

<400> SEQUENCE: 71
gagttaatta atctggtgga gtctggggga ggcgtggtcc ggcctgggag gtccctgaga      60
ctctcctgtg cagcctctgg aatcatcttc agtagctata ctatgcactg ggtccgccag     120
gctccaggca aggggctgga gtgggtggca cttatctcat atgatggaac caataaaaac     180
tacggagact ccgtgacggg ccgattcacc atctccagag acaattccaa gaatacgctg     240
tatctgcaaa tgaacagcct gagacctgag gacacggctg tgtattactg tgcgagggct     300
cgggtcatag taccagctgg cagcaactac aaccagtacg gtatggacgt ctggggccaa     360
gggaccacgg tcaccgtctc ctcagcctcc accaagggcc catcggtctt ccccctggca     420
ccctcctcca agagcacctc tgggggcaca gcggccctgg gctgcctggt caaggactac     480
ttccccgaac cggtgacggt gtcgtggaac tcaggcgccc tgaccaacgg cgtgcacacc     540
ttcccggctg tcctacagtc ctcaggactc tactccctca gcagcgtggt gaccgtgccc     600
tccagcagct tgggcaccca gacctacatc tgcaacgtga atcacaagcc cagcaacacc     660
aaggtggaca agacagttga gcgcaaatgt tgggcgcgcc acacatgccc accgtgccca     720
gcacctgaac tcctgggggg accgtcagtc ttcctcttcc ccccaaaacc caaggacacc     780
ctcatgatct cccggacccc tgaggtcaca tgcgtggtgg tggacgtgag ccacgaagac     840
cctgaggtca agttcaactg gtacgtggac ggcgtggagg tgcataatgc caagacaaag     900
```

```
ccgcgggagg agcagtacaa cagcacgtac cgtgtggtca gcgtcctcac cgtcctgcac    960
caggactggc tgaatggcaa ggagtacaag tgcaaggtct ccaacaaagc cctcccagcc   1020
cccatcgaga aaaccatctc caaagccaaa gggcagcccc gagaaccaca ggtgtacacc   1080
ctgcccccat cccgggatga gctgaccaag aaccaggtca gcctgacctg cctggtcaaa   1140
ggcttctatc ccagcgacat cgccgtggag tgggagagca atgggcagcc ggagaacaac   1200
tacaagacca cgcctcccgt gctggactcc gacggctcct tcttcctcta cagcaagctc   1260
accgtggaca agagcaggtg gcagcagggg aacgtcttct catgctccgt gatgcatgag   1320
gctctgcaca accactacac gcagaagagc ctctccctgt ctccgggtaa atga         1374

<210> SEQ ID NO 72
<211> LENGTH: 648
<212> TYPE: DNA
<213> ORGANISM: Homo sapiens

<400> SEQUENCE: 72
gaggccggcc agtctgtgct gactcagcca ccctcagtgt ccgtgtcccc aggacagaca     60
gccagcatca cctgctctgg aaataagttg ggcaataaat atgcttgctg gtatcagcag    120
aagccaggcc agtcccctat actgatcatc tatcaagata gaagcggcc ctcagggatc    180 cctgagcgtt tctctggctc caactctggg aacacagcca ctctgaccat cagcgggacc    240
caggctatgg atgaggctga ctattattgt caggcgtggg acagcgacac tgtggttttc    300
ggcggaggga ccaagctgac cgtcctaggt cagcccaagg ctgccccctc ggtcactctg    360
ttcccgccct cctctgagga gcttcaagcc aacaaggcca cactggtgtg tctcataagt    420
gacttctacc cgggagccgt gacagtggcc tggaaggcag acagcagccc cgtcaaggcg    480
ggagtggaga ccaccacacc ctccaaacaa agcaacaaca gtacgcggc cagcagctat    540 ctgagcctga cgcctgagca gtggaagtcc cacagaagct acagctgcca ggtcacgcat    600
gaagggagca ccgtggagaa gacagtggcc cctacagaat gttcatag               648

<210> SEQ ID NO 73
<211> LENGTH: 1320
<212> TYPE: DNA
<213> ORGANISM: Artificial Sequence
<220> FEATURE:
<223> OTHER INFORMATION: AflIII/HindIII pARC/Fab expression cassette

<400> SEQUENCE: 73
tcacatgttc tttcctgcgt tatccctga ttctgtggat aaccgtatta ccgcctttga     60
gtgagctgat accgctcgcc gcagccgaac gaccgagcgc agcgagtcag tgagcgagga    120
agcggaagag cgcccaatac gcaaaccgcc tctccccgcg cgttggccga ttcattaatg    180
cagctggcac gacaggtttc ccgactggaa agcgggcagt gagcgcaacg caattaatgt    240
gagttagctc actcattagg caccccaggc tttacacttt atgcttccgg ctcgtatgtt    300
gtgtggaatt gtgagcggat aacaatttca cacaggagga attctatgaa aaagacagct    360
atcgcgattg cagtggcact ggctggtttc gctaccgtag cgcaggccgg cctatgcggc    420
cgcataagta tgaaggagga cagctatgaa aataaaaaca ggtgcacgca tcctcgcatt    480
atccgcatta cgacgatga tgttttccgc ctcggctctc gccttaatta atctagaggc    540
ggtggcggtt ctatggtgag caagggcgag gagctgttca ccggggtggt gcccatcctg    600
gtcgagctgg acggcgacgt aaacggccac aagttcagcg tgtccggcga gggcgagggc    660
gatgccacct acggcaagct gaccctgaag ttcatctgca ccaccggcaa gctgcccgtg    720
```

```
cccctggccca ccctcgtgac caccctgacc tacggcgtgc agtgcttcag ccgctacccc      780
gaccacatga agcagcacga cttcttcaag tccgccatgc ccgaaggcta cgtccaggag      840
cgcaccatct tcttcaagga cgacggcaac tacaagaccc gcgccgaggt gaagttcgag      900
ggcgacaccc tggtgaaccg catcgagctg aagggcatcg acttcaagga ggacggcaac      960
atcctggggc acaagctgga gtacaactac aacagccaca acgtctatat catggccgac     1020
aagcagaaga acggcatcaa ggtgaacttc aagatccgcc acaacatcga ggacggcagc     1080
gtgcagctcg ccgaccacta ccagcagaac ccccccatcg gcgacggccc cgtgctgctg     1140
cccgacaacc actacctgag cacccagtcc gccctgagca agacccccaa cgagaagcgc     1200
gatcacatgg tcctgctgga gttcgtgacc gccgccggga tcactctcgg catggacgag     1260
ctgtacaagt aagctagatt ggcgcgccat caccatcacc atcactaagc atgcaagctt     1320
```

<210> SEQ ID NO 74
<211> LENGTH: 19
<212> TYPE: PRT
<213> ORGANISM: Artificial Sequence
<220> FEATURE:
<223> OTHER INFORMATION: OmpA leader

<400> SEQUENCE: 74

Met Lys Lys Thr Ala Ile Ala Ile Ala Val Ala Leu Ala Gly Phe Ala
1               5                   10                  15

Thr Val Ala

<210> SEQ ID NO 75
<211> LENGTH: 26
<212> TYPE: PRT
<213> ORGANISM: Artificial Sequence
<220> FEATURE:
<223> OTHER INFORMATION: MalE leader

<400> SEQUENCE: 75

Met Lys Ile Lys Thr Gly Ala Arg Ile Leu Ala Leu Ser Ala Leu Thr
1               5                   10                  15

Thr Met Met Phe Ser Ala Ser Ala Leu Ala
            20                  25

<210> SEQ ID NO 76
<211> LENGTH: 6
<212> TYPE: PRT
<213> ORGANISM: Artificial Sequence
<220> FEATURE:
<223> OTHER INFORMATION: Poly-His tag

<400> SEQUENCE: 76

His His His His His His
1               5

<210> SEQ ID NO 77
<211> LENGTH: 1281
<212> TYPE: DNA
<213> ORGANISM: Artificial Sequence
<220> FEATURE:
<223> OTHER INFORMATION: AflIII/HindIII pARC/SC expression cassette

<400> SEQUENCE: 77

```
tcacatgttc tttcctgcgt tatccccctga ttctgtggat aaccgtatta ccgcctttga       60
gtgagctgat accgctcgcc gcagccgaac gaccgagcgc agcgagtcag tgagcgagga      120
agcggaagag cgcccaatac gcaaaccgcc tctccccgcg cgttggccga ttcattaatg      180
```

```
cagctggcac gacaggtttc ccgactggaa agcgggcagt gagcgcaacg caattaatgt      240
gagttagctc actcattagg cacccaggc tttacacttt atgcttccgg ctcgtatgtt       300
gtgtggaatt gtgagcggat aacaatttca cacaggagga attctatgaa aaagacagct    360
atcgcgattg cagtggcact ggctggtttc gctaccgtag cgcaggccgg cctatgcggc    420
cgcaggtggc ggtggctcgg cggtggtgg atccggtggc ggtggctcgg gaggcggtgg     480
gtccttaatt aatctagagg cggtggcggt tctatggtga gcaagggcga ggagctgttc    540
accggggtgg tgcccatcct ggtcgagctg gacggcgacg taaacggcca caagttcagc    600
gtgtccggcg agggcgaggg cgatgccacc tacggcaagc tgaccctgaa gttcatctgc    660
accaccggca agctgcccgt gccctggccc accctcgtga ccaccctgac ctacggcgtg    720
cagtgcttca gccgctaccc cgaccacatg aagcagcacg acttcttcaa gtccgccatg    780
cccgaaggct acgtccagga gcgcaccatc ttcttcaagg acgacggcaa ctacaagacc    840
cgcgccgagg tgaagttcga gggcgacacc ctggtgaacc gcatcgagct gaagggcatc    900
gacttcaagg aggacggcaa catcctgggg cacaagctgg agtacaacta caacagccac    960
aacgtctata tcatggccga caagcagaag aacggcatca aggtgaactt caagatccgc    1020
cacaacatcg aggacggcag cgtgcagctc gccgaccact accagcagaa cacccccatc    1080
ggcgacggcc ccgtgctgct gcccgacaac cactacctga gcacccagtc cgccctgagc    1140 aaagaccca acgagaagcg cgatcacatg gtcctgctgg agttcgtgac cgccgccggg      1200
atcactctcg gcatggacga gctgtacaag taagctagat tggcgcgcca tcaccatcac    1260
catcactaag catgcaagct t                                               1281

<210> SEQ ID NO 78
<211> LENGTH: 20
<212> TYPE: PRT
<213> ORGANISM: Artificial Sequence
<220> FEATURE:
<223> OTHER INFORMATION: Linker

<400> SEQUENCE: 78

Gly Gly Gly Gly Ser Gly Gly Gly Gly Ser Gly Gly Gly Gly Ser Gly
1               5                   10                  15

Gly Gly Gly Ser
            20

<210> SEQ ID NO 79
<211> LENGTH: 51
<212> TYPE: DNA
<213> ORGANISM: Artificial Sequence
<220> FEATURE:
<223> OTHER INFORMATION: Primer

<400> SEQUENCE: 79
tatagtggcc ggccagcagt tgacccagtc tccatcctcc ctgtctgcat c              51

<210> SEQ ID NO 80
<211> LENGTH: 35
<212> TYPE: DNA
<213> ORGANISM: Artificial Sequence
<220> FEATURE:
<223> OTHER INFORMATION: Primer

<400> SEQUENCE: 80
atagtggccg gccagcagat gacccagtct ccatc                                35
```

```
<210> SEQ ID NO 81
<211> LENGTH: 39
<212> TYPE: DNA
<213> ORGANISM: Artificial Sequence
<220> FEATURE:
<223> OTHER INFORMATION: Primer

<400> SEQUENCE: 81
tatagtggcc ggccaggtga tgactcagac tccactctc                              39

<210> SEQ ID NO 82
<211> LENGTH: 42
<212> TYPE: DNA
<213> ORGANISM: Artificial Sequence
<220> FEATURE:
<223> OTHER INFORMATION: Primer

<400> SEQUENCE: 82
tatagtggcc ggccagttga cgcagtctcc agccaccctg tc                          42

<210> SEQ ID NO 83
<211> LENGTH: 45
<212> TYPE: DNA
<213> ORGANISM: Artificial Sequence
<220> FEATURE:
<223> OTHER INFORMATION: Primer

<400> SEQUENCE: 83
tatagtggcc ggccaggtgt tgacgcagtc tccagccacc ctgtc                       45

<210> SEQ ID NO 84
<211> LENGTH: 35
<212> TYPE: DNA
<213> ORGANISM: Artificial Sequence
<220> FEATURE:
<223> OTHER INFORMATION: Primer

<400> SEQUENCE: 84
atagtggccg gccaggtgat gacccagtct ccaga                                  35

<210> SEQ ID NO 85
<211> LENGTH: 35
<212> TYPE: DNA
<213> ORGANISM: Artificial Sequence
<220> FEATURE:
<223> OTHER INFORMATION: Primer

<400> SEQUENCE: 85
atagtggccg gccagacact cacgcagtct ccagc                                  35

<210> SEQ ID NO 86
<211> LENGTH: 54
<212> TYPE: DNA
<213> ORGANISM: Artificial Sequence
<220> FEATURE:
<223> OTHER INFORMATION: Primer

<400> SEQUENCE: 86
tatagtggcc ggccaggtgc tgacacagtc tccagacttt cagtctgtga ctcc             54

<210> SEQ ID NO 87
<211> LENGTH: 45
<212> TYPE: DNA
<213> ORGANISM: Artificial Sequence
<220> FEATURE:
<223> OTHER INFORMATION: Primer

<400> SEQUENCE: 87
```
agtcatgcgg ccgcacactc tcccctgttg aagctctttg tgacg                45

<210> SEQ ID NO 88
<211> LENGTH: 42
<212> TYPE: DNA
<213> ORGANISM: Artificial Sequence
<220> FEATURE:
<223> OTHER INFORMATION: Primer

<400> SEQUENCE: 88
atagtgttaa ttaacctggt gcagtctggg gctgaggtga ag                   42

<210> SEQ ID NO 89
<211> LENGTH: 47
<212> TYPE: DNA
<213> ORGANISM: Artificial Sequence
<220> FEATURE:
<223> OTHER INFORMATION: Primer

<400> SEQUENCE: 89
atagtgttaa ttaacttgag ggagtctggt cctgcgctgg tgaaacc              47

<210> SEQ ID NO 90
<211> LENGTH: 36
<212> TYPE: DNA
<213> ORGANISM: Artificial Sequence
<220> FEATURE:
<223> OTHER INFORMATION: Primer

<400> SEQUENCE: 90
gtacgtttaa ttaacctggt ggagtctggg ggaggc                          36

<210> SEQ ID NO 91
<211> LENGTH: 34
<212> TYPE: DNA
<213> ORGANISM: Artificial Sequence
<220> FEATURE:
<223> OTHER INFORMATION: Primer

<400> SEQUENCE: 91
gtagtgttaa ttaacctggt ggagtctggg ggag                            34

<210> SEQ ID NO 92
<211> LENGTH: 60
<212> TYPE: DNA
<213> ORGANISM: Artificial Sequence
<220> FEATURE:
<223> OTHER INFORMATION: Primer

<400> SEQUENCE: 92
atagtgttaa ttaacctggt ggagtctggg ggaggcttgg tccagcctgg ggggtccctg   60

<210> SEQ ID NO 93
<211> LENGTH: 47
<212> TYPE: DNA
<213> ORGANISM: Artificial Sequence
<220> FEATURE:
<223> OTHER INFORMATION: Primer

<400> SEQUENCE: 93
atagtgttaa ttaacctgca ggagtcgggc ccaggactgg tgaagcc              47

<210> SEQ ID NO 94
<211> LENGTH: 35
<212> TYPE: DNA
<213> ORGANISM: Artificial Sequence

```
<220> FEATURE:
<223> OTHER INFORMATION: Primer

<400> SEQUENCE: 94
tagtgttaat taacctggtg cagtctggag cagag                              35

<210> SEQ ID NO 95
<211> LENGTH: 39
<212> TYPE: DNA
<213> ORGANISM: Artificial Sequence
<220> FEATURE:
<223> OTHER INFORMATION: Primer

<400> SEQUENCE: 95
atagtgttaa ttaacctgca gcagtcaggt ccaggactg                          39

<210> SEQ ID NO 96
<211> LENGTH: 60
<212> TYPE: DNA
<213> ORGANISM: Artificial Sequence
<220> FEATURE:
<223> OTHER INFORMATION: Primer

<400> SEQUENCE: 96
atagtgttaa ttaacctggt gcagtctggc catgaggtga agcagcctgg ggcctcagtg   60

<210> SEQ ID NO 97
<211> LENGTH: 40
<212> TYPE: DNA
<213> ORGANISM: Artificial Sequence
<220> FEATURE:
<223> OTHER INFORMATION: Primer

<400> SEQUENCE: 97
gcatgttcgg cgcgcctcac aagatttggg ctctgctttc                         40

<210> SEQ ID NO 98
<211> LENGTH: 44
<212> TYPE: DNA
<213> ORGANISM: Artificial Sequence
<220> FEATURE:
<223> OTHER INFORMATION: Primer

<400> SEQUENCE: 98
gtagcaggcg cgcccaacat ttgcgctcaa ctgtcttgtc cacc                    44

<210> SEQ ID NO 99
<211> LENGTH: 38
<212> TYPE: DNA
<213> ORGANISM: Artificial Sequence
<220> FEATURE:
<223> OTHER INFORMATION: Primer

<400> SEQUENCE: 99
ggctctgggc gcgccgggca tgtgtgagtt gtgtcacc                           38

<210> SEQ ID NO 100
<211> LENGTH: 38
<212> TYPE: DNA
<213> ORGANISM: Artificial Sequence
<220> FEATURE:
<223> OTHER INFORMATION: Primer

<400> SEQUENCE: 100
gtgctgggcg cgccgggcat gggggaccat atttggac                           38
```

<210> SEQ ID NO 101
<211> LENGTH: 38
<212> TYPE: DNA
<213> ORGANISM: Artificial Sequence
<220> FEATURE:
<223> OTHER INFORMATION: Primer

<400> SEQUENCE: 101
ggaggtgggc gcgccgggca gggcacagtc acatcctg                    38

<210> SEQ ID NO 102
<211> LENGTH: 35
<212> TYPE: DNA
<213> ORGANISM: Artificial Sequence
<220> FEATURE:
<223> OTHER INFORMATION: Primer

<400> SEQUENCE: 102
aagacgcggc gcgccggcag ctcagcaatc actgg                       35

<210> SEQ ID NO 103
<211> LENGTH: 33
<212> TYPE: DNA
<213> ORGANISM: Artificial Sequence
<220> FEATURE:
<223> OTHER INFORMATION: Primer

<400> SEQUENCE: 103
tatagtggcc ggccagtctg ccctgactca gcc                         33

<210> SEQ ID NO 104
<211> LENGTH: 33
<212> TYPE: DNA
<213> ORGANISM: Artificial Sequence
<220> FEATURE:
<223> OTHER INFORMATION: Primer

<400> SEQUENCE: 104
tatagtggcc ggccagtctg tgctgactca gcc                         33

<210> SEQ ID NO 105
<211> LENGTH: 45
<212> TYPE: DNA
<213> ORGANISM: Artificial Sequence
<220> FEATURE:
<223> OTHER INFORMATION: Primer

<400> SEQUENCE: 105
tatagtggcc ggccagtctg tgctgactca gccaccctca gtgtc            45

<210> SEQ ID NO 106
<211> LENGTH: 45
<212> TYPE: DNA
<213> ORGANISM: Artificial Sequence
<220> FEATURE:
<223> OTHER INFORMATION: Primer

<400> SEQUENCE: 106
tatagtggcc ggccagtctg agctgactca gccaccctca gtgtc            45

<210> SEQ ID NO 107
<211> LENGTH: 45
<212> TYPE: DNA
<213> ORGANISM: Artificial Sequence
<220> FEATURE:
<223> OTHER INFORMATION: Primer

<400> SEQUENCE: 107

```
tatagtggcc ggccagtctg tgctgactca gccaccctcg gtgtc            45

<210> SEQ ID NO 108
<211> LENGTH: 35
<212> TYPE: DNA
<213> ORGANISM: Artificial Sequence
<220> FEATURE:
<223> OTHER INFORMATION: Primer

<400> SEQUENCE: 108
atagtggccg gccagtctga gctgactcag gaccc                       35

<210> SEQ ID NO 109
<211> LENGTH: 35
<212> TYPE: DNA
<213> ORGANISM: Artificial Sequence
<220> FEATURE:
<223> OTHER INFORMATION: Primer

<400> SEQUENCE: 109
tatagtggcc ggccagactg tggtgactca ggagc                       35

<210> SEQ ID NO 110
<211> LENGTH: 33
<212> TYPE: DNA
<213> ORGANISM: Artificial Sequence
<220> FEATURE:
<223> OTHER INFORMATION: Primer

<400> SEQUENCE: 110
tatagtggcc ggccagcctg tgctgactca gcc                         33

<210> SEQ ID NO 111
<211> LENGTH: 33
<212> TYPE: DNA
<213> ORGANISM: Artificial Sequence
<220> FEATURE:
<223> OTHER INFORMATION: Primer

<400> SEQUENCE: 111
tatagtggcc ggccagcctg tgctgactca atc                         33

<210> SEQ ID NO 112
<211> LENGTH: 45
<212> TYPE: DNA
<213> ORGANISM: Artificial Sequence
<220> FEATURE:
<223> OTHER INFORMATION: Primer

<400> SEQUENCE: 112
agtcatgcgg ccgctgaaca ttctgtaggg gccactgtct tctcc            45

<210> SEQ ID NO 113
<211> LENGTH: 48
<212> TYPE: DNA
<213> ORGANISM: Artificial Sequence
<220> FEATURE:
<223> OTHER INFORMATION: Primer

<400> SEQUENCE: 113
agtcatgcgg ccgcctatga acattctgta ggggccactg tcttctcc         48

<210> SEQ ID NO 114
<211> LENGTH: 1493
<212> TYPE: DNA
<213> ORGANISM: Artificial Sequence
```

<220> FEATURE:
<223> OTHER INFORMATION: AflIII/HindIII pCI/IRES expression cassette

<400> SEQUENCE: 114

| | | |
|---|---|---|
| gtacttaata cgactcacta taggctagcc accatggaag ccccagctca gcttctcttc | 60 |
| ctcctgctac tctggctccc agataccacc ggagaggccg gcctaagcgg ccgcatgacc | 120 |
| gcccctctcc ctcccccccc cctaacgtta ctggccgaag ccgcttgaat aaggccggtg | 180 |
| tgcgtttgtc tatatgttat tttccaccat attgccgtct tttggcaatg tgagggcccg | 240 |
| gaaacctggc cctgtcttct tgacgagcat tcctaggggt cttttcccctc tcgccaaagg | 300 |
| aatgcaaggt ctgttgaatg tcgtgaagga agcagttcct ctggaagctt cttgaagaca | 360 |
| aacaacgtct gtagcgaccc tttgcaggca gcggaacccc ccacctggcg acaggtgcct | 420 |
| ctgcggctaa aagccacgtg tataagatac acctgcaaag gcggcacaac cccagtgcca | 480 |
| cgttgtgagt tggatagttg tggaaagagt caaatggctc tcctcaagcg tattcaacaa | 540 |
| ggggctgaag gatgcccaga aggtacccca ttgtatggga tctgatctgg ggcctcggtg | 600 |
| cacatgcttt acatgtgttt agtcgaggtt aaaaaaacgt ctaggccccc cgaaccacgg | 660 |
| ggacgtggtt ttcctttgaa aaacacgatg ataatatggc cgccaccatg gagtttgggc | 720 |
| tgagctggct ttttcttgtg gctattttaa aaggtgtcca gtgtgagtta attaatgagg | 780 |
| cgcgccacac atgcccaccg tgcccagcac ctgaactcct gggggggaccg tcagtcttcc | 840 |
| tcttcccccc aaaacccaag gacaccctca tgatctcccg gacccctgag gtcacatgcg | 900 |
| tggtggtgga cgtgagccac gaagaccctg aggtcaagtt caactggtac gtggacggcg | 960 |
| tggaggtgca taatgccaag acaaagccgc gggaggagca gtacaacagc acgtaccgtg | 1020 |
| tggtcagcgt cctcaccgtc ctgcaccagg actggctgaa tggcaaggag tacaagtgca | 1080 |
| aggtctccaa caaagccctc ccagccccca tcgagaaaac catctccaaa gccaagggc | 1140 |
| agccccgaga accacaggtg tacaccctgc ccccatcccg ggatgagctg accaagaacc | 1200 |
| aggtcagcct gacctgcctg gtcaaaggct tctatcccag cgacatcgcc gtggagtggg | 1260 |
| agagcaatgg gcagccggag aacaactaca agaccacgcc tcccgtgctg gactccgacg | 1320 |
| gctccttctt cctctacagc aagctcaccg tggacaagag caggtggcag caggggaacg | 1380 |
| tcttctcatg ctccgtgatg catgaggctc tgcacaacca ctacacgcag aagagcctct | 1440 |
| ccctgtctcc gggtaaatga cggccgcttc cctttagtga ggggttaatg ctt | 1493 |

<210> SEQ ID NO 115
<211> LENGTH: 20
<212> TYPE: PRT
<213> ORGANISM: Artificial Sequence
<220> FEATURE:
<223> OTHER INFORMATION: Human kappa light chain leader

<400> SEQUENCE: 115

Met Glu Ala Pro Ala Gln Leu Leu Phe Leu Leu Leu Leu Trp Leu Pro
1               5                   10                  15

Asp Thr Thr Gly
            20

<210> SEQ ID NO 116
<211> LENGTH: 19
<212> TYPE: PRT
<213> ORGANISM: Artificial Sequence
<220> FEATURE:
<223> OTHER INFORMATION: Human heavy chain leader

<400> SEQUENCE: 116

Met Glu Phe Gly Leu Ser Trp Leu Phe Leu Val Ala Ile Leu Lys Gly
1               5                   10                  15

Val Gln Cys

<210> SEQ ID NO 117
<211> LENGTH: 226
<212> TYPE: PRT
<213> ORGANISM: Artificial Sequence
<220> FEATURE:
<223> OTHER INFORMATION: Human heavy CH2/CH3 constant domain

<400> SEQUENCE: 117

Ala Arg His Thr Cys Pro Pro Cys Pro Ala Pro Glu Leu Leu Gly Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
        115                 120                 125

Thr Leu Pro Pro Ser Arg Asp Glu Leu Thr Lys Asn Gln Val Ser Leu
    130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
    210                 215                 220

Gly Lys
225

<210> SEQ ID NO 118
<211> LENGTH: 8
<212> TYPE: PRT
<213> ORGANISM: Artificial Sequence
<220> FEATURE:
<223> OTHER INFORMATION: Linker

<400> SEQUENCE: 118

Gly Gly Gly Gly Ser Ser Ser Ser
1               5

<210> SEQ ID NO 119
<211> LENGTH: 11
<212> TYPE: PRT
<213> ORGANISM: Artificial Sequence
<220> FEATURE:

```
<223> OTHER INFORMATION: Encoded after stop codon following human
      CH2/CH3 constant domain

<400> SEQUENCE: 119

Arg Pro Leu Pro Phe Ser Glu Gly Leu Met Leu
1               5                   10
```